(12) United States Patent
Ni et al.

(10) Patent No.: US 7,056,516 B2
(45) Date of Patent: Jun. 6, 2006

(54) I-FLICE, A NOVEL INHIBITOR OF TUMOR NECROSIS FACTOR RECEPTOR-1 AND CD-95 INDUCED APOPTOSIS

(75) Inventors: Jian Ni, Germantown, MD (US); Craig A. Rosen, Laytonsville, MD (US); Vishva M. Dixit, Los Altos Hills, CA (US); Reiner L. Gentz, Belo Horizonte-Mg (BR); Joseph J. Kenny, San Diego, CA (US)

(73) Assignees: Human Genome Sciences, Inc., Rockville, MD (US); The Regents of the University, Ann Arbor, MI (US)

( * ) Notice: Subject to any disclaimer, the term of this patent is extended or adjusted under 35 U.S.C. 154(b) by 157 days.

(21) Appl. No.: 10/713,208

(22) Filed: Nov. 17, 2003

(65) Prior Publication Data

US 2004/0121387 A1    Jun. 24, 2004

Related U.S. Application Data

(60) Division of application No. 09/489,155, filed on Jan. 21, 2000, now Pat. No. 6,680,171, which is a continuation of application No. 09/009,893, filed on Jan. 21, 1998, now Pat. No. 6,623,938.

(60) Provisional application No. 60/034,205, filed on Jan. 21, 1997, provisional application No. 60/054,800, filed on Aug. 5, 1997.

(51) Int. Cl.
*A61K 39/00* (2006.01)
*A61K 39/395* (2006.01)
*C07K 14/00* (2006.01)
*C12P 21/08* (2006.01)

(52) U.S. Cl. .............................. 424/185.1; 424/192.1; 530/350; 530/387.3

(58) Field of Classification Search ................ 530/350, 530/324, 387.3; 424/185.1, 19, 192.1
See application file for complete search history.

(56) References Cited

FOREIGN PATENT DOCUMENTS

| | | |
|---|---|---|
| CA | 2285669 | 10/1998 |
| EP | 0 816 499 A2 | 1/1998 |
| EP | 0 841 399 A2 | 5/1998 |
| WO | WO 94/04686 | 3/1994 |
| WO | WO 96/05306 A2 | 2/1996 |
| WO | WO 97/32996 A1 | 9/1997 |
| WO | WO 98/33883 A1 | 8/1998 |
| WO | WO 98/44104 A2 | 10/1998 |
| WO | WO 98/52963 A1 | 11/1998 |

OTHER PUBLICATIONS

Ngo et al., in The Protein Folding Problem and Tertiary Structure Prediction, 1994, Merz, et al., (ed.), Birkhauser, Boston, MA, pp. 433 and 492-495.*
Mikayama et al, Molecular cloning and functional expression of a cDNA encoding gycosylation-inhibiting factor, Nov. 1993, Proc. Natl. Acad. Sci, USA vol. 90: 10056-10060.*
Skolnick et al., From genes to protein structure and function: novel applications of computational approaches in the genomic era, Jan. 2000, Trends in Biotech. 18(1): 34-39.*
Attwood et al., The babel of bioinformatics, Oct. 2000, Science 290 (5491): 471-473.*
U.S. Appl. No. 09/912,293, filed Jul. 26, 2001, Rosen et al., pp. 1-75 (pp. 1 & 2 partially redacted); portion of Table 2; and SEQ ID Nos.: 164706, 215903, and 219749.
Adams, M.D. et al., "Complementary DNA sequencing: expressed sequence tags and human genome project," *Science* 252:1651-1656 (1991).
Adams, M.D. et al., "Sequence identification of 2,375 human brain genes," *Nature* 355:632-634 (1992).
Adams, M.D. et al., "Rapid cDNA sequence (expressed sequence tags) from a directionally cloned human infant brain cDNA library," *Nature genetics* 4:373-380 (1993).
Adams, M.D. et al., "Initial assessment of human gene diversity and expression patterns based upon 83 million nucleotides of cDNA sequence," *Nature* 377:3-174 (1995).

(Continued)

*Primary Examiner*—Christina Chan
*Assistant Examiner*—Phuong Huynh
(74) *Attorney, Agent, or Firm*—Human Genome Sciences, Inc.

(57) ABSTRACT

The present invention relates to a novel I-FLICE-1 or I-FLICE-2 protein which is a novel inhibitor of TNFR-1 and CD-95 induced apoptosis. In particular, isolated nucleic acid molecules are provided encoding the human I-FLICE-1 or I-FLICE-2 protein. I-FLICE-1 or I-FLICE-2 polypeptides are also provided as are vectors, host cells and recombinant methods for producing the same. The invention further relates to screening methods for identifying agonists and antagonists of I-FLICE-1 or I-FLICE-2 activity. Also provided are therapeutic methods for treating diseases and disorders associated with apoptosis.

19 Claims, 11 Drawing Sheets

OTHER PUBLICATIONS

Alnemri, E.S et al., "Human ICE/CED-3 protease nomenclature," *Cell* 87:171 (Oct. 1996).
Bertin, J. et al., "Death effector domain-containing herpesvirus and poxvirus proteins inhibit both Fas- and TNFR1-induced apoptosis," *Proc. Natl. Sci. Acad. USA* 94:1172-1176 (Feb. 1997).
Boldin, M.P. et al., "Involvement of MACH, a novel MORT1/FADD-interacting protease, in Fas/APO-1- and TNF Receptor-induced cell death," *Cell* 85:803-815 (Jun. 1996).
Chinnaiyan, A.M. et al., "FADD, a novel death domain-containing protein, interacts with the death domain of Fas and initiates apoptosis," *Cell* 81:505-512 (1995).
Chinnaiyan, A.M. et al., "FADD/MORT1 is a common mediator of CD95 (Fas/APO-1) and tumor necrosis factor-receptor-induced apoptosis," *J. Biol. Chem.* 271(9):4961-4965 (Mar. 1996).
Chinnaiyan, A.M. and V.M. Dixit, "The cell-death machine," *Curr. Biol.* 6:55-562 (May 1996).
Fernandes-Alnemri, T. et al., "*In vitro* activation of CPP32 and Mch3 by Mch4, a novel human apoptotic cysteine protease containing two FADD-like domains," *Proc. Natl. Acad. Sci. USA* 93:7464-7469 (Jul. 1996).
Fraser, A. and G. Evan, "A license to kill," *Cell* 85:781-784 (Jun. 1996).
Henkart, P.A., "ICE family proteases: mediators of all apoptotic cell death?," *Immunity* 4:195-201 (Mar. 1996).
Hu, S. et al., "A novel family of viral death effector domain-containing molecules that inhibit both CD-95 and tumor necrosis factor receptor-1-induced apoptosis," *J. Biol. Chem.* 272(15):9621-9624 (Apr. 1997).
Hu, S. et al., "I-FLICE, a novel inhibitor of tumor necrosis factor receptor-1 and CD-95 induced apoptosis," *J. Biol. Chem.* 272(28):17255-17257 (Jul. 1997).
Irlmer, M. et al., "Inhibition of death receptor signals by cellular FLIP," *Nature* 388:190-195 (Jul. 1997).
Muzio, M. et al., "FLICE, a novel FADD-homologous ICE/CED-3-like protease, is recruited to the CD95 (Fas/APO-1) death-inducing signaling complex," *Cell* 85:817-827 (Jun. 1996).
Muzio, M. et al., "FLICE induced apoptosis in a cell-free system," *J. Biol. Chem.* 272(5):2952-2956 (Jan. 1997).
O'Rourke, K.M. et al., "Thrombospondin 1 and Thrombospondin 2 are expressed as both homo- and heterotrimers," *J. Biol. Chem.* 267(35):24921-24924 (1992).
Rotonda, J. et al., "The three-dimensional structure of apopain/CPP32, a key mediator of apoptosis," *Nature Structural Biology* 3(7):619-625 (Jul. 1996).
Shen, Y. and T.E. Shenk, "Viruses and apoptosis," Curr. Biol. 5:105-111 (1995).
Shu, H.-B. et al., "Casper is a FADD- and caspase-related inducer of apoptosis," *Immunity* 6:751-763 (Jun. 1997).
Srinivasula, S.M. et al., "Molecular ordering of the Fas-apoptotic pathway: The Fas/APO-1 protease Mch5 is a CrmA-inhibitable protease that activates multiple Ced-3/ICE-like cysteine proteases," *Proc. Natl. Acad. Sci. USA* 93:14486-14491 (Dec. 1996).
Thome, M. et al., "Viral FLICE-inhibitory protein (FLIPs) prevent apoptosis induced by death receptors," *Nature* 386:517-521 (Apr. 1997).
Vincenz, C. and V.M. Dixit, "Fas-associated death domain protein interleukin 1β-converting enzyme 2 (FLICE2), an ICE/Ced-3 homologue, is proximately involved in CD95- and p55-mediated death signaling," *J. Biol. Chem.* 272(10):6578-6583 (Mar. 1997).
Walker, N.P.C. et al., "Crystal structure of the cysteine protease interleukin 1β-converting enzyme: a $(p20/p10)_2$ homodimer," *Cell* 78:343-352 (1994).
Wilson, K.P. et al., "Structure and mechanism of interleukin 1β-converting enzyme," *Nature* 370:270-275 (1994).
NCBI Entrez, Genbank Report, Accession No. T05118, from Adams, M.D. et al. (1993), with revision history.
NCBI Entrez, Genbank Report, Accession No. Z42895, from Auffray, C. et al. (1994), with revision history.
NCBI Entrez, Genbank Report, Accession No. T48754, from Hillier, L. et al. (1995), with revision history.
NCBI Entrez, Genbank Report, Accession No. F13176, from Auffray, C. et al., (1995), with revision history.
NCBI Entrez, Genbank Report, Accession No. T93307, from Hillier, L. et al. (1995), with revision history.
NCBI Entrez, Genbank Report, Accession No. H15978, from Hillier, L. et al., (1995), with revision history.
NCBI Entrez, Genbank Report, Accession No. H15052, from Hillier, L. et al. (1995), with revision history.
NCBI Entrez, Genbank Report, Accession No. T30922, from Adams, M.D. et al. (1995), with revision history.
NCBI Entrez, Genbank Report, Accession No. T30864, from Adams, M.D. et al. (1995), with revision history.
NCBI Entrez, Genbank Report, Accession No. H68343, from Hillier, L. et al. (1995), with revision history.
NCBI Entrez, Genbank Report, Accession No. D83882, Takeda, J. (Apr. 1996), with revision history.
NCBI Entrez, Genbank Report, Accession No. W52946, from Hillier, L. et al. (May 1996), with revision history.
NCBI Entrez, Genbank Report, Accession No. W60406, from Hillier, L. et al. (Jun. 1996), with revision history.
NCBI Entrez, Genbank Report, Accession No. W23795, from Hillier, L. et al. (Aug. 1996), with revision history.
NCBI Entrez, Genbank Report, Accession No. N94588, from Hillier, L. et al. (Aug. 1996), with revision history.
NCBI Entrez, Genbank Report, Accession No. C05795, from Takeda J. (Oct. 1996), with revision history.
NCBI Entrez, Genbank Report, Accession No. C05730, Takeda J. (Oct. 1996), with revision history.
NCBI Entrez, Genbank Report, Accession No. AA135811, from Hillier, L. et al. (Nov. 1996), with revision history.
NCBI Entrez, Genbank Report, Accession No. AA149562, from Hillier, L. et al. (Dec. 1996), with revision history.
NCBI Entrez, Genbank Report, Accession No. AA151642, from Hillier, L. et al. (Dec. 1996), with revision history.
NCBI Entrez, Genbank Report, Accession No. AA198928, from Marra, M. et al. (Feb. 1997), with revision history.
NCBI Entrez, Genbank Report, Accession No. AA296309, from Adams, M.D. et al. (Apr. 1997), with revision history.
NCBI Entrez, Genbank Report, Accession No. AA296229, from Adams, M.D. et al. (Apr. 1997), with revision history.
NCBI Entrez, Genbank Report, Accession No. AA296174, from Adams, M.D. et al. (Apr. 1997), with revision history.
NCBI Entrez, Genbank Report, Accession No. AA302978, from Adams, M.D. et al. (Apr. 1997), with revision history.
NCBI Entrez, Genbank Report, Accession No. AA302968, from Adams, M.D. et al. (Apr. 1997), with revision history.
NBCI Entrez, Genbank Report, Accession No. AA358042, from Adams, M.D. et al. (Apr. 1997), with revision history.
NCBI Entrez, Genbank Report, Accession No. AA358043, from Adams, M.D. et al. (Apr. 1997), with revision history.
NCBI Entrez, Genbank Report, Accession No. AA379905, from Adams, M.D. et al. (Apr. 1997), with revision history.

NCBI Entrez, Genbank Report, Accession No. AA364006, from Adams, M.D. et al. (Apr. 1997), with revision history.
NCBI Entrez, Genbank Report, Accession No. AA001257, from Hillier, L. et al. (May 1997), with revision history.
NCBI Entrez, Genbank Report, Accession No. AA002262, from Hillier, L. et al. (May 1997), with revision history.
NCBI Entrez, Genbank Report, Accession No. AA115793, from Hillier, L. et al. (May 1997), with revision history.
NCBI Entrez, Genbank Report, Accession No. AA115792, from Hillier, L. et al. (May 1997), with revision history.
NCBI Entrez, Genbank Report, Accession No. AA453766, from Hillier, L. et al. (Jun. 1997), with revision history.
NCBI Entrez, Genbank Report, Accession No. AA453850, from Hillier, L. et al. (Jun. 1997), with revision history.
NCBI Entrez, Genbank Report, Accession No. AA501289, from Marra, M. et al. (Jul. 1997), with revision history.
NCBI Entrez, Genbank Report, Accession No. U97075, from Irlmer, M. et al. (Jul. 1997), with revision history.
NCBI Entrez, Genbank Report, Accession No. U97076, from Irlmer, M. et al. (Jul. 1997), with revision history.
NCBI Entrez, Genbank Report, Accession No. U97074, from Irlmer, M. et al. (Jul. 1997), with revision history.
NCBI Entrez, Genbank Report, Accession No. AF010127, from Shu, H.B. et al. (Jul. 1997), with revision history.
NCBI Entrez, Genbank Report, Accession No. AF005775, from Inohara, N. et al. (Jul. 1997), with revision history.
NCBI Entrez, Genbank Report, Accession No. AF005774, from Inohara, N. et al. (Jul. 1997), with revision history.
NCBI Entrez, Genbank Report, Accession No. AA526099, from NCI-CGAP (Aug. 1997), with revision history.
NCBI Entrez, Genbank Report, Accession No. AA467995, from NCI-CGAP (Aug. 1997), with revision history.
NCBI Entrez, Genbank Report, Accession No. AA468056, from NCI-CGAP (Aug. 1997), with revision history.
NCBI Entrez, Genbank Report, Accession No. AA467756, from NCI-CGAP (Aug. 1997), with revision history.
NCBI Entrez, Genbank Report, Accession No. AA467938, from NCI-CGAP (Aug. 1997), with revision history.
NCBI Entrez, Genbank Report, Accession No. AA229005, from NCI-CGAP (Aug. 1997), with revision history.
NCBI Entrez, Genbank Report, Accession No. AA565691, from NCI-CGAP (Sep. 1997), with revision history.
NCBI Entrez, Genbank Report, Accession No. AA558404, from NCI-CGAP (Sep. 1997), with revision history.
NCBI Entrez, Genbank Report, Accession No. AA525331, from NCI-CGAP (Sep. 1997), with revision history.
NCBI Entrez, Genbank Report, Accession No. AF00619, from Srinivasula, S.M. et al. (Sep. 1997), with revision history.
NCBI Entrez, Genbank Report, Accession No. AF009618, from Srinivasula, S.M. et al. (Sep. 1997), with revision history.
NCBI Entrez, Genbank Report, Accession No. AF009616, from Srinivasula, S.M. et al. (Sep. 1997), with revision history.
NCBI Entrez, Genbank Report, Accession No. AF009617, from Srinivasula, S.M. et al. (Sep. 1997), with revision history.
NCBI Entrez, Genbank Report, Accession No. AA663074, from Hillier, L. et al. (Nov. 1997), with revision history.
NCBI Entrez, Genbank Report, Accession No. AA613966, from NCI-CGAP (Oct. 1997), with revision history.
NCBI Entrez, Genbank Report, Accession No. AA610255, from NCI-CGAP (Dec. 1997), with revision history.
NCBI Entrez, Genbank Report, Accession No. AA70614, from Hillier, L. et al. (Dec. 19967), with revision history.
NCBI Entrez, Genbank Report, Accession No. Z80780, from Albig, W. et al. (Sep. 2, 1996).
NCBI Entrez, Genbank Report, Accession No. AF009619, from Srinivasula, S.M. et al. (Sep. 23, 1997).
NCBI Entrez, Genbank Report, Accession No. U85059, from Han, D.K.M. et al. (Nov. 4, 1997).
NCBI Entrez, Genbank Report, Accession No. Y14039, from Goltsev, Y.V. et al. (Nov. 30, 1997).
NCBI Entrez, Genbank Report, Accession No. Y14040, from Goltsev, Y.V. et al. (Nov. 30, 1997).
NCBI Entrez, Genbank Report, Accession No. Y14041, from Goltsev, Y.V. et al. (Nov. 30, 1997).
NCBI Entrez, Genbank Report, Accession No. Y14042, from Goltsev, Y.V. et al. (Nov. 30, 1997).
NCBI Entrez, Genbank Report, Accession No. AF015451, from Rasper, D.M. et al. (May 16, 1998).
NCBI Entrez, Genbank Report, Accession No. AF015452, from Rasper, D.M. et al. (May 16, 1998).
NCBI Entrez, Genbank Report, Accession No. Z85996, from Palmer, S. (Jun. 18, 1998).
NCBI Entrez, Genbank Report, Accession No. Z15027, from Bougueleret, L. (Jun. 25, 1997).
NCBI Entrez, Genbank Report, Accession No. M34133, from Woese, C.R. (Apr. 27, 1993).
NCBI Entrez, Genbank Report, Accession No. M80463, from Hu, Y. et al. (Mar. 4, 1994).
NCBI Entrez, Genbank Report, Accession No. X80877, from Kelly, M.M. et al. (Apr. 2, 1998).
NCBI Entrez, Genbank Report, Accession No. U22416, from Chen, H. et al. (Jul. 26, 1996).
NCBI Entrez, Genbank Report, Accession No. U16720, from Sanjanwala, B. et al. (Oct. 28, 1995).
NCBI Entrez, Genbank Report, Accession No. U22427, fom Bennasar, A. et al. (Mar. 26, 1996).
NCBI Entrez, Genbank Report, Accession No. U25280, from Bennasar, A. et al. (Mar. 26, 1996).
NCBI Entrez, Genbank Report, Accession No. U26415, from Bennasar, A. et al. (Apr. 4, 1996).
NCBI Entrez, Genbank Report, Accession No. Z68873, from Odell, C. (Nov. 23, 1999).
NCBI Entrez, Genbank Report, Accession No. S79859, from Barnier, J.V. et al. (Feb. 11, 1996).
NCBI Entrez, Genbank Report, Accession No. U58659, from Frischer, M.E. et al. (Jun. 19, 1996).
NCBI Entrez, Genbank Report, Accession No. D90605, from Matsuoka, Y. (Feb. 7, 1996).
NCBI Entrez, Genbank Report, Accession No. D90634, from Matsuoka, Y. (Feb. 7, 1996).
NCBI Entrez, Genbank Report, Accession No. U67563, from Bult, C.J. et al. (Jan. 28, 1998).
NCBI Entrez, Genbank Report, Accession No. U64001, from Pinhassi, J. et al. (Sep. 13, 1999).
NCBI Entrez, Genbank Report, Accession No. Z80780, from Albig, W. et al. (Sep. 27, 1996).
NCBI Entrez, Genbank Report, Accession No. Z85996, from Tripodis, N. et al. (Nov. 23, 1999).
NCBI Entrez, Genbank Report, Accession No. Z76668, from Moore, E.R.B. et al. (Mar. 25, 1997).
NCBI Entrez, Genbank Report, Accession No. U70698, from Rappe, M.S. et al. (Dec. 21, 1997).
NCBI Entrez, Genbank Report, Accession No. AF038653, from Metcalf, W.W. et al. (Nov. 5, 1998).

NCBI Entrez, Genbank Report, Accession No. F05214, from Auffray, C. et al. (month "first seen at NCBI" Feb. 1995), with sequence revision history and disclaimer.
NCBI Entrez, Genbank Report, Accession No. P39188, from Claverie, J.M. et al. (month "first seen at NCBI" Mar. 1995), with sequence revision history and disclaimer.
NCBI Entrez, Genbank Report, Accession No. P39189, from Claverie, J.M. et al. (month "first seen at NCBI" Mar. 1995), with sequence revision history and disclaimer.
NCBI Entrez, Genbank Report, Accession No. P39190, from Claverie, J.M. et al. (month "first seen at NCBI" Mar. 1995), with sequence revision history and disclaimer.
NCBI Entrez, Genbank Report, Accession No. P39191, from Claverie, J.M. et al. (month "first seen at NCBI" Mar. 1995), with sequence revision history and disclaimer.
NCBI Entrez, Genbank Report, Accession No. P39192, from Claverie, J.M. et al. (month "first seen at NCBI" Mar. 1995), with sequence revision history and disclaimer.
NCBI Entrez, Genbank Report, Accession No. P39193, from Claverie, J.M. et al. (month "first seen at NCBI" Mar. 1995), with sequence revision history and disclaimer.
NCBI Entrez, Genbank Report, Accession No. P39194, from Claverie, J.M. et al. (month "first seen at NCBI" Mar. 1995), with sequence revision history and disclaimer.
NCBI Entrez, Genbank Report, Accession No. P39195, from Claverie, J.M. et al. (month "first seen at NCBI" Mar. 1995), with sequence revision history and disclaimer.
NCBI Entrez, Genbank Report, Accession No. R16389, from Hillier, L. et al. (month "first seen at NCBI" Apr. 1995), with sequence revision history and disclaimer.
NCBI Entrez, Genbank Report, Accession No. Z68273, from Mungall, A. (month "first seen at NCBI" Dec. 1995), with sequence revision history and disclaimer.
NCBI Entrez, Genbank Report, Accession No. AAC50602, from Munzio, M. et al. (month "first seen at NCBI" Jun. 1996), with sequence revision history and disclaimer.
NCBI Entrez, Genbank Report, Accession No. CAA66854, from Boldin, M.P. et al. (month "first seen at NCBI" Jul. 1996), with sequence revision history and disclaimer.
NCBI Entrez, Genbank Report, Accession No. AAC50645, from Fernandes-Alnemri, T.F. et al. (month "first seen at NCBI" Jul. 1996), with sequence revision history and disclaimer.
NCBI Entrez, Genbank Report, Accession No. CAA66853, Boldin, M.P. et al. (month "first seen at NCBI" Jul. 1996), with sequence revision history and disclaimer.
NCBI Entrez, Genbank Report, Accession No. CAA66855, from Boldin, M.P. et al. (month "first seen at NCBI" Jul. 1996), with sequence revision history and disclaimer.
NCBI Entrez, Genbank Report, Accession No. AAC50644, from Fernandes-Alnemri, T.F. et al. (month "first seen at NCBI" Aug. 1996), with sequence revision history and disclaimer.
NCBI Entrez, Genbank Report, Accession No. AAC29881, from Johnson, A.L. et al. (month "first seen at NCBI" Aug. 1996), with sequence revision history and disclaimer.
NCBI Entrez, Genbank Report, Accession No. Z83844, from Pearce, A. (month "first seen at NCBI" Jan. 1997), with sequence revision history and disclaimer.
NCBI Entrez, Genbank Report, Accession No. AAB46730, Vincenz, C. and Dixit, V.M. (month "first seen at NCBI" Feb. 1997), with sequence revision history and disclaimer.
NCBI Entrez, Genbank Report, Accession No. AAB49034, Westin, E.H. and Gorse, K.M. (month "first seen at NCBI" Mar. 1997), with sequence revision history and disclaimer.
NCBI Entrez, Genbank Report, Accession No. AA295653, Adams, M.D. et al. (month "first seen at NCBI" Apr. 1997), with sequence revision history and disclaimer.
NCBI Entrez, Genbank Report, Accession No. AA358043, Adams, M.D. et al. (month "first seen at NCBI" Apr. 1997), with sequence revision history and disclaimer.
NCBI Entrez, Genbank Report, Accession No. AA384922, Adams, M.D. et al. (month "first seen at NCBI" Apr. 1997), with sequence revision history and disclaimer.
NCBI Entrez, Genbank Report, Accession No. JC5238, from Sosa, M.A. et al. (create date: Apr. 1997).
NCBI Entrez, Genbank Report, Accession No. Z93930, from Clark, G. et al. (month "first seen at NCBI" Jul. 1997), with sequence revision history and disclaimer.
NCBI Entrez, Genbank Report, Accession No. AAC53281, Irmler, M. et al. (month "first seen at NCBI" Jul. 1997), with sequence revision history and disclaimer.
NCBI Entrez, Genbank Report, Accession No. AAC15825, from Inohara, N. et al. (month "first seen at NCBI" Jul. 1997), with sequence revision history and disclaimer.
NCBI Entrez, Genbank Report, Accession No. AAC15826, from Inohara, N. et al. (month "first seen at NCBI" Jul. 1997), with sequence revision history and disclaimer.
NCBI Entrez, Genbank Report, Accession No. AC002476, from Graves, T. et al. (month "first seen at NCBI" Aug. 1997), with sequence revision history and disclaimer.
NCBI Entrez, Genbank Report, Accession No. AAB70909, Srinivasula, S.M. et al. (month "first seen at NCBI" Sep. 1997), with sequence revision history and disclaimer.
NCBI Entrez, Genbank Report, Accession No. AAB70910, Srinivasula, S.M. et al. (month "first seen at NCBI" Sep. 1997), with sequence revision history and disclaimer.
NCBI Entrez, Genbank Report, Accession No. AAB70912, Srinivasula, S.M. et al. (month "first seen at NCBI" Sep. 1997), with sequence revision history and disclaimer.
NCBI Entrez, Genbank Report, Accession No. AAB70913, Srinivasula, S.M. et al. (month "first seen at NCBI" Sep. 1997), with sequence revision history and disclaimer.
NCBI Entrez, Genbank Report, Accession No. Z98941, from Kershaw, J. (month "first seen at NCBI" Sep. 1997), with sequence revision history and disclaimer.
NCBI Entrez, Genbank Report, Accession No. CAA04196, Kioschis, P. et al. (month "first seen at NCBI" Oct. 1997), with sequence revision history and disclaimer.
NCBI Entrez, Genbank Report, Accession No. B37964, Mahairas, G.G. et al. (month "first seen at NCBI" Oct. 1997), with sequence revision history and disclaimer.
NCBI Entrez, Genbank Report, Accession No. B40201, Mahairas, G.G. et al. (month "first seen at NCBI" Oct. 1997), with sequence revision history and disclaimer.
NCBI Entrez, Genbank Report, Accession No. AAC51843, Lahn, B.T. and Page, D.C. (month "first seen at NCBI" Nov. 1997), with sequence revision history and disclaimer.
NCBI Entrez, Genbank Report, Accession No. CAA74366, Goltsev, Y.V. et al. (month "first seen at NCBI" Nov. 1997), with sequence revision history and disclaimer.
NCBI Entrez, Genbank Report, Accession No. CAA74367, Goltsev, Y.V. et al. (month "first seen at NCBI" Nov. 1997), with sequence revision history and disclaimer.
NCBI Entrez, Genbank Report, Accession No. CAA74368, Goltsev, Y.V. et al. (month "first seen at NCBI" Nov. 1997), with sequence revision history and disclaimer.
NCBI Entrez, Genbank Report, Accession No. CAA74369, Goltsev, Y.V. et al. (month "first seen at NCBI" Nov. 1997), with sequence revision history and disclaimer.

NCBI Entrez, Genbank Report, Accession No. AC003101, from Birren, B. et al. (month "first seen at NCBI" Nov. 1997), with sequence revision history and disclaimer.
NCBI Entrez, Genbank Report, Accession No. AL009183, from Pearce, A. (month "first seen at NCBI" Dec. 1997), with sequence revision history and disclaimer.
NCBI Entrez, Genbank Report, Accession No. AC004060, Stone, N.E. et al. (month "first seen at NCBI" Jan. 1998), with sequence revision history and disclaimer.
NCBI Entrez, Genbank Report, Accession No. AAB99792, Hu, S. et al. (month "first seen at NCBI" Feb. 1998), with sequence revision history and disclaimer.
NCBI Entrez, Genbank Report, Accession No. AAB99793, Hu, S. et al. (month "first seen at NCBI" Feb. 1998), with sequence revision history and disclaimer.
NCBI Entrez, Genbank Report, Accession No. AAB99794, Hu, S. et al. (month "first seen at NCBI" Feb. 1998), with sequence revision history and disclaimer.
NCBI Entrez, Genbank Report, Accession No. AF041458, Hu, S. et al. (month "first seen at NCBI" Feb. 1998), with sequence revision history and disclaimer.
NCBI Entrez, Genbank Report, Accession No. AF041459, Hu, S. et al. (month "first seen at NCBI" Feb. 1998), with sequence revision history and disclaimer.
NCBI Entrez, Genbank Report, Accession No. AF041460, Hu, S. et al. (month "first seen at NCBI" Feb. 1998), with sequence revision history and disclaimer.
NCBI Entrez, Genbank Report, Accession No. AF041461, Hu, S. et al. (month "first seen at NCBI" Feb. 1998), with sequence revision history and disclaimer.
NCBI Entrez, Genbank Report, Accession No. AF041462, Hu, S. et al. (month "first seen at NCBI" Feb. 1998), with sequence revision history and disclaimer.
NCBI Entrez, Genbank Report, Accession No. AC004099, from Birren, B. et al. (month "first seen at NCBI" Feb. 1998), with sequence revision history and disclaimer.
NCBI Entrez, Genbank Report, Accession No. AC004106, from Muzny, D. et al. (month "first seen at NCBI" Feb. 1998), with sequence revision history and disclaimer.
NCBI Entrez, Genbank Report, Accession No. AC004216, from Muzny, D. et al. (month "first seen at NCBI" Feb. 1998), with sequence history and disclaimer.
NCBI Entrez, Genbank Report, Accession No. AC004491, from Waterston, R. et al. (month "first seen at NCBI" Mar. 1998), with sequence revision history and disclaimer.
NCBI Entrez, Genbank Report, Accession No. AC004590, from Birren, B. et al. (month "first seen at NCBI" Apr. 1998), with sequence revision history and disclaimer.
NCBI Entrez, Genbank Report, Accession No. AAC16440, from Rasper, D.M. et al. (month "first seen at NCBI" May 1998), with sequence revision history and disclaimer.
NCBI Entrez, Genbank Report, Accession No. AAC16441, from Rasper, D.M. et al. (month "first seen at NCBI" May 1998), with sequence revision history and disclaimer.
NCBI Entrez, Genbank Report, Accession No. AF015450, from Rasper, D.M. et al. (month "first seen at NCBI" May 1998), with sequence revision history and disclaimer.
NCBI Entrez, Genbank Report, Accession No. AI000325, from NCI-CGAP (month "first seen at NCBI" Jun. 1998), with sequence revision history and disclaimer.
NCBI Entrez, Genbank Report, Accession No. AC004821, from Waterston, R.H. et al. (month "first seen at NCBI" Jun. 1998), with sequence revision history and disclaimer.
NCBI Entrez, Genbank Report, Accession No. AC005089, from Waterston, R.H. et al. (month "first seen at NCBI" Jun. 1998), with sequence revision history and disclaimer.
NCBI Entrez, Genbank Report, Accession No. AC004834, from Waterston, R.H. et al. (month "first seen at NCBI" Jun. 1998), with sequence revision history and disclaimer.
NCBI Entrez, Genbank Report, Accession No. AA922168, from NCI-CGAP (month "first seen at NCBI" Jun. 1998), with sequence revision history and disclaimer.
NCBI Entrez, Genbank Report, Accession No. AAC40131, from Sakamaki, K. et al. (month "first seen at NCBI" Jun. 1998), with sequence revision history and disclaimer.
NCBI Entrez, Genbank Report, Accession No. AAC25713, from Rueda, B.R. et al. (month "first seen at NCBI" Jul. 1998), with sequence revision history and disclaimer.
NCBI Entrez, Genbank Report, Accession No. AAC32602, from Johnson, A.L. and Bridgham, J.T. (month "first seen at NCBI" Aug. 1998), with sequence revision history and disclaimer.
NCBI Entrez, Genbank Report, Accession No. AL031302, from Griffiths, M. (month "first seen at NCBI" Aug. 1998), with sequence revision history and disclaimer.
NCBI Entrez, Genbank Report, Accession No. AC005529, from Ying, F. et al. (month "first seen at NCBI" Aug. 1998), with sequence revision history and disclaimer.
NCBI Entrez, Genbank Report, Accession No. AI139524, from NCI-CGAP (month "first seen at NCBI" Sep. 1998), with sequence revision history and disclaimer.
NCBI Entrez, Genbank Report, Accession No. AI041643, from NCI-CGAP (month "first seen at NCBI" Sep. 1998), with sequence revision history and disclaimer.
NCBI Entrez, Genbank Report, Accession No. AL031427, from Hall, R. (month "first seen at NCBI" Sep. 1998), with sequence revision history and disclaimer.
NCBI Entrez, Genbank Report, Accession No. AL031447, from Wray, P. (month "first seen at NCBI" Sep. 1998), with sequence revision history and disclaimer.
NCBI Entrez, Genbank Report, Accession No. AI094800, from NCI/NINDS-CGAP (month "first seen at NCBI" Oct. 1998), with sequence revision history and disclaimer.
NCBI Entrez, Genbank Report, Accession No. AI160682, from NCI-CGAP (month "first seen at NCBI" Oct. 1998), with sequence revision history and disclaimer.
NCBI Entrez, Genbank Report, Accession No. AC005803, from Birren, B. et al. (month "first seen at NCBI" Oct. 1998), with sequence revision history and disclaimer.
NCBI Entrez, Genbank Report, Accession No. AC005952, from Lamerdin, J.E. et al. (month "first seen at NCBI" Nov. 1998), with sequence revision history and disclaimer.
NCBI Entrez, Genbank Report, Accession No. AI274957, from NCI-CGAP (month "first seen at NCBI" Nov. 1998), with sequence revision history and disclaimer.
NCBI Entrez, Genbank Report, Accession No. AL033392, from Williams, S. (month "first seen at NCBI" Nov. 1998), with sequence revision history and disclaimer.
NCBI Entrez, Genbank Report, Accession No. AI289177, from NCI-CGAP (month "first seen at NCBI" Dec. 1998), with sequence revision history and disclaimer.
NCBI Entrez, Genbank Report, Accession No. AI302167, from NCI-CGAP (month "first seen at NCBI" Dec. 1998), with sequence revision history and disclaimer.
NCBI Entrez, Genbank Report, Accession No. AI342264, from NCI-CGAP (month "first seen at NCBI" Dec. 1998), with sequence revision history and disclaimer.

NCBI Entrez, Genbank Report, Accession No. AC006088, from Muzny, D. et al. (month "first seen at NCBI" Dec. 1998), with sequence revision history and disclaimer.

NCBI Entrez, Genbank Report, Accession No. AI283206, from NCI-CGAP (month "first seen at NCBI" Jan. 1999), with sequence revision history and disclaimer.

NCBI Entrez, Genbank Report, Accession No. AI347041, from NCI-CGAP (month "first seen at NCBI" Feb. 1999), with sequence revision history and disclaimer.

NCBI Entrez, Genbank Report, Accession No. AI312598, from NCI-CGAP (month "first seen at NCBI" Feb. 1999), with sequence revision history and disclaimer.

New England Biolabs Catalog, 199/31994, p. 110 (1993).

Kuby et al., 1994, Immunology, second edition, pp. 85-96.

Abaza et al., J. or Protein Chemistry 11(5):433-444, 1992.

Skolnick et al. From genes to protein structure and function: novel applications of computational approaches in the genomic era, Jan. 2000, Trends in Biotech. 18(1):34-39.

Attwood et al., The babel of bioinformatics, Oct. 2000, Science 290(5491):471-473.

Mikayma et al., Molecular cloning and functional expression of a cDNA encoding glycosylation-inhibiting factor, Nov. 1993, Proc. Natl. Acad. Sci., USA vol. 90: 10056-10060.

* cited by examiner

```
        10                     30                    50
CGATCGCCCAGCACCAAGTCCGCTTCCAGGCTTTCGGTTTCTTTGCCTCCATCTTGGGTG 70                    90                   110
CGCCTTCCCGGCGTCTAGGGGAGCGAAGGCTGAGGTGGCAGCGGCAGGAGAGTCCGGCCG 130                   150                   170
CGACAGGACGAACTCCCCCACTGGAAAGGATTCTGAAAGAAATGAAGTCAGCCCTCAGAA 190                   210                   230
ATGAAGTTGACTGCCTGCTGGCTTTCTGTTGACTGGCCCGGAGCTGTACTGCAAGACCCT 250                   270                   290
TGTGAGCTTCCCTAGTCTAAGAGTAGGATGTCTGCTGAAGTCATCCATCAGGTTGAAGAA
                              M  S  A  E  V  I  H  Q  V  E  E
        310                   330                   350
GCACTTGATACAGATGAGAAGGAGATGCTGCTCTTTTTGTGCCGGGATGTTGCTATAGAT
 A  L  D  T  D  E  K  E  M  L  L  F  L  C  R  D  V  A  I  D 370                   390                   410
GTGGTTCCACCTAATGTCAGGGACCTTCTGGATATTTTACGGGAAAGAGGTAAGCTGTCT
 V  V  P  P  N  V  R  D  L  L  D  I  L  R  E  R  G  K  L  S 430                   450                   470
GTCGGGGACTTGGCTGAACTGCTCTACAGAGTGAGGCGATTTGACCTGCTCAAACGTATC
 V  G  D  L  A  E  L  L  Y  R  V  R  R  F  D  L  L  K  R  I 490                   510                   530
TTGAAGATGGACAGAAAAGCTGTGGAGACCCACCTGCTCAGGAACCCTCACCTTGTTTCG
 L  K  M  D  R  K  A  V  E  T  H  L  L  R  N  P  H  L  V  S 550                   570                   590
GACTATAGAGTGCTGATGGCAGAGATTGGTGAGGATTTGGATAAATCTGATGTGTCCTCA
 D  Y  R  V  L  M  A  E  I  G  E  D  L  D  K  S  D  V  S  S 610                   630                   650
TTAATTTTCCTCATGAAGGATTACATGGGCCGAGGCAAGATAAGCAAGGAGAAGAGTTTC
 L  I  F  L  M  K  D  Y  M  G  R  G  K  I  S  K  E  K  S  F 670                   690                   710
TTGGACCTTGTGGTTGAGTTGGAGAAACTAAATCTGGTTGCCCCAGATCAACTGGATTTA
 L  D  L  V  V  E  L  E  K  L  N  L  V  A  P  D  Q  L  D  L 730                   750                   770
TTAGAAAAATGCCTAAAGAACATCCACAGAATAGACCTGAAGACAAAAATCCAGAAGTAC
 L  E  K  C  L  K  N  I  H  R  I  D  L  K  T  K  I  Q  K  Y 790                   810                   830
AAGCAGTCTGTTCAAGGAGCAGGGACAAGTTACAGGAATGTTCTCCAAGCAGCAATCCAA
 K  Q  S  V  Q  G  A  G  T  S  Y  R  N  V  L  Q  A  A  I  Q 850                   870                   890
AAGAGTCTCAAGGATCCTTCAAATAACTTCAGGCTCCATAATGGGAGAAGTAAAGAACAA
 K  S  L  K  D  P  S  N  N  F  R  L  H  N  G  R  S  K  E  Q 910                   930                   950
AGACTTAAGGAACAGCTTGGCGCTCAACAAGAACCAGTGAAGAAATCCATTCAGGAATCA
 R  L  K  E  Q  L  G  A  Q  Q  E  P  V  K  K  S  I  Q  E  S 970                   990                  1010
GAAGCTTTTTTGCCTCAGAGCATACCTGAAGAGAGATACAAGATGAAGAGCAAGCCCCTA
 E  A  F  L  P  Q  S  I  P  E  E  R  Y  K  M  K  S  K  P  L
       1030                  1050                  1070
```

FIG.1A

```
GGAATCTGCCTGATAATCGATTGCATTGGCAATGAGACAGAGCTTCTTCGAGACACCTTC
 G  I  C  L  I  I  D  C  I  G  N  E  T  E  L  L  R  D  T  F
          1090                1110                1130
ACTTCCCTGGGCTATGAAGTCCAGAAATTCTTGCATCTCAGTATGCATGGTATATCCAG
 T  S  L  G  Y  E  V  Q  K  F  L  H  L  S  M  H  G  I  S  Q
          1150                1170                1190
ATTCTTGGCCAATTTGCCTGTATGCCCGAGCACCGAGACTACGACAGCTTTGTGTGTGTC
 I  L  G  Q  F  A  C  M  P  E  H  R  D  Y  D  S  F  V  C  V
          1210                1230                1250
CTGGTGAGCCGAGGAGGCTCCCAGAGTGTGTATGGTGTGGATCAGACTCACTCAGGGCTC
 L  V  S  R  G  G  S  Q  S  V  Y  G  V  D  Q  T  H  S  G  L
          1270                1290                1310
CCCCTGCATCACATCAGGAGGATGTTCATGGGAGATTCATGCCCTTATCTAGCAGGGAAG
 P  L  H  H  I  R  R  M  F  M  G  D  S  C  P  Y  L  A  G  K
          1330                1350                1370
CCAAAGATGTTTTTTATTCAGAACTATGTGGTGTCAGAGGGCCAGCTGGAGGACAGCAGC
 P  K  M  F  F  I  Q  N  Y  V  V  S  E  G  Q  L  E  D  S  S
          1390                1410                1430
CTCTTGGAGGTGGATGGGCCAGCGATGAAGAATGTGGAATTCAAGGCTCAGAAGCGAGGG
 L  L  E  V  D  G  P  A  M  K  N  V  E  F  K  A  Q  K  R  G
          1450                1470                1490
CTGTGCACAGTTCACCGAGAAGCTGACTTCTTCTGGAGCCTGTGTACTGCGGACATGTCC
 L  C  T  V  H  R  E  A  D  F  F  W  S  L  C  T  A  D  M  S
          1510                1530                1550
CTGCTGGAGCAGTCTCACAGCTCACCGTCCCTGTACCTGCAGTGCCTCTCCCAGAAACTG
 L  L  E  Q  S  H  S  S  P  S  L  Y  L  Q  C  L  S  Q  K  L
          1570                1590                1610
AGACAAGAAAGAAAACGCCCACTCCTGGATCTTCACATTGAACTCAATGGCTACATGTAT
 R  Q  E  R  K  R  P  L  L  D  L  H  I  E  L  N  G  Y  M  Y
          1630                1650                1670
GATTGGAACAGCAGAGTTTCTGCCAAGGAGAAATATTATGTCTGGCTGCAGCACACTCTG
 D  W  N  S  R  V  S  A  K  E  K  Y  Y  V  W  L  Q  H  T  L
          1690                1710                1730
AGAAAGAAACTTATCCTCTCCTACACATAAGAAACCAAAAGGCTGGGCGTAGTGGCTCGC
 R  K  K  L  I  L  S  Y  T  *
          1750                1770                1790
ACCTGTAATCCCAGCACTTTGGGAGGCCAAGGAGGGCGGATCACTTCAGGTCAGGAGTTC
          1810                1830                1850
GAGACCAGCCTGGCCAACATGGTAAACGCTGTCCCTAGTAAGAGTGCAAAAATTAGCTGG
          1870                1890                1910
GTGTGGGTGTGGGTACCTGTGTTCCCAGTTACTTGGGAGGCTGAGGTGGGAGGATCTTTT
          1930                1950                1970
GAACCCAGGAGTTCAGGGTCATAGCATGCTGTGATTGTGCCTACGAATAGCCACTGCATA
          1990                2010                2030
CCAACCTGGGCAATATAGCAAGATCCCATCTTTTTAAAAAAAAAAAAAAAAAAAA
```

FIG.1B

```
  1   MD---------------FSRNLYDIGEQLDSEDLASLK  huFLICE(U58143)
  1   MKSQGQHWYSSSDKNCKVSFREKLLILDSNLGVQDVENLK  HuMch4(U60519)
  1   MSAEVIH-----------------QVEEALDTDEKEMLL  HSALZ11Xprotein
  1   M--------------------------------------  HCEBJ50XXprotein 24   FLSLDYIPQRKQEPIKDALMLFQRLQEKRMLEESNLSFLK  huFLICE(U58143)
 41   FLCIGLVPNKKLEKSSSASDVFEHLLAEDLLSEEDPFFLA  HuMch4(U60519)
 23   FLCRDVAIDVVPPNVRD---LLDILRERGKLSVGD---LA  HSALZ11Xprotein
  2   ---------------------------------------  HCEBJ50XXprotein 64   ELLFRINRLDLLITYLNTRKEEMERELQTPGRAQISAYR  huFLICE(U58143)
 81   ELLYIIRQKKLL-QHLNCTKEEVERLL--PTRQRVSLFR  HuMch4(U60519)
 57   ELLYRVRRFDLLKRILKMDRKAVETHLLRNP--HLVSDYR  HSALZ11Xprotein
  2   ---------------------------------------  HCEBJ50XXprotein 103   VMLYQISEEVSRSELRSFKFLLQEEISKQKLDDDMNULDI  huFLICE(U58143)
117   NLLYELSEGIDSENLKDMIFLLKDSLPK----TEMTSLSF  HuMch4(U60519)
 95   VLMAEIGEDLDKSDVSSLIFLMKDYMQRGKISKEKSFLDL  HSALZ11Xprotein
  2   ---AEIGEDLDKSDVSSLIFLMKDYMQRGKISKEKSFLDL  HCEBJ50XXprotein 143   FIEMEKRVILGEGKLDILKRVCAQINKSLLKI-INDM---  huFLICE(U58143)
153   LAFLEKQGKIDEDNLTCLEDLCKTVVPKLLRN-IEKYK--  HuMch4(U60519)
135   VVELEKLNLVAPDQLDLLEKCLKNIHRIDLKTKIQKYKQS  HSALZ11Xprotein
 39   VVELEKLNLVAPDQLDLLEKCLKNIHRIDLKTKIQKYKQS  HCEBJ50XXprotein
```

FIG.2A

```
179  ---------EEFSKERSSSLEGSPDEES------NGEELC  huFLICE(U58143)
190  --------REKAIQIVTPPVDKEAESYQ------GEEEL-  HuMch4(U60519)
175  VQGAGTSYRNVLQAAIQKSLKDPSNNFRLHNGRSKEQRLK  HSALZ11Xprotein
 79  VQGAGTSYRNVLQAAIQKSLKDPSNNFR-----------  HCEBJ50XXprotein 204  GVMTISDSPREQDSESQT-------LDKVYQMKSKPRGYC  huFLICE(U58143)
215  ----VSQTDVKTFLEALP-------RAAVYRMNRNHRGLC  HuMch4(U60519)
215  EQLGAQQEPVKKSIQESEAFLPQSIPEERYKMKSKPLGIC  HSALZ11Xprotein
107  ------EEPVKKSIQESEAFLPQSIPEERYKMKSKPLGIC  HCEBJ50XXprotein 237  LIINNHNFAKAREKVPKLHSIRDRNGTHLDAGALTTTFEE  huFLICE(U58143)
244  VIVNNHSFT---------SLKDRQGTHKDAEILSHVFQW  HuMch4(U60519)
255  LIIDCIG------------------NETELLRDTFTS  HSALZ11Xprotein
141  LIIDCIG------------------NETELLRDTFTS  HCEBJ50XXprotein 277  LHFEIKPHDDCTVEQIYEILKIYQ-LMDHSNMDCFIQCIL  huFLICE(U58143)
274  LGFTVHIHNNVTKVEMEMVLQKQKDNPAHADGDCFVFCIL  HuMch4(U60519)
274  LGYEVQKFLHLSMHGISQILGQFACMPEHRDYDSFVCVLV  HSALZ11Xprotein
160  LGYEVQKFLHLSMHGISQILGQFACMPEHRDYDSFVCVLV  HCEBJ50XXprotein 316  SHGDKGIIYGTDGQEP--PIYELTSQFTGLKCPSLAGKPK  huFLICE(U58143)
314  THGRFGAVYSSDEALI--PIREIMSHFTALQCPRLAEKPK  HuMch4(U60519)
314  SRGGSQSVYGVDQTHSGLPLHHIRRMFMGDSCPYLAGKPK  HSALZ11Xprotein
200  SRGGSQSVYGVDQTHSGLPLHHIRRMFMGDSCPYLAGKPK  HCEBJ50XXprotein
```

FIG.2B

```
354  VFFIQAC--QGDNYQKGIPVETDSEEQPYLEMDLSSPQTR    huFLICE(U58143)
352  LFFIQAC--QGEEIQPSVSIEADALNPEQAPTSLQDS---    HuMch4(U60519)
354  MFFIQNYVVSEGQLEDSSLLEVDGPAMKNVEFKAQKRGLC    HSALZ11Xprotein
240  MFFIQNYVVSDGQLEDSSLLEVDGPAMKNVEFKAQKRGLC    HCEBJ50XXprotein 392  YIPDEADFLLGMATVNNCVSYRNPAEGTWYIQSLCQSLRE    huFLICE(U58143)
387  -IPAEADFLLGLATVPGYVSFRHVEEGSWYIQSLCNHLKK    HuMch4(U60519)
394  TVHREADFFWSLCTADMSLLEQSHSSPSLYLQCLSQKLRQ    HSALZ11Xprotein
280  TVHREADFFWSLCTADMSLLEQSHSSPSLYLQCLSQKLRQ    HCEBJ50XXprotein 432  RCPRGDDILTILTEVNHYEVSNKDDKKNMGKQMPQPTFTL    huFLICE(U58143)
426  LVPRHEDILSILTAVN-DDVSRRVDKDGTKKQMPQPAFTL    HuMch4(U60519)
434  --ERKRPLLDLHIELNGYMYDWNSRVSAKEKYYVWLQHTL    HSALZ11Xprotein
320  --ERG-------TIPG----SGITESKDMHFSSLGCTL    HCEBJ50XXprotein 471  RKKLVFP------SD         huFLICE(U58143)
465  RKKLVFPVPLDALSI         HuMch4(U60519)
472  RKKLIL------SYTQ        HSALZ11Xprotein
345  ----L------DVLQ         HCEBJ50XXprotein
```

FIG.2C

```
          10                  30                  50
GCGAGCTTGCAGCCTCACCGACGAGTCTCAACTAAAAGGGACTCCCGGAGCTAGGGGTGG 70                  90                 110
GGACTCGGCCTCACACAGTGATTGCCGGCTATTGGACTTTTGTCCAGTGACAGCTGAGAC 130                 150                 170
AACAAGGACCACGGGAGGAGGTGTAGGAGAGAAGCGCCGCGAACAGGCATCGCCCAGCAC 190                 210                 230
CAAGTCCGCTTCCAGGCTTTCGGTTTCTTTGCCTCCATCTTGGGTGCGCCTTCCCGGCGT 250                 270                 290
CTAGGGGAGCGAAGGCTGAGGTGGCAGCGGCAGGAGAGTCCGGCCGCGACAGGACGAGTG 310                 330                 350
CTGATGGCAGAGATTGGTGAGGATTTGGATAAATCTGATGTGTCCTCATTAATTTTCCTC
    M  A  E  I  G  E  D  L  D  K  S  D  V  S  S  L  I  F  L 370                 390                 410
ATGAAGGATTACATGGGCCGAGGCAAGATAAGCAAGGAGAAGAGTTTCTTGGACCTTGTG
 M  K  D  Y  M  G  R  G  K  I  S  K  E  K  S  F  L  D  L  V 430                 450                 470
GTTGAGTTGGAGAAACTAAATCTGGTTGCCCCAGATCAACTGGATTTATTAGAAAAATGC
 V  E  L  E  K  L  N  L  V  A  P  D  Q  L  D  L  L  E  K  C
         490                 510                 530
```

FIG.4A

```
CTAAAGAACATCCACAGAATAGACCTGAAGACAAAAATCCAGAAGTACAAGCAGTCTGTT
 L  K  N  I  H  R  I  D  L  K  T  K  I  Q  K  Y  K  Q  S  V
      550               570               590
CAAGGAGCAGGGACAAGTTACAGGAATGTTCTCCAAGCAGCAATCCAAAAGAGTCTCAAG
 Q  G  A  G  T  S  Y  R  N  V  L  Q  A  A  I  Q  K  S  L  K
      610               630               650
GATCCTTCAAATAACTTCAGGGAAGAACCAGTGAAGAAATCCATTCAGGAATCAGAAGCT
 D  P  S  N  N  F  R  E  E  P  V  K  K  S  I  Q  E  S  E  A
      670               690               710
TTTTTGCCTCAGAGCATACCTGAAGAGAGATACAAGATGAAGAGCAAGCCCCTAGGAATC
 F  L  P  Q  S  I  P  E  E  R  Y  K  M  K  S  K  P  L  G  I
      730               750               770
TGCCTGATAATCGATTGCATTGGCAATGAGACAGAGCTTCTTCGAGACACCTTCACTTCC
 C  L  I  I  D  C  I  G  N  E  T  E  L  L  R  D  T  F  T  S
      790               810               830
CTGGGCTATGAAGTCCAGAAATTCTTGCATCTCAGTATGCATGGTATATCCCAGATTCTT
 L  G  Y  E  V  Q  K  F  L  H  L  S  M  H  G  I  S  Q  I  L
      850               870               890
GGCCAATTTGCCTGTATGCCCGAGCACCGAGACTACGACAGCTTTGTGTGTGTCCTGGTG
 G  Q  F  A  C  M  P  E  H  R  D  Y  D  S  F  V  C  V  L  V
      910               930               950
AGCCGAGGAGGCTCCCAGAGTGTGTATGGTGTGGATCAGACTCACTCAGGGCTCCCCCTG
 S  R  G  G  S  Q  S  V  Y  G  V  D  Q  T  H  S  G  L  P  L
      970               990              1010
CATCACATCAGGAGGATGTTCATGGGAGATTCATGCCCTTATCTAGCAGGGAAGCCAAAG
 H  H  I  R  R  M  F  M  G  D  S  C  P  Y  L  A  G  K  P  K
     1030              1050              1070
ATGTTTTTTATTCAGAACTATGTGGTGTCAGACGGCCAGCTGGAGGACAGCAGCCTCTTG
 M  F  F  I  Q  N  Y  V  V  S  D  G  Q  L  E  D  S  S  L  L
     1090              1110              1130
GAGGTGGATGGGCCAGCGATGAAGAATGTGGAATTCAAGGCTCAGAAGCGAGGGCTGTGC
 E  V  D  G  P  A  M  K  N  V  E  F  K  A  Q  K  R  G  L  C
     1150              1170              1190
ACAGTTCACCGAGAAGCTGACTTCTTCTGGAGCCTGTGTACTGCGGACATGTCCCTGCTG
 T  V  H  R  E  A  D  F  F  W  S  L  C  T  A  D  M  S  L  L
     1210              1230              1250
GAGCAGTCTCACAGCTCACCGTCCCTGTACCTGCAGTGCCTCTCCCAGAAACTGAGACAA
 E  Q  S  H  S  S  P  S  L  Y  L  Q  C  L  S  Q  K  L  R  Q
     1270              1290              1310
GAAAGGGGGACAATTCCCGGAAGTGGAATTACAGAGTCAAAGGACATGCATTTTTCAAGC
 E  R  G  T  I  P  G  S  G  I  T  E  S  K  D  M  H  F  S  S
     1330              1350              1370
CTCGGATGCATCTTACTAGATGTCCTATAGGATGGTCATATCAGCTTTATAGGAGAGTAG
 L  G  C  I  L  L  D  V  L  *
     1390              1410              1430
CTGTGTCCCTGAATTCTCCCTGACACTGCATGCTCTTATATTTCCTCAAGTTTTGACAAT
     1450              1470              1490
TTGATAGGTGAAAAGTGGTATCTGACTGTTCAGATCTGGAAGGCTTTGTTATATAAACAT
     1510              1530              1550
TTTTTTAATGTTTATTGGCAAGAATACTTTTCTAAGAGAAACATCAGTGAGCTGGTTTCC
     1570              1590              1610
ATTTAAGCTGAATGAAGCCACAATGTACCTCAAGTATAAGATTAACTGGCCTTTTTCAGT
     1630              1650              1670
TGCACTCTAATTACAATTTAGAATGATGTTTCTGAGCCACCTGTCAAATGCATTCTGGGC
```

FIG.4B

```
     1690              1710               1730
TGTACCTCTGCGTACCCCAGGAATAAATCTCATGGCCTTCTTTACCTGGCCTCCTTAGTG
     1750              1770               1790
GTGGCCCAGCAGGAAGCGGGGGTTAGAGCAGGAGCCACTCAGCCTTCCAAGATAGATACT
     1810              1830               1850
CCATGGGCCGGTGGTATTACTGGCCTTTTGAGCCCATCCCCATTTGCATAGATGATCCAC
     1870              1890               1910
GTGGGTTATCATCTGGCTGGTATGTTCCCAGAGTGAAACTCAGCAGCCCCTTGAGGGAGG
     1930              1950               1970
GGATGGTGGCCATCAGGCCAGAGTATTGCAAGTTAGTTTGGATCATTTGCTAAGCAGCTT
     1990              2010               2030
GTGGTGCCTTCAGAAAGGAACAGTTTCAAAGAACTTTCACATCTGTTGGCTCATTTCGCC
     2050              2070               2090
CTAATGACAGTCTTCTCTTTGATATTTGCATGGCATTAAATTTTGCCTTTCTTGTTTTCT
     2110              2130               2150
CCAGAAAACGCCCACTCCTGGATCTTCACATTGAACTCAATGGCTACATGTATGATTGGA
     2170              2190               2210
ACAGCAGAGTTTCTGCCAAGGAGAAATATTATGTCTGGCTGCAGCACACTCTGAGAAAGA
     2230              2250               2270
AACTTATCTCTCCTACACATAAGAAACCAAAAGGCTGGGCGTAGTGGCTCGCACCTGTGA
     2290              2310               2330
TCCCAGCACTTTGGGAGGCCGAGGAGGGCGGATCACTTCAGGTCGGGAGTTCGAGACCAG
     2350              2370               2390
CCTGGCCAGCATGTGAACGCTGTCCCTAGTAGAAGTGCAAAAATTGGCTGGTGTGGGTGT
     2410              2430               2450
GGGTACCCTGTATTCCCAGTTGCTTGGGGGGCTGAGGTGGGAGGATCTTTTGACCCCAGG
     2470              2490               2510
AGTTCAGGGTCATAGCATGCTGTGATTGTGCCTACGAATAGCCACTGCATACCAACCTGG
     2530              2550               2570
GCAATATAGCAAGATCCCATCTCTTTAAAAAAAAAAAAAAAAAGGACAGGAACTATCTTAA
     2590
AAAAAAAAAAAAAAAAA
```

FIG.4C

I-FLICE, A NOVEL INHIBITOR OF TUMOR NECROSIS FACTOR RECEPTOR-1 AND CD-95 INDUCED APOPTOSIS

CROSS REFERENCE TO RELATED APPLICATIONS

This application is a divisional of U.S. application Ser. No. 09/489,155, filed Jan. 21, 2000, now U.S. Pat. No. 6,680,171, which is a continuation of U.S. application Ser. No. 09/009,893, filed Jan. 21, 1998, now U.S. Pat. No. 6,623,938, which claims benefit under 35 U.S.C. § 119(e) of U.S. Provisional Application Nos. 60/034,205, filed Jan. 21, 1997, and 60/054,800, filed Aug. 5, 1997, all of which are incorporated by reference herein.

FIELD OF THE INVENTION

The present invention relates to a novel inhibitor of TNFR-1 and CD-95 induced apoptosis. More specifically, isolated nucleic acid molecules are provided encoding a human I-FLICE (Inhibitor of FLICE (FADD-like ICE)) polynucleotides. I-FLICE polypeptides are also provided, as are vectors, host cells and recombinant methods for producing the same. The invention further relates to screening methods for identifying agonists and antagonists of I-FLICE activity. Also provided are therapeutic methods for treating diseases and disorders associated with apoptosis.

BACKGROUND OF THE INVENTION

The cell death machinery is conserved throughout evolution and is composed of activators, inhibitors, and effectors (Chinnaiyan, A. M. and Dixit, V. M., *Curr. Biol.* 6:555–562 (1996)). The effector arm of the cell death pathway is composed of a rapidly growing family of cysteine aspartate-specific proteases termed caspases (Alnemri, E. S., et al., *Cell* 87:171 (1996)). As implied by the name, these cysteine proteases cleave substrates following an aspartate residue (Alnemri, E. S., et al., *Cell* 87:171 (1996); Walker, N. P., et al., *Cell* 78:343–352 (1994)). Caspases are normally present as single polypeptide zymogens and contain an amino-terminal prodomain, and large and small catalytic subunits (Wilson, K. P., et al., *Nature* 370:270–274 (1994); Rotonda, J., et al., *Nat. Struct. Biol.* 3:619–625 (1996); Fraser, A. and Evan, G., *Cell* 85:781–784 (1996)). The two chain active enzyme (composed of the large and small subunits) is obtained following proteolytic processing at internal Asp residues (Wilson, K. P., et al., *Nature* 370:270–274 (1994); Rotonda, J., et al., *Nat. Struct. Biol.* 3:619–625 (1996); Fraser, A. and Evan, G., *Cell* 85:781–784 (1996)). As such, caspases are capable of activating each other in a manner analogous to zymogen activation that is observed in the coagulation cascade (Boldin, M. P., et al., *Cell* 85:805–815 (1996)). The identification of FLICE and Mch4/FLICE2 as receptor associated caspases suggested a surprisingly direct mechanism for activation of the death pathway by the cytotoxic receptors CD-95 and TNFR-1 (Boldin, M. P., et al., *Cell* 85:805–815 (1996); Muzio, M., et al., *Cell* 85:817–827 (1996); Vincenz, C. and Dixit, V. M., *J. Biol. Chem.* 272:6578–6583 (1997); Chinnaiyan, A. M., et al., *Cell* 81:505–512 (1995)). Upon activation, both receptors use their death domains to bind the corresponding domain in the adaptor molecule FADD (Fas-associated death domain protein) (Muzio, M., et al., *Cell* 85:817–827 (1996); Vincenz, C. and Dixit, V. M., *J. Biol. Chem.* 272: 6578–6583 (1997); Chinnaiyan, A. M., et al., *Cell* 81:505–512 (1995)). Dominant negative versions of FADD that lack the N-terminal segment but still retain the death domain potently inhibit both CD-95 and TNFR-1 induced apoptosis (Chinnaiyan, A. M., et al., *J. Biol. Chem.* 271: 4961–4965 (1996); Muzio, M., et al., *J. Biol. Chem.* 272: 2952–2956 (1997)). Given the importance of the N-terminal segment in engaging the death pathway, it has been termed the death effector domain (DED) (Chinnaiyan, A. M., et al., *J. Biol. Chem.* 271:4961–4965 (1996)).

Remarkably, the DED is present within the prodomain of FLICE and Mch4/FLICE2 and mutagenesis studies suggest that a homophilic interaction between the DED of FADD and the corresponding domain in FLICE or Mch4/FLICE2 is responsible for the recruitment of these proteases to the CD-95 and TNFR-1 signaling complexes (Muzio, M., et al., *Cell* 85:817–827 (1996); Vincenz, C. and Dixit, V. M., *J. Biol. Chem.* 272:6578–6583 (1997); Chinnaiyan, A. M., et al., *Cell* 81:505–512 (1995); Chinnaiyan, A. M., et al., *J. Biol. Chem.* 271:4961–4965 (1996)). Taken together, these data are consistent with FLICE and Mch4/FLICE2 being apical enzymes that initiate precipitous proteolytic processing of downstream caspases resulting in apoptosis (Boldin, M. P., et al., *Cell* 85:805–815 (1996); Srinivasula, S. M., et al., *PNAS* 93:14486–14491 (1996); Fernandes-Alnemri, T., et al., *PNAS* 93:7464–7469 (1996); Henkart, P. A., *Immunity* 4:195–201 (1996)). A number of viral gene products antagonize CD-95 and TNFR-1 mediated killing as a means to persist in the infected host (Shen, Y. and Shenk, T. S., *Current Opinion in Genetics and Development* 5:105–111 (1995)). The poxvirus encoded serpin CrmA and baculovirus gene product p35 are direct caspase inhibitors (Walker, N. P., et al., *Cell* 78:343–352 (1994)). In contrast, the molluscum contagiosum virus protein MC159 and the equine herpes virus protein E8 encode DED-containing decoy molecules that bind to either FADD (MC159) or FLICE (E8) and disrupt assembly of the receptor signaling complex, thereby abrogating the death signal (Hu, S., et al., *J. Biol. Chem.* 272:9621–9624 (1997); Bertin, J., et al., *PNAS* 94:1172–1176 (1997); Thome, M., et al., *Nature* 386:527–521 (1997)). The existence of these viral inhibitors has raised the question of whether functionally equivalent molecules are encoded in the mammalian genome.

There is a need for factors, such as the polypeptides of the present invention, that are useful for inhibiting apoptosis for therapeutic purposes, for example, in the treatment of Alzheimer's disease, Parkinson's disease, rheumatoid arthritis, septic shock, sepsis, stroke, CNS inflammation, osteoporosis, ischemia, reperfusion injury, cell death associated with cardiovascular disease, polycystic kidney disease, apoptosis of endothelial cells in cardiovascular disease, degenerative liver disease, MS and head injury damage. There is a need, therefore, for the identification and characterization of such factors that are inhibitors of apoptosis, such as the I-FLICE-1 and I-FLICE-2 polypeptides of the present invention, which can play a role in preventing, ameliorating or correcting the diseases and disorders associated with apoptosis.

SUMMARY OF THE INVENTION

The present invention provides isolated nucleic acid molecules comprising a polynucleotide encoding the I-FLICE-1 polypeptide having the amino acid sequence shown in SEQ ID NO:2 or the amino acid sequence encoded by the cDNA clone deposited in a bacterial host as ATCC® Deposit Number 209041 on May 15, 1997. The present invention provides isolated nucleic acid molecules comprising a polynucleotide encoding the I-FLICE-2 polypeptide having the amino acid sequence shown in SEQ ID NO:6 or the amino acid sequence encoded by the cDNA clone deposited in a bacterial host as ATCC® Deposit Number 209038 on May 15, 1997.

The present invention also relates to recombinant vectors, which include the isolated nucleic acid molecules of the present invention, and to host cells containing the recombinant vectors, as well as to methods of making such vectors and host cells and for using them for production of I-FLICE-1 or I-FLICE-2 polypeptides or peptides by recombinant techniques.

The invention further provides an isolated I-FLICE-1 or I-FLICE-2 polypeptides having an amino acid sequence encoded by the polynucleotides described herein.

The invention further provides a diagnostic method useful during diagnosis or prognosis of a disease states resulting from aberrant cell proliferation due to alterations in I-FLICE-1 or I-FLICE-2 expression.

The present invention also provides a screening method for determining whether a candidate agonist or antagonist is capable of enhancing or inhibiting a cellular activity of either an I-FLICE-1 or I-FLICE-2 polypeptide. The method involves contacting cells which express one or both of the I-FLICE-1 or I-FLICE-2 polypeptides with a candidate compound, assaying a cellular response, and comparing the cellular response to a standard cellular response, the standard being assayed in absence of the candidate compound, whereby an increased cellular response over the standard indicates that the candidate compound is an agonist of the polypeptide activity and a decreased cellular response compared to the standard indicates that the candidate compound is an antagonist of the activity.

An additional aspect of the invention is related to a method for treating an individual in need of an increased level of I-FLICE-1 or I-FLICE-2 activity in the body comprising administering to such an individual a composition comprising a therapeutically effective amount of an isolated I-FLICE-1 or I-FLICE-2 polypeptide of the invention or an agonist thereof.

A still further aspect of the invention is related to a method for treating an individual in need of a decreased level of I-FLICE-1 or I-FLICE-2 activity in the body comprising, administering to such an individual a composition comprising a therapeutically effective amount of an I-FLICE-1 or I-FLICE-2 antagonist.

BRIEF DESCRIPTION OF THE DRAWINGS

FIG. 1A–1B show the nucleotide (SEQ ID NO:1) and deduced amino acid (SEQ ID NO:2) sequences of I-FLICE-1 (HSLAZ11). The protein has 480 amino acid residues and a deduced molecular weight of about 55.3 kDa.

FIG. 2 shows the regions of similarity between the amino acid sequences of the I-FLICE-1, I-FLICE-2, FLICE (SEQ ID NO:3), and Mch4 (SEQ ID NO:4). Shading (with solid black) indicates residues that match the consensus sequence exactly.

FIGS. 4A–4C show the nucleotide (SEQ ID NO:5) and deduced amino acid (SEQ ID NO:6) sequences of I-FLICE-2 (HCEBJ50). The protein has 348 amino acid residues and a deduced molecular weight of about 39.2 kDa.

DETAILED DESCRIPTION

Figure 3:
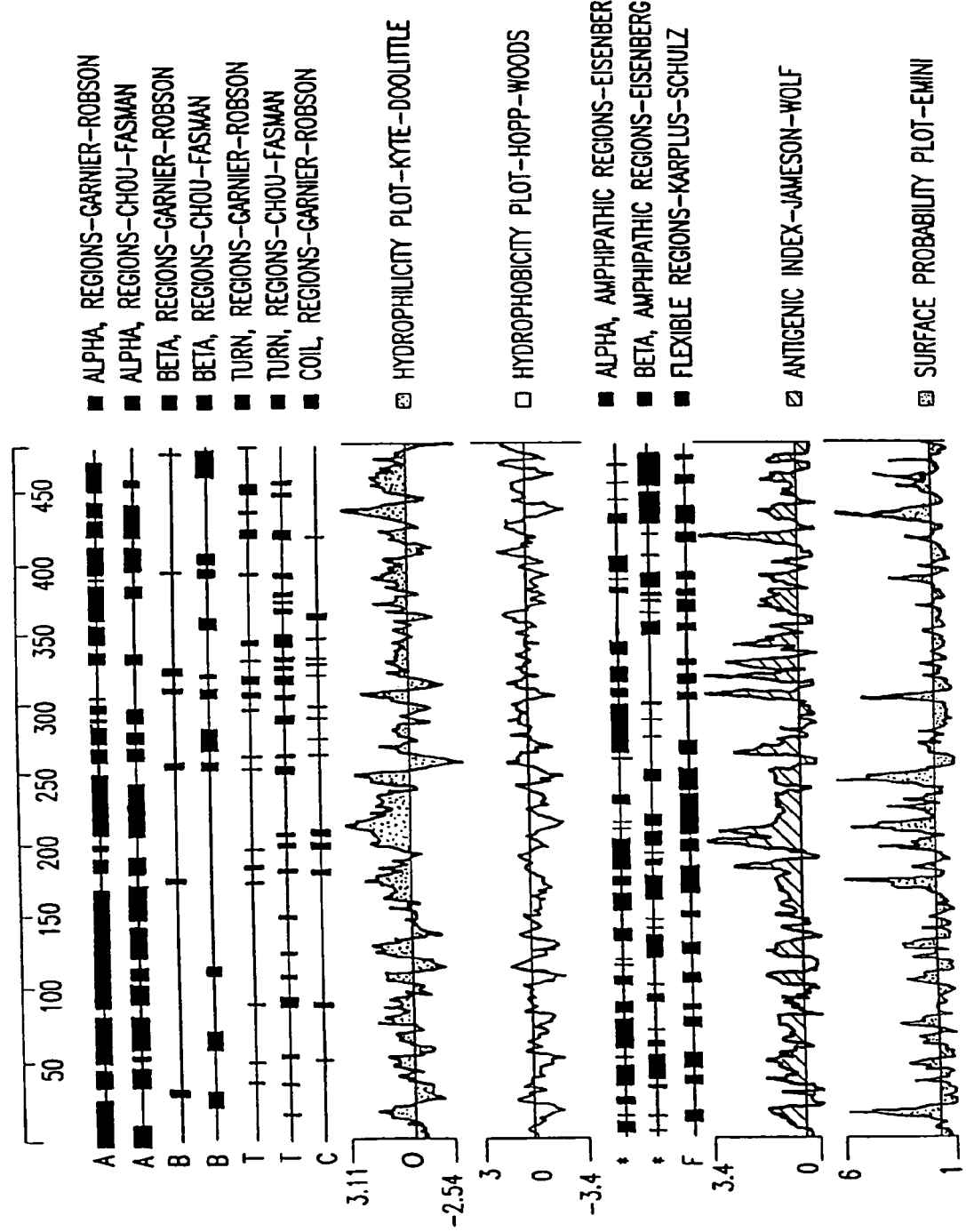
FIG. 3 shows an analysis of the I-FLICE-1 amino acid sequence. Alpha, beta, turn and coil regions; hydrophilicity and hydrophobicity; amphipathic regions; flexible regions; antigenic index and surface probability are shown. In the "Antigenic Index-Jameson-Wolf" graph, amino acid residues about 41 to about 92, about 155 to about 249, about 332 to about 447 in FIGS. 1A–1B (SEQ ID NO:2) correspond to the shown highly antigenic regions of the I-FLICE-1 protein.
Figure 5:
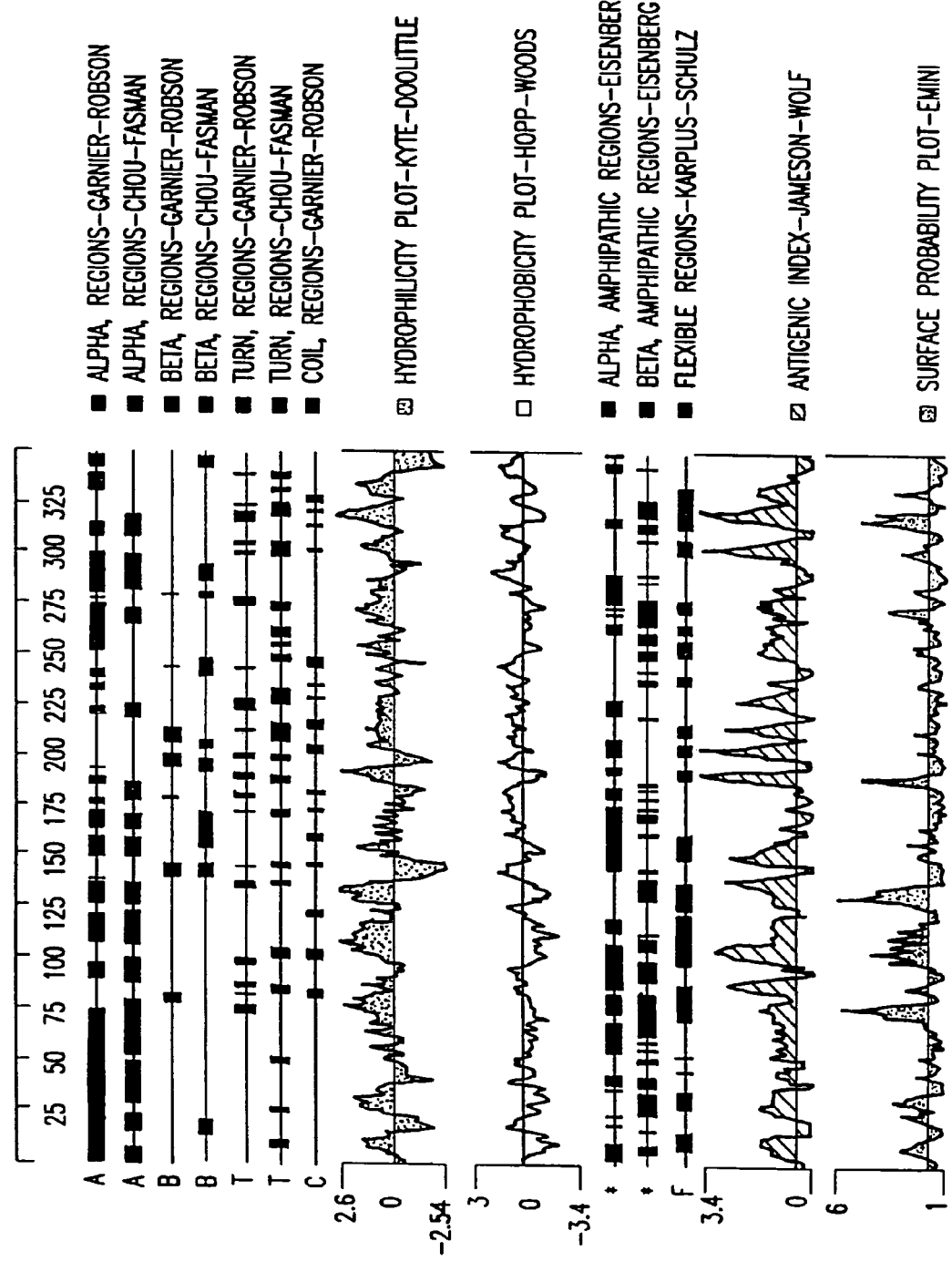
FIG. 5 shows an analysis of the I-FLICE-2 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 62 to about 136, about 184 to about 193, about 205 to about 341 in FIGS. 4A–4C (SEQ ID NO:6) correspond to the shown highly antigenic regions of the I-FLICE-2 protein.

The present invention provides isolated nucleic acid molecules comprising a polynucleotide encoding an I-FLICE-1 or I-FLICE-2 polypeptide having the amino acid sequence shown in SEQ ID NO:2 or SEQ ID NO:6, respectively, which was determined by sequencing a cloned cDNA. The I-FLICE-1 protein of the present invention shares sequence homology with FLICE and Mch4 (FIG. 2) (SEQ ID NOs:3 and 4). The nucleotide sequence shown in SEQ ID NO:1 was obtained by sequencing a cDNA clone (HSLAZ11), which was deposited on May 15, 1997 at the American Type Culture Collection (ATCC®), 10801 University Blvd., Manassas, Va. 20110–2209, USA (present address), and given accession number 209041. The deposited clone is inserted in the pBLUESCRIPT® SK(−) plasmid (Stratagene, La Jolla, Calif.) using the EcoRI and XhoI restriction endonuclease cleavage sites. The I-FLICE-2 protein of the present invention shares sequence homology with FLICE and Mch4 (FIG. 2 (SEQ ID NOs:3 and 4)). The nucleotide sequence shown in SEQ ID NO:5 was obtained by sequencing a cDNA clone (HCEBJ50), which was deposited on May 15, 1997 at the American Type Culture Collection (ATCC®), 10801 University Blvd., Manassas, Va. 20110–2209, USA (present address), and given accession number 209038. The deposited clone is inserted in the pBLUESCRIPT® SK(−) plasmid (Stratagene, La Jolla, Calif.) using the EcoRI and XhoI restriction endonuclease cleavage sites.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in SEQ ID NO:1 or SEQ ID NO:5, a nucleic acid molecule of the present invention encoding an I-FLICE-1 or I-FLICE-2 polypeptide may be obtained using standard cloning and screening procedures, such as those for cloning cDNAs using mRNA as starting material. Illustrative of the invention, the nucleic acid molecule described in SEQ ID NO:1 was discovered in a cDNA library derived from human umbilical vein endothelial cell. The gene was also identified in cDNA libraries from smooth muscle. The determined nucleotide sequence of the I-FLICE-1 cDNA of SEQ ID NO:1 contains an open reading frame encoding a protein of about 480 amino acid residues and a deduced molecular weight of about 55.3 kDa. The I-FLICE-1 protein shown in SEQ ID NO:2 is overall about 29% identical and about 54% similar to FLICE (FIG. 2 (SEQ ID NO:3)).

Also illustrative of the invention, the nucleic acid molecule described in SEQ ID NO:5 was discovered in a cDNA library derived from human umbilical vein endothelial cell. The gene was also identified in cDNA libraries from brain tissue isolated from the cerebellum. The determined nucleotide sequence of the I-FLICE-2 cDNA of SEQ ID NO:5 contains an open reading frame encoding a protein of about 348 amino acid residues and a deduced molecular weight of about 39 kDa. The I-FLICE-2 protein shown in SEQ ID NO:6 is overall about 28% identical and about 54% similar to FLICE (FIG. 2 (SEQ ID NO:3)).

In addition, I-FLICE-1 and I-FLICE-2 are nearly identical over the majority of their sequences; however, I-FLICE-1 has additional amino acids comprising the N-terminal region of the protein. The amino terminal domains of both I-FLICE-1 and I-FLICE-2 exhibit significant sequence similarity to the DED domain of the FADD protein (Hu, S. et al., *J. Biol. Chem.* 272:17255–17257 (1997); Irmler, M., et al., *Nature* 388:190–195 (1997)), the domain through which FLICE proteins and death receptors interact. The amino terminal domain of I-FLICE-2 consists of only a single DED/FADD homology domain (comprising amino acid residues from about 1 to about 75 in SEQ ID NO:6), while the additional amino acids found in the amino terminal domain of I-FLICE-1 appear to provide a second DED/FADD homology domain (comprising amino acid residues from about 1 to about 75 and amino acids residues from about 91 to about 171 in SEQ ID NO:2). The carboxy terminal domains of the both I-FLICE-1 and I-FLICE-2 also contain significant sequence similarity to the active subunit domains of the ICE/CED-3 family of cysteine proteases (amino acids residues from about 172 to about 375 and amino acid residues from about 376 to about 480 in SEQ ID NO:2; amino acids residues from about 76 to about 252 and amino acid residues from about 253 to about 348 in SEQ ID NO:6). Neither I-FLICE-1 or I-FLICE-2 contain the catalytic cysteine that is normally embedded in the conserved pentapeptide QACRG (SEQ ID NO:33) or QACQG (SEQ ID NO:34) motif present in all known caspases. Rather, both I-FLICE-1 and I-FLICE-2 have the pentapeptide sequence QNYVV (SEQ ID NO:35; amino acid residues from about 358 to about 362 in SEQ ID NO:2 and amino acid residues from about 244 to about 248 in SEQ ID NO:6). Further, only three of seven conserved residues that form the substrate binding pocket found in all caspases are present in I-FLICE-1 and I-FLICE-2. Given the lack of conservation of key residues involved in catalysis and substrate binding, it can be concluded that I-FLICE-1 and I-FLICE-2 are not cysteine proteases and are incapable of substrate binding, thus, providing these proteins with a dominant negative inhibitory function. I-FLICE-1 and I-FLICE-2 are the first examples of catalytically inert caspases that can inhibit apoptosis.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in SEQ ID NO:1 or SEQ ID NO:5; DNA molecules comprising the coding sequence for the I-FLICE-1 or I-FLICE-2 protein; and DNA molecules which comprise a sequence substantially different from those described above but which, due to the degeneracy of the genetic code, still encode the I-FLICE-1 or I-FLICE-2 protein. Of course, the genetic code is well known in the art. Thus, it would be routine for one skilled in the art to generate such degenerate variants.

In addition, the invention provides nucleic acid molecules having nucleotide sequences related to extensive portions of SEQ ID NO:1 which have been determined from the following related cDNA clones: HOSBY07R (SEQ ID NO:23), HSAVA13R (SEQ ID NO:24), HLFBD88R (SEQ ID NO:25), HOSAH65R (SEQ ID NO:26), HUVBS23R (SEQ ID NO:27), HHFFJ01RA (SEQ ID NO:28), HUVBL22R (SEQ ID NO:29), and HUVBX15R (SEQ ID NO:30).

The invention also provides nucleic acid molecules having nucleotide sequences related to extensive portions of SEQ ID NO:5 (I-FLICE-2) which have been determined from the following related cDNA clones: HTNBE58R (SEQ ID NO:31), HTPBE58R (SEQ ID NO:32), HOSBY07R (SEQ ID NO:23), HSAVA13R (SEQ ID NO:24), HLFBD88R (SEQ ID NO:25), HOSAH65R (SEQ ID NO:26), and HHFFJ01RA (SEQ ID NO:28).

In another aspect, the invention provides isolated nucleic acid molecules encoding the I-FLICE-1 polypeptide having an amino acid sequence as encoded by the cDNA clone contained in the plasmid deposited as ATCC® Deposit No. 209041 on May 15, 1997. The invention also provides isolated nucleic acid molecules encoding the I-FLICE-2 polypeptide having an amino acid sequence as encoded by the cDNA clone contained in the plasmid deposited as ATCC® Deposit No. 209038 on May 15, 1997. In a further embodiment, nucleic acid molecules are provided encoding the I-FLICE-1 or I-FLICE-2 polypeptide or the full-length I-FLICE polypeptide lacking the N-terminal methionine. The invention also provides an isolated nucleic acid molecule having the nucleotide sequence shown in SEQ ID NO:1 or SEQ ID NO:5 or the nucleotide sequence of the I-FLICE-1 or I-FLICE-2 cDNA contained in the above-described deposited clones, or a nucleic acid molecule having a sequence complementary to one of the above sequences. Such isolated molecules, particularly DNA molecules, are useful as probes for gene mapping, by in situ hybridization with chromosomes, and for detecting expression of the I-FLICE-1 or I-FLICE-2 gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 or SEQ ID NO:5 is intended fragments at least about 15 nt, and more preferably at least about 20 nt, still more preferably at least about 30 nt, and even more preferably, at least about 40 nt in length which are useful as diagnostic probes and primers as discussed herein. Of course larger DNA fragments 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, or 2016 nt in length of the sequence shown in SEQ ID NO:1 are also useful according to the present invention as are fragments corresponding to most, if not all, of the nucleotide sequence of the cDNA clone contained in the plasmid deposited as ATCC® Deposit No. 209041 or as shown in SEQ ID NO:1. Similarly, larger DNA fragments 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, or 2547 nt in length of the sequence shown in SEQ ID NO:5 are also useful according to the present invention as are fragments corresponding to most, if not all, of the nucleotide sequence of the cDNA clone contained in the plasmid deposited as ATCC® Deposit No. 209038 or as shown in SEQ ID NO:5. By a fragment at least 20 nt in length, for example, is intended fragments which include 20 or more contiguous bases from the nucleotide sequence of the deposited cDNA or the nucleotide sequence as shown in SEQ ID NO:1 or SEQ ID NO:5.

In a more specific embodiment, the nucleic acid molecules of the present invention do not include the sequences, nucleic acid molecules (e.g., clones), or nucleic acid inserts identified in one or more of the following GenBank Accession Reports: AA001257, AA151642, AA149562, C05730, AA565691, AA467756, D83882, AA002262, AA115793, AA467995, AA115792, AA467938, W60406, AA358042, AA468056, W23795, AA358043, T93307, AA453850, AA379905, AA296229, H15978, AA501289, AA296309, AA296174, T30922, T48754, AA453766, C05795, AA198928, N94588, H15052, Z42895, F13176, W52946, AA558404, AA070614, AA613966, AA525331, AA663074, AA135811, AA526099, AA302978, H68343, AA610255, AA229005, T05118, T30864, AA302968, or AA364006, all of which are incorporated herein by reference.

Preferred nucleic acid fragments of the present invention include nucleic acid molecules encoding epitope-bearing portions of the I-FLICE-1 protein. In particular, such nucleic acid fragments of the present invention include nucleic acid molecules encoding: a polypeptide comprising amino acid residues from about 41 to about 92 in SEQ ID NO:2; a polypeptide comprising amino acid residues from about 155 to about 249 in SEQ ID NO:2; a polypeptide comprising amino acid residues from about 332 to about 474 in SEQ ID NO:2. The inventors have determined that the above polypeptide fragments are antigenic regions of the I-FLICE-1 protein. Methods for determining other such epitope-bearing portions of the I-FLICE-1 protein are described in detail below.

Preferred nucleic acid fragments of the present invention include nucleic acid molecules encoding epitope-bearing portions of the I-FLICE-2 protein. In particular, such nucleic acid fragments of the present invention include nucleic acid molecules encoding: a polypeptide comprising amino acid residues from about 62 to about 136 in SEQ ID NO:6; a polypeptide comprising amino acid residues from about 184 to about 193 in SEQ ID NO:6; a polypeptide comprising amino acid residues from about 205 to about 341 in SEQ ID NO:6. The inventors have determined that the above polypeptide fragments are antigenic regions of the I-FLICE-2 protein. Methods for determining other such epitope-bearing portions of the I-FLICE-2 protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clones contained in ATCC® Deposit 209041 or ATCC® Deposit 209038. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNAs or the nucleotide sequence as shown in SEQ ID NO:1 or SEQ ID NO:5). Of course, a polynucleotide which hybridizes only to a poly A sequence (such as the 3' terminal poly(A) tract of the I-FLICE-1 cDNA shown in SEQ ID NO:1 or the I-FLICE-2 cDNA shown in SEQ ID NO:5), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode an I-FLICE-1 or I-FLICE-2 polypeptide may include, but are not limited to those encoding the amino acid sequence of the polypeptide, by itself; the coding sequence for the mature polypeptide and additional sequences, such as those encoding a secretory sequence, such as a pre-, or pro- or prepro- protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example— ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778 (1984). As discussed below, other such fusion proteins include the I-FLICE-1 or I-FLICE-2 fused to Fc at the N- or C-terminus.

The present invention further relates to variants of the nucleic acid molecules of the present invention, which encode portions, analogs or derivatives of the I-FLICE-1 or I-FLICE-2 protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the I-FLICE-1 or I-FLICE-2 protein or portions thereof. Also especially preferred in this regard are conservative substitutions.

Further embodiments of the invention include isolated nucleic acid molecules comprising a polynucleotide having a nucleotide sequence at least 95%, 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence encoded by the cDNA clone contained in ATCC® Deposit No. 209041; or (d) a nucleotide sequence complementary to any of the nucleotide sequences in (a), (b), or (c).

Further embodiments of the invention include isolated nucleic acid molecules comprising a polynucleotide having a nucleotide sequence at least 95%, 96%, 97%, 98% or 99% identical to (a) a nucleotide sequence encoding the polypeptide having the amino acid sequence in SEQ ID NO:6; (b) a nucleotide sequence encoding the polypeptide having the amino acid sequence in SEQ ID NO:6, but lacking the N-terminal methionine; (c) a nucleotide sequence encoding the polypeptide having the amino acid sequence encoded by the cDNA clone contained in ATCC® Deposit No. 209038; or (d) a nucleotide sequence complementary to any of the nucleotide sequences in (a), (b), or (c).

Additional embodiments of the invention include isolated nucleic acid molecules comprising a polynucleotide having a nucleotide sequence at least 95%, 96%, 97%, 98% or 99% identical to (a) a nucleotide sequence encoding a polypeptide comprising amino acids from about 1 to about 75 in SEQ ID NO:2; (b) a nucleotide sequence encoding a polypeptide comprising amino acids from about 91 to about 171 in SEQ ID NO:2; (c) a nucleotide sequence encoding a polypeptide comprising amino acids from about 172 to about 375 in SEQ ID NO:2; (d) a nucleotide sequence encoding a polypeptide comprising amino acids from about 376 to about 480 in SEQ ID NO:2; (e) a nucleotide sequence encoding a polypeptide comprising amino acids from about 1 to about 75 in SEQ ID NO:6; (f) a nucleotide sequence encoding a polypeptide comprising amino acids from about 76 to about 252 in SEQ ID NO:6; (g) a nucleotide sequence encoding a polypeptide comprising amino acids from about 253 to about 348 in SEQ ID NO:6; (h) or a nucleotide sequence complementary to any of the nucleotide sequences in (a), (b), (c), (d), (e), (f), or (g).

By a polynucleotide having a nucleotide sequence at least, for example, 95% "identical" to a reference nucleotide sequence encoding an I-FLICE polypeptide is intended that the nucleotide sequence of the polynucleotide is identical to the reference sequence except that the polynucleotide sequence may include up to five point mutations per each 100 nucleotides of the reference nucleotide sequence encoding an I-FLICE polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO:1 or SEQ ID NO:5 or to the nucleotides sequence of the deposited cDNA clone can be determined conventionally using known computer programs such as the BESTFIT® program (Wisconsin Sequence Analysis Package, Version 8 for Unix, Genetics Computer Group, University Research Park, 575 Science Drive, Madison, Wis. 53711). BESTFIT® uses the local homology algorithm of Smith and Waterman, *Advances in Applied Mathematics* 2:482–489 (1981), to find the best segment of homology between two sequences. When using BESTFIT® or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in SEQ ID NO:1 or SEQ ID NO:5 or to the nucleic acid sequence of the deposited cDNAs, irrespective of whether they encode a polypeptide having I-FLICE activity. This is because even where a particular nucleic acid molecule does not encode a polypeptide having I-FLICE activity, one of skill in the art would still know how to use the nucleic acid molecule, for instance, as a hybridization probe or a polymerase chain reaction (PCR) primer. Uses of the nucleic acid molecules of the present invention that do not encode a polypeptide having I-FLICE activity include, inter alia, (1) isolating the I-FLICE-1 or I-FLICE-2 gene or allelic variants thereof in a cDNA library; (2) in situ hybridization (e.g., "FISH") to metaphase chromosomal spreads to provide precise chromosomal location of the I-FLICE-1 or I-FLICE-2 gene, as described in Verma et al., *Human Chromosomes: A Manual of Basic Techniques*, Pergamon Press, New York (1988); and (3) Northern Blot analysis for detecting I-FLICE-1 or I-FLICE-2 mRNA expression in specific tissues.

Preferred, however, are nucleic acid molecules having sequences at least 95%, 96%, 97%, 98% or 99% identical to a nucleic acid sequence shown in SEQ ID NO:1 or SEQ ID NO:5 or to a nucleic acid sequence of the deposited cDNA which do, in fact, encode a polypeptide having I-FLICE protein activity. By "a polypeptide having I-FLICE activity" is intended polypeptides exhibiting I-FLICE-1 or I-FLICE-2 activity in a particular biological assay. For example, I-FLICE-1 or I-FLICE-2 protein activity can be measured using the cell death assay as described in Example 6.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence of the deposited cDNA or a nucleic acid sequence shown in SEQ ID NO:1 or SEQ ID NO:5 will encode "a polypeptide having I-FLICE activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having I-FLICE activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of I-FLICE-1 or I-FLICE-2 polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, PHAGESCRIPT™ vectors, BLUESCRIPT® vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The I-FLICE-1 or I-FLICE-2 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

I-FLICE-1 and I-FLICE-2 Polypeptides and Fragments

The invention further provides an isolated I-FLICE-1 or I-FLICE-2 polypeptide having the amino acid sequence encoded by the deposited cDNAs, or the amino acid sequence in SEQ ID NO:2 or SEQ ID NO:6, or a peptide or polypeptide comprising a portion of the above polypeptides.

It will be recognized in the art that some amino acid sequences of the I-FLICE-1 or I-FLICE-2 polypeptide can be varied without significant effect of the structure or function of the protein. If such differences in sequence are contemplated, it should be remembered that there will be critical areas on the protein which determine activity.

Thus, the invention further includes variations of the I-FLICE-1 or I-FLICE-2 polypeptide which show substantial I-FLICE-1 or I-FLICE-2 polypeptide activity or which include regions of I-FLICE-1 or I-FLICE-2 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2 or SEQ ID NO:6, or that encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the I-FLICE-1 or I-FLICE-2 protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the I-FLICE-1 or I-FLICE-2 of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above and below. Generally speaking, the number of substitutions for any given I-FLICE-1 or I-FLICE-2 polypeptide, or mutant thereof, will not be more than 50, 40, 30, 20, 10, 5, or 3, depending on the objective.

Amino acids in the I-FLICE-1 or I-FLICE-2 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. Sites that are critical for ligand interactions can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the I-FLICE-1 or I-FLICE-2 polypeptide can be substantially purified by the one-step method described in Smith and Johnson, *Gene* 67:31–40 (1988).

The polypeptides of the present invention include the polypeptide encoded by the deposited cDNA; a polypeptide comprising amino acids about 1 to about 480 in SEQ ID NO:2; a polypeptide comprising amino acids about 2 to about 480 in SEQ ID NO:2; as well as polypeptides which are at least 95% identical, still more preferably at least 96%, 97%, 98% or 99% identical to those described above and also include portions of such polypeptides with at least 30 amino acids and more preferably at least 50 amino acids.

The polypeptides of the present invention also include the polypeptide encoded by the deposited cDNA; a polypeptide comprising amino acids about 1 to about 348 in SEQ ID NO:6; a polypeptide comprising amino acids about 2 to about 348 in SEQ ID NO:6; as well as polypeptides which are at least 95% identical, still more preferably at least 96%, 97%, 98% or 99% identical to those described above and also include portions of such polypeptides with at least 30 amino acids and more preferably at least 50 amino acids.

The polypeptides of the present invention further include the polypeptide comprising amino acids from about 1 to about 75 in SEQ ID NO:2; amino acids from about 91 to about 171 in SEQ ID NO:2; amino acids from about 172 to about 375 in SEQ ID NO:2; amino acids from about 376 to about 480 in SEQ ID NO:2; amino acids from about 1 to about 75 in SEQ ID NO:6; amino acids from about 76 to about 252 in SEQ ID NO:6; amino acids from about 253 to about 348 in SEQ ID NO:6; as well as polypeptides which are at least 95% identical, still more preferably at least 96%, 97%, 98% or 99% identical to those described above and also include portions of such polypeptides with at least 30 amino acids and more preferably at least 50 amino acids.

By a polypeptide having an amino acid sequence at least, for example, 95% "identical" to a reference amino acid sequence of an I-FLICE-1 or I-FLICE-2 polypeptide is intended that the amino acid sequence of the polypeptide is identical to the reference sequence except that the polypeptide sequence may include up to five amino acid alterations per each 100 amino acids of the reference amino acid of the I-FLICE-1 or I-FLICE-2 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2 or SEQ ID NO:6 or to the amino acid sequence encoded by deposited cDNA clones can be determined conventionally using known computer programs such the BESTFIT® program (Wisconsin Sequence Analysis Package, Version 8 for Unix, Genetics Computer Group, University Research Park, 575 Science Drive, Madison, Wis. 53711). When using BESTFIT® or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention are useful as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Lerner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of a polypeptide of the invention. Non-limiting examples of antigenic polypeptides or peptides that can be used to generate I-FLICE-1-specific antibodies include: a polypeptide comprising amino acid residues from about 41 to about 92 in SEQ ID NO:2; a polypeptide comprising amino acid residues from about 155 to about 249 in SEQ ID NO:2; a polypeptide comprising amino acid residues from about 332 to about 474 in SEQ ID NO:2. As indicated above, the inventors have determined that the above polypeptide fragments are antigenic regions of the I-FLICE-1 protein.

Non-limiting examples of antigenic polypeptides or peptides that can be used to generate I-FLICE-2-specific antibodies include: a polypeptide comprising amino acid residues from about 62 to about 136 in SEQ ID NO:6; a polypeptide comprising amino acid residues from about 184 to about 193 in SEQ ID NO:6; a polypeptide comprising amino acid residues from about 205 to about 341 in SEQ ID NO:6. The inventors have determined that the above polypeptide fragments are antigenic regions of the I-FLICE-2 protein.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986).

As one of skill in the art will appreciate, I-FLICE-1 or I-FLICE-2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331: 84–86 (1988)). Fusion proteins that have a disulfide-linked dimeric structure due to the IgG part can also be more efficient in binding and neutralizing other molecules than the monomeric I-FLICE-1 or I-FLICE-2 protein or protein fragment alone (Fountoulakis et al., *J. Biochem* 270:3958–3964 (1995)).

Disease Diagnosis and Prognosis

It is believed that certain tissues in mammals with specific disease states associated with aberrant cell survival express significantly altered levels of I-FLICE-1 or I-FLICE-2 and mRNA encoding I-FLICE-1 or I-FLICE-2 when compared to a corresponding "standard" mammal, i.e., a mammal of the same species not having the disease state. Thus, the present invention is useful for detecting such states in mammals. Preferred mammals include monkeys, apes, cats, dogs, cows, pigs, horses, rabbits and humans. Particularly preferred are humans.

It is further believed that enhanced levels of I-FLICE-1 or I-FLICE-2 can be detected in certain body fluids (e.g., sera, plasma, urine, and spinal fluid) from mammals with the disease state when compared to analogous fluids from mammals of the same species not having the disease state. Thus, the invention provides a diagnostic method useful during diagnosis of disease states, which involves assaying the expression level of the gene encoding I-FLICE-1 or I-FLICE-2 in mammalian cells or body fluid and comparing the gene expression level with a standard I-FLICE-1 or I-FLICE-2, whereby an increase or decrease in the gene expression level over the standard is indicative of certain disease states associated with aberrant cell survival.

Where diagnosis of a disease state involving I-FLICE-1 or I-FLICE-2 of the present invention has already been made according to conventional methods, the present invention is useful as a prognostic indicator, whereby patients exhibiting significantly aberrant I-FLICE-1 or I-FLICE-2 gene expression levels will experience a worse clinical outcome relative to patients expressing the gene at a lower level.

By "assaying the expression level of the gene encoding I-FLICE-1 or I-FLICE-2" is intended qualitatively or quantitatively measuring or estimating the level of I-FLICE-1 or I-FLICE-2 protein or the level of the mRNA encoding I-FLICE-1 or I-FLICE-2 protein in a first biological sample either directly (e.g., by determining or estimating absolute protein level or mRNA level) or relatively (e.g., by comparing to the I-FLICE-1 or I-FLICE-2 protein level or mRNA level in a second biological sample).

Preferably, the I-FLICE-1 or I-FLICE-2 protein level or mRNA level in the first biological sample is measured or estimated and compared to a standard I-FLICE-1 or I-FLICE-2 protein level or mRNA level, the standard being taken from a second biological sample obtained from an individual not having the disease state. As will be appreciated in the art, once a standard I-FLICE-1 or I-FLICE-2 protein level or mRNA level is known, it can be used repeatedly as a standard for comparison.

By "biological sample" is intended any biological sample obtained from an individual, cell line, tissue culture, or other source which contains I-FLICE-1 or I-FLICE-2 protein or mRNA. Biological samples include mammalian body fluids (such as sera, plasma, urine, synovial fluid and spinal fluid) which contain I-FLICE-1 or I-FLICE-2 protein, and ovarian, prostate, heart, placenta, pancreas liver, spleen, lung, breast, umbilical tissue, and other tissues. Methods for obtaining tissue biopsies and body fluids from mammals are well known in the art. Where the biological sample is to include mRNA, a tissue biopsy is the preferred source.

Diseases associated with increased cell survival, or the inhibition of apoptosis, include cancers (such as follicular lymphomas, carcinomas with p53 mutations, hormone-dependent tumors, and cancers of the breast, ovary, prostate, bone, liver, lung, pancreas, and spleen); autoimmune disorders (such as systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. Diseases associated with decreased cell survival, or increased apoptosis, include Alzheimer's disease, Parkinson's disease, rheumatoid arthritis, septic shock, sepsis, stroke, CNS inflammation, osteoporosis, ischemia, reperfusion injury, cell death associated with cardiovascular disease, polycystic kidney disease, apoptosis of endothelial cells in cardiovascular disease, degenerative liver disease, MS and head injury damage.

Assays available to detect levels of proteins are well known to those of skill in the art, for example, radioimmunoassays, competitive-binding assays, Western blot analysis, and preferably an ELISA assay may be employed.

I-FLICE-1 or I-FLICE-2 specific antibodies can be raised against the intact I-FLICE-1 or I-FLICE-2 protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (mAb) is meant to include intact molecules as well as antibody fragments (such as, for example, Fab and F(ab')$_2$ fragments) which are capable of specifically binding to the I-FLICE-1 or I-FLICE-2 protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the I-FLICE-1 or I-FLICE-2 protein or an antigenic fragment thereof can be administered to an animal in order to induce the production of sera containing polyclonal antibodies. In a preferred method, a preparation of I-FLICE-1 or I-FLICE-2 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or I-FLICE-1 or I-FLICE-2 protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., (1981) pp. 563–681).

Assaying I-FLICE-1 or I-FLICE-2 protein levels in a biological sample can occur using antibody-based techniques. For example, I-FLICE-1 or I-FLICE-2 protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)).

As noted above, other antibody-based methods useful for detecting I-FLICE-1 or I-FLICE-2 protein gene expression include immunoassays, such as the enzyme linked immunosorbent assay (ELISA) and the radioimmunoassay (RIA).

Suitable labels are known in the art and include enzyme labels, such as, Glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

Total cellular RNA can be isolated from a biological sample using the single-step guanidinium-thiocyanate-phenol-chloroform method described in Chomczynski and Sacchi, *Anal. Biochem.* 162:156–159 (1987). Levels of mRNA encoding the I-FLICE-1 or I-FLICE-2 protein are then assayed using any appropriate method. These include Northern blot analysis (Harada et al., *Cell* 63:303–312 (1990)), S1 nuclease mapping (Fujita et al., *Cell* 49:357–367 (1987)), the polymerase chain reaction (PCR), reverse transcription in combination with the polymerase chain reaction (RT-PCR) (Makino et al., *Technique* 2:295–301 (1990)), and reverse transcription in combination with the ligase chain reaction (RT-LCR).

Agonists and Antagonists—Assays and Molecules

The invention also provides a method of screening compounds to identify agonists and antagonists of I-FLICE-1 or I-FLICE-2. By "agonist" is intended naturally occurring and synthetic compounds capable of enhancing one or more activity mediated by I-FLICE-1 or I-FLICE-2 polypeptides. By "antagonist" is intended naturally occurring and synthetic compounds capable of inhibiting one or more activity mediated by I-FLICE-1 or I-FLICE-2 polypeptides.

Thus, in a further aspect, a screening method is provided for determining whether a candidate agonist or antagonist is capable of enhancing or inhibiting a cellular activity of either an I-FLICE-1 or I-FLICE-2 polypeptide. The method involves contacting cells which express one or both of the I-FLICE-1 or I-FLICE-2 polypeptides with a candidate compound, assaying a cellular response, and comparing the cellular response to a standard cellular response, the standard being assayed in absence of the candidate compound, whereby an increased cellular response over the standard indicates that the candidate compound is an agonist of the polypeptide activity and a decreased cellular response compared to the standard indicates that the candidate compound is an antagonist of the activity. By "assaying a cellular response" is intended qualitatively or quantitatively measuring a cellular response in the presence of a candidate compound and either an I-FLICE-1 or I-FLICE-2 polypeptide (e.g., decreased or increased TNFR-1 or CD-95 induced apoptosis, binding of I-FLICE-1 or I-FLICE-2 to natural cellular ligands such as FLICE and Mch4/FLICE2).

Potential antagonists include small organic molecules amino acid sequences which bind to I-FLICE-1 or I-FLICE-2, fragments of I-FLICE-1 and I-FLICE-2, as well as anti-I-FLICE-1 and anti-I-FLICE-2 antibodies. Fragments of I-FLICE-1 and I-FLICE-2, which may be naturally occurring or synthetic, antagonize I-FLICE-1 and I-FLICE-2 polypeptide mediated activities by competing for binding to natural cellular ligands. Small organic molecules can antagonize I-FLICE-1 and I-FLICE-2 polypeptide mediated activities by binding either competitively or non-competitively to I-FLICE-1 or I-FLICE-2 or a cellular ligand of these proteins. Examples of small molecules include but are not limited to nucleotide sequences and small peptides or peptide-like molecules. Such molecules may be produced and screened for activity by a variety of methods (e.g., Light and Lerner, *Bioorganic & Medicinal Chemistry* 3(7):955–967 (1995); Cheng et al., *Gene* 171:1–8 (1996); Gates et al., *J. Mol. Biol.* 255:373–386 (1996)).

Similarly, potential agonists also include fragments of the polypeptides of the present invention, as well as anti-I-FLICE-1 and anti-I-FLICE-2 antibodies. Fragments of these proteins can act as agonists of I-FLICE-1 and I-FLICE-2 polypeptide mediated activities by binding to natural cellular ligands and inducing activities associated with the full-length protein. Agonists and antagonists of the present invention also include amino acid sequences having 95% or more identity to those shown in SEQ ID NOs:2 and 6, or fragments thereof.

Other potential antagonists include antisense oligonucleotides and oligonucleotides capable of forming triple helices with the sequences shown in SEQ ID NOs:1 and 5. Once a gene sequence is known, antisense and triple helix technologies can be used to regulate gene expression. Okano, *J. Neurochem.* 56:560 (1991); OLIGONUCLEOTIDES AS INHIBITORS OF GENE EXPRESSION, CRC Press, Boca Raton, Fla. (1988); Dervan et al., *Science* 251:1360 (1991); Cooney et al., *Science* 241:456 (1988); Lee et al., *Nucl. Acids Res.* 6:3073 (1979). In regards to antisense technology, for example, an oligonucleotide may be designed which is complementary to a portion of the I-FLICE-1 or I-FLICE-2 DNA sequences which is transcribed into RNA. This oligonucleotide may be delivered to cells in a number of forms, including as antisense RNA or incorporated into an expression vector. If incorporated into an expression vector, the oligonucleotide is generally orientated in a manner that an RNA molecule is produced upon in vivo expression which is complementary to that of the I-FLICE-1 or I-FLICE-2 mRNA sequence. The expressed antisense RNA molecule will hybridize to I-FLICE-1 or I-FLICE-2 mRNA and block translation in vivo.

The experiments set forth in Example 5 demonstrate that I-FLICE-1 binds to both FLICE and Mch4/FLICE2. Immunoprecipitation assays similar to that described in Example 5 can be used to identify additional molecules which bind to I-FLICE-1 and I-FLICE-2. Such binding molecules are candidate antagonists and agonists.

Example 6 sets forth a cell death assay used to demonstrate that overexpression of I-FLICE-1 results in the inhibition of TNFR-1 and CD-95 induced cell death. This assay can also be used to screen for compounds having agonistic and antagonistic activity directed to I-FLICE-1 and I-FLICE-2. Such a screening method is used to determine whether the compound increases or decreases TNFR-1 and CD-95 induced cell death in the presence of I-FLICE-1 or I-FLICE-2 either individually or in combination.

Proteins and other compounds which bind the I-FLICE-1 or I-FLICE-2 polypeptide domains are also candidate agonists and antagonists according to the present invention. Such binding compounds can be "captured" using the yeast two-hybrid system (Fields and Song, *Nature* 340:245–246 (1989); Gyuris et al., *Cell* 75:791–803 (1993); Zervos et al., *Cell* 72:223–232 (1993)).

The agonists may be employed for instance to enhance the action of I-FLICE-1 or I-FLICE-2 polypeptides, for example, in the treatment of Alzheimer's disease, Parkinson's disease, rheumatoid arthritis, septic shock, sepsis, stroke, CNS inflammation, osteoporosis, ischemia, reperfusion injury, cell death associated with cardiovascular disease, polycystic kidney disease, apoptosis of endothelial cells in cardiovascular disease, degenerative liver disease, MS and head injury damage.

The antagonists may be employed for instance to inhibit the action of I-FLICE-1 or I-FLICE-2 polypeptides, for example, in the treatment of cancers (such as follicular lymphomas, carcinomas with p53 mutations, hormone-dependent tumors, and cancers of the breast, ovary, prostate, bone, liver, lung, pancreas, and spleen); autoimmune disorders (such as systemic lupus erythematosus and immune-related glomerulonephritis rheumatoid arthritis) and viral infections (such as herpes viruses, pox viruses and adenoviruses), information graft v. host disease, acute graft rejection, and chronic graft rejection.

The agonists and antagonists may be employed in a composition with a pharmaceutically acceptable carrier, e.g., as hereinafter described.

Therapeutics

The novel mammalian inhibitors designated I-FLICE-1 and I-FLICE-2 (for inhibitor of FLICE) of the present invention, are catalytically inactive structural homologues of FLICE and Mch4/FLICE2 that inhibit both TNFR-1 and CD-95 induced apoptosis. These are the first examples of a naturally occurring catalytically inactive caspase that can act as a dominant negative inhibitor of apoptosis. The polypeptides of the present invention are useful for inhibiting apoptosis for therapeutic purposes, for example, in the treatment of Alzheimer's disease, Parkinson's disease, rheumatoid arthritis, septic shock, sepsis, stroke, CNS inflammation, osteoporosis, ischemia, reperfusion injury, cell death associated with cardiovascular disease, polycystic kidney disease, apoptosis of endothelial cells in cardiovascular disease, degenerative liver disease, MS and head injury damage.

Modes of Administration

It will be appreciated that conditions caused by a decrease in the standard or normal level of I-FLICE-1 or I-FLICE-2 activity in an individual, can be treated by administration of I-FLICE-1 or I-FLICE-2 protein. Thus, the invention further provides a method of treating an individual in need of an increased level of I-FLICE-1 or I-FLICE-2 activity comprising administering to such an individual a pharmaceutical composition comprising an effective amount of an isolated I-FLICE-1 or I-FLICE-2 polypeptide of the invention, particularly a mature form of the I-FLICE-1 or I-FLICE-2, effective to increase the I-FLICE-1 or I-FLICE-2 activity level in such an individual.

As a general proposition, the total pharmaceutically effective amount of I-FLICE-1 or I-FLICE-2 polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the I-FLICE-1 or I-FLICE-2 polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed.

Pharmaceutical compositions containing the I-FLICE-1 or I-FLICE-2 of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of an I-FLICE-1 or I-FLICE-2 protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian*

Inheritance In Man, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1(a)

Expression and Purification of I-FLICE-1 in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6xHis tag") covalently linked to the carboxyl terminus of that polypeptide.

The DNA sequence encoding the desired portion I-FLICE-1 protein is amplified from the deposited cDNA clone using PCR oligonucleotide primers which anneal to the amino terminal sequences of the desired portion of the I-FLICE-1 protein and to sequences in the deposited construct 3' to the cDNA coding sequence. Additional nucleotides containing restriction sites to facilitate cloning in the pQE60 vector are added to the 5' and 3' sequences, respectively.

For cloning the protein, the 5' primer has the sequence: 5' CGC<u>CCATGG</u>CTGAAGTCATCCATCAG 3' (SEQ ID NO:7) containing the underlined NcoI restriction site followed by 16 (i.e., 275–291) nucleotides complementary to the amino terminal coding sequence of the I-FLICE-1 sequence in FIGS. 1A–1B (SEQ ID NO:1). One of ordinary skill in the art would appreciate, of course, that the point in the protein coding sequence where the 5' primer begins may be varied to amplify a DNA segment encoding any desired portion of the complete protein in a shorter or longer form. The 3' primer has the sequence: 5'CGC<u>AAGCTT</u>GTGCTGGGATTACAGGTG 3' (SEQ ID NO:8) containing the underlined HindIII restriction site followed by 18 (i.e., 1740–1758) nucleotides complementary to the 3' end of the coding sequence immediately before the stop codon in the I-FLICE-1 DNA sequence in FIGS. 1A–1B (SEQ ID NO:1), with the coding sequence aligned with the restriction site so as to maintain its reading frame with that of the six His codons in the pQE60 vector.

The amplified I-FLICE-1 DNA fragment and the vector pQE60 are digested with NcoI/HindIII and the digested DNAs are then ligated together. Insertion of the I-FLICE-1 DNA into the restricted pQE60 vector places the I-FLICE-1 protein coding region downstream from the IPTG-inducible promoter and in-frame with an initiating AUG and the six histidine codons.

The ligation mixture is transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan$^r$"), is used in carrying out the illustrative example described herein. This strain, which is only one of many that are suitable for expressing I-FLICE-1 protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the I-FLICE-1 is loaded onto a nickel-nitrilo-tri-acetic acid ("NiNTA") affinity resin column (available from QIAGEN, Inc., supra). Proteins with a 6xHis tag bind to the NI-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH8, the column is first washed with 10 volumes of 6 M guanidine-HCl, pH8, then washed with 10 volumes of 6 M guanidine-HCl pH6, and finally the I-FLICE-1 is eluted with 6 M guanidine-HCl, pH5.

The purified protein is then renatured by dialyzing it against phosphate buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM imidazole. Imidazole is removed by a final dialyzing step against PBS or 50 mM sodium acetate pH6 buffer plus 200 mM NaCl. The purified protein is stored at 4° C. or frozen at −80° C.

Example 1(b)

Expression and Purification of I-FLICE-2 in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the carboxyl terminus of that polypeptide.

The DNA sequence encoding the desired portion I-FLICE-2 protein is amplified from the deposited cDNA clone using PCR oligonucleotide primers which anneal to the amino terminal sequences of the desired portion of the I-FLICE-2 protein and to sequences in the deposited construct 3' to the cDNA coding sequence. Additional nucleotides containing restriction sites to facilitate cloning in the pQE60 vector are added to the 5' and 3' sequences, respectively.

For cloning the protein, the 5' primer has the sequence: 5' CGCCCATGGAGATTGGTGAGGATTTG 3' (SEQ ID NO:9) containing the underlined NcoI restriction site followed by 17 (i.e., 311–328) nucleotides complementary to the amino terminal coding sequence of the I-FLICE-2 sequence in FIGS. 4A–4C (SEQ ID NO:5). one of ordinary skill in the art would appreciate, of course, that the point in the protein coding sequence where the 5' primer begins may be varied to amplify a DNA segment encoding any desired portion of the complete protein in a shorter or longer form. The 3' primer has the sequence: 5'CGC AAGCTTAGAGCATGCAGTGTCAG 3' (SEQ ID NO:10) containing the underlined HindIII restriction site followed by 16 (i.e., 1400–1416) nucleotides complementary to the 3' end of the coding sequence immediately before the stop codon in the I-FLICE-2 DNA sequence in FIGS. 4A–4C (SEQ ID NO:5), with the coding sequence aligned with the restriction site so as to maintain its reading frame with that of the six His codons in the pQE60 vector.

The amplified I-FLICE-2 DNA fragment and the vector pQE60 are digested with NcoI/HindIII and the digested DNAs are then ligated together. Insertion of the I-FLICE-2 DNA into the restricted pQE60 vector places the I-FLICE-2 protein coding region downstream from the IPTG-inducible promoter and in-frame with an initiating AUG and the six histidine codons.

The ligation mixture is transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan'"), is used in carrying out the illustrative example described herein. This strain, which is only one of many that are suitable for expressing I-FLICE-2 protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH8. The cell debris is removed by centrifugation, and the supernatant containing the I-FLICE-2 is loaded onto a nickel-nitrilo-tri-acetic acid ("NiNTA") affinity resin column (available from QIAGEN, Inc., supra). Proteins with a 6×His tag bind to the NI-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH8, the column is first washed with 10 volumes of 6 M guanidine-HCl, pH8, then washed with 10 volumes of 6 M guanidine-HCl pH6, and finally the I-FLICE-2 is eluted with 6 M guanidine-HCl, pH5.

The purified protein is then renatured by dialyzing it against phosphate buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH7.4, containing protease inhibitors. The renaturation should be performed over a period of 1.5 hours or more. After renaturation the proteins can be eluted by the addition of 250 mM imidazole. Imidazole is removed by a final dialyzing step against PBS or 50 mM sodium acetate pH6 buffer plus 200 mM NaCl. The purified protein is stored at 4° C. or frozen at −80° C.

Example 2(a)

Cloning and Expression of I-FLICE-1 protein in a Baculovirus Expression System

In this illustrative example, the plasmid shuttle vector pA2 is used to insert the cloned DNA encoding the complete protein into a baculovirus to express the I-FLICE-1 protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding the full length I-FLICE-1 protein in the deposited clone, including the AUG initiation codon shown in FIGS. 1A–1B (SEQ ID NO:1), is amplified using PCR oligonucleotide primers corresponding to the 5' and 3' sequences of the gene. The 5' primer has the sequence: 5'CGCGGATCCGCCATCATGTCTGCTGAAGTCATC 3' (SEQ ID NO:11) containing the underlined BamHI restriction enzyme site, an efficient signal for initiation of translation in eukaryotic cells, as described by Kozak, M., *J. Mol. Biol.* 196:947–950 (1987), followed by 17 (i.e., 268–285) bases of the sequence of the complete I-FLICE-1 protein shown in FIG. 1A–1B, beginning with the AUG initiation codon. The 3' primer has the sequence: 5'CGC GGTACCGTGCTGGGATTACAGGTG 3' (SEQ ID NO:12) containing the underlined, Asp718 restriction site followed by 18 (1740–1758) nucleotides complementary to the 3' noncoding sequence in FIG. 1A–1B (SEQ ID NO:1).

The amplified fragment is isolated from a 1% agarose gel using a commercially available kit ("GENECLEAN®" BIO 101 Inc., La Jolla, Calif.). The fragment then is digested with BamHI and Asp718 and again is purified on a 1% agarose gel. This fragment is designated herein "F1".

The plasmid is digested with the restriction enzymes BamHI and Asp718 and optionally, can be dephosphorylated using calf intestinal phosphatase, using routine procedures known in the art. The DNA is then isolated from a 1% agarose gel using a commercially available kit ("GENECLEAN®" BIO 101 Inc., LaJolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 BLUE® (Stratagene Cloning Systems, La Jolla, Calif.) cells are transformed with the ligation mixture and spread on culture plates. Bacteria are identified that contain the plasmid with the human I-FLICE-1 gene using the PCR method, in which one of the primers that is used to amplify the gene and the second primer is from well within the vector so that only those bacterial colonies containing the I-FLICE-1 gene fragment will show amplification of the DNA. The sequence of the cloned fragment is confirmed by DNA sequencing. This plasmid is designated herein pBac I-FLICE-1.

Five µg of the plasmid pBac I-FLICE-1 is co-transfected with 1.0 µg of a commercially available linearized baculovirus DNA ("BACULOGOLD™ baculovirus DNA", Pharminogen, San Diego, Calif.), using the lipofection method described by Felgner et al., *Proc. Natl. Acad. Sci. USA* 84:7413–7417 (1987). 1 µg of BACULOGOLD™ virus DNA and 5 µg of the plasmid pBac I-FLICE-1 are mixed in a sterile well of a microtiter plate containing 50 µµl of serum-free Grace's medium (Life Technologies Inc., Gaithersburg, Md.). Afterwards, 10 µl LIPOFECTIN® plus 90 µl Grace's medium are added, mixed and incubated for 15 minutes at room temperature. Then the transfection mixture is added drop-wise to Sf9 insect cells (ATCC® CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "BLUE GAL®" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-I-FLICE-1.

To verify the expression of the I-FLICE-1 gene, Sf9 cells are grown in Grace's medium supplemented with 10% heat inactivated FBS. The cells are infected with the recombinant baculovirus V-I-FLICE-1 at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 µCi of $^{35}$S-methionine and 5 µCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 2(b)

Cloning and Expression of I-FLICE-2 Protein in a Baculovirus Expression System

In this illustrative example, the plasmid shuttle vector pA2 is used to insert the cloned DNA encoding the complete protein into a baculovirus to express the I-FLICE-2 protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding the full length I-FLICE-2 protein in the deposited clone, including the AUG initiation codon shown in FIG. 4A–4C (SEQ ID NO:6) is amplified using PCR oligonucleotide primers corresponding to the 5' and 3' sequences of the gene. The 5' primer has the sequence: 5' CGCGGATCCGCCATCATGGCAGAGATTGGTGAG 3' (SEQ ID NO:13) containing the underlined BamHI restriction enzyme site, an efficient signal for initiation of translation in eukaryotic cells, as described by Kozak, M., *J. Mol. Biol.* 196:947–950 (1987), followed by 17 (304–321) bases of the sequence of the complete I-FLICE-2 protein shown in FIG. 4A–4C, beginning with the AUG initiation codon. The 3' primer has the sequence: 5'CGC GGTACCAGAGCATGCAGTGTCAG 3' (SEQ ID NO: 14) containing the underlined, Asp718 restriction site followed by (i.e., 1400–1416) nucleotides complementary to the 3' noncoding sequence in FIG. 4A–4C (SEQ ID NO:5).

The amplified fragment is isolated from a 1% agarose gel using a commercially available kit ("GENECLEAN®" BIO 101 Inc., La Jolla, Calif.). The fragment then is digested with BamHI and Asp718 and again is purified on a 1% agarose gel. This fragment is designated herein "F1".

The plasmid is digested with the restriction enzymes BamHI and Asp718 and optionally, can be dephosphorylated using calf intestinal phosphatase, using routine procedures known in the art. The DNA is then isolated from a 1% agarose gel using a commercially available kit ("GENECLEAN®" BIO 101 Inc., La Jolla, Calif.). This vector DNA is designated herein "V1".

Fragment F1 and the dephosphorylated plasmid V1 are ligated together with T4 DNA ligase. *E. coli* HB 101 or other suitable *E. coli* hosts such as XL-1 BLUE® (Stratagene Cloning Systems, La Jolla, Calif.) cells are transformed with the ligation mixture and spread on culture plates. Bacteria are identified that contain the plasmid with the human I-FLICE-2 gene using the PCR method, in which one of the primers that is used to amplify the gene and the second primer is from well within the vector so that only those bacterial colonies containing the I-FLICE-2 gene fragment will show amplification of the DNA. The sequence of the cloned fragment is confirmed by DNA sequencing. This plasmid is designated herein pBac I-FLICE-2.

Five μg of the plasmid pBac I-FLICE-2 is co-transfected with 1.0 μg of a commercially available linearized baculovirus DNA ("BACULOGOLD™ baculovirus DNA", Pharminogen, San Diego, Calif.), using the lipofection method described by Felgner et al., *Proc. Natl. Acad. Sci. USA* 84:7413–7417 (1987). 1 μg of BACULOGOLD™ virus DNA and 5 μg of the plasmid pBac I-FLICE-2 are mixed in a sterile well of a microtiter plate containing 50 μl of serum-free Grace's medium (Life Technologies Inc., Gaithersburg, Md.). Afterwards, 10 μl LIPOFECTIN® plus 90 μl Grace's medium are added, mixed and incubated for 15 minutes at room temperature. Then the transfection mixture is added drop-wise to Sf9 insect cells (ATCC® CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "BLUE GAL®" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-I-FLICE-2.

To verify the expression of the I-FLICE-2 gene, Sf9 cells are grown in Grace's medium supplemented with 10% heat inactivated FBS. The cells are infected with the recombinant baculovirus V-I-FLICE-2 at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 μCi of $^{35}$S-methionine and 5 μCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 3

Cloning and Expression of I-FLICE in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC® 37152), pSV2dhfr (ATCC® 37146) and pBC12MI (ATCC® 67109). Mammalian host cells that could be used include, human HeLa 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molec. Cell. Biol.* 5:438–447 (1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression of I-FLICE-1 in COS Cells

The expression plasmid, p I-FLICE-1 HA, is made by cloning a cDNA encoding I-FLICE-1 into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767–778 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the I-FLICE-1 is cloned into the polylinker region of the vector so that recombinant protein expression is directed by the CMV promoter. The plasmid construction strategy is as follows. The I-FLICE-1 cDNA of the deposited clone is amplified using primers that contain convenient restriction sites, much as described above for construction of vectors for expression of I-FLICE-1 in *E. coli*. Suitable primers include the following, which are used in this example. The 5' primer, containing the underlined SmaI site, a Kozak sequence, an AUG start codon and 17 bases of the 5' coding region of the complete I-FLICE-1 has the following sequence: 5' CGC CCCGGGGCCATCATGTCTGCTGAAGTCATC (268–285) 3' (SEQ ID NO:15). The 3' primer, containing the underlined XbaI site, a stop codon, and 18 bp of 3' coding sequence has the following sequence (at the 3' end): 5' CGC TCTAGATCAAGCGTAGTCTGGGACGTCGTATGGGT AGTGCTGGGATTACAGG TG (1740–1758) 3' (SEQ ID NO:16).

The PCR amplified DNA fragment and the vector, pcDNAI/Amp, are digested with SmaI and XbaI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the I-FLICE-1-encoding fragment.

For expression of recombinant I-FLICE-1, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of I-FLICE-1 by the vector.

Expression of the I-FLICE-1-HA fusion protein is detected by radiolabeling and immunoprecipitation, using methods described in, for example Harlow et al., *Antibodies: A Laboratory Manual, 2nd Ed.*; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression of I-FLICE-1 in CHO Cells

The vector pC4 is used for the expression of I-FLICE-1 protein. Plasmid pC4 is a derivative of the plasmid pSV2-dhfr (ATCC® Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molec. Cell. Biol.* 5:438–447 (1985)) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the I-FLICE-1 in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718 and then dephosphorylated using calf intestinal phosphatase by procedures known in the art. The vector is then isolated from a 1% agarose gel.

The DNA sequence encoding the complete I-FLICE-1 protein including its leader sequence is amplified using PCR oligonucleotide primers corresponding to the 5' and 3' sequences of the gene. The 5' primer has the sequence: 5' CGCGGATCCGCCATCATGTCTGCTGAAGTCATC 3' (SEQ ID NO:17) containing the underlined BamHI restriction enzyme site, an efficient signal for initiation of translation in eukaryotic cells, as described by Kozak, M., *J. Mol. Biol.* 196:947–950 (1987), followed by 17 (i.e., 268–285) bases of the sequence of the complete I-FLICE-1 protein shown in FIG. 1A–1B, beginning with the AUG initiation codon. The 3' primer has the sequence: 5' CGC GGTACCGTGCTGGGATTACAGGTG 3' (SEQ ID NO:18) containing the underlined, Asp718 restriction site followed by 18 (1740–1758) nucleotides complementary to the 3' noncoding sequence in FIG. 1A–1B (SEQ ID NO:1).

The amplified fragment is digested with the endonucleases BamHI and Asp718 and then purified again on a 1% agarose gel. The isolated fragment and the dephosphorylated vector are then ligated with T4 DNA ligase. *E. coli* HB101 or XL-1 BLUE® cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSV2-neo using LIPOFECTIN® (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well Petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by SDS-PAGE and Western blot or by reverse phase HPLC analysis.

Example 3(c)

Cloning and Expression of I-FLICE-2 in COS Cells

The expression plasmid, pI-FLICE-2HA, is made by cloning a cDNA encoding I-FLICE-2 into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767–778 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the I-FLICE-2 is cloned into the polylinker region of the vector so that recombinant protein expression is directed by the CMV promoter. The plasmid construction strategy is as follows. The I-FLICE-2 cDNA of the deposited clone is amplified using primers that contain convenient restriction sites, much as described above for construction of vectors for expression of I-FLICE-2 in *E. coli*. Suitable primers include the following, which are used in this example. The 5' primer, containing the underlined BamHI site, a Kozak sequence, an AUG start codon and 17 codons of the 5' coding region of the complete I-FLICE-2 has the following sequence: 5' CGC GGATCCGCCATCATGGCAGAGATTGGTGAG 3' (SEQ ID NO:19). The 3' primer, containing the underlined XbaI site, a stop codon, and 16 bp of 3' coding sequence has the following sequence (at the 3' end): 5' CGC TCTAGATCAAGCGTAGT CTGGGACGTCGTATGGG-TAAGAGCATGCAGTGTCAG 3' (SEQ ID NO:20).

The PCR amplified DNA fragment and the vector, pcDNAI/Amp, are digested with BamHI and XbaI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the I-FLICE-2-encoding fragment.

For expression of recombinant I-FLICE-2, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of I-FLICE-2 by the vector.

Expression of the I-FLICE-2-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(d)

Cloning and Expression of I-FLICE-2 in CHO Cells

The vector pC4 is used for the expression of I-FLICE-2 protein. Plasmid pC4 is a derivative of the plasmid pSV2-dhfr (ATCC® Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J Biol. Chem.* 253:1357–1370, Hamlin, J. L. and Ma, C. 1990, *Biochem. et Biophys. Acta,* 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molec. Cell. Biol.* 5:438–447 (1985)) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the I-FLICE-2 in a regulated way in mammalian cells (Gossen, M., & Bujard, H. 1992, *Proc. Natl. Acad. Sci. USA* 89:5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI/Asp718 and then dephosphorylated using calf intestinal phosphatase by procedures known in the art. The vector is then isolated from a 1% agarose gel.

The DNA sequence encoding the complete I-FLICE-2 protein sequence is amplified using PCR oligonucleotide primers corresponding to the 5' and 3' sequences of the gene. The 5' primer has the sequence: 5' CGC GGATCCGCCATCATGGCAGAGATTGGTGAG 3' (SEQ ID NO:21) containing the underlined BamHI restriction enzyme site, an efficient signal for initiation of translation in eukaryotic cells, as described by Kozak, M., *J. Mol. Biol.* 196:947–950 (1987), followed by 17 (304–321) bases of the sequence of the complete I-FLICE-2 protein shown in FIG. 4A–4C, beginning with the AUG initiation codon. The 3' primer has the sequence: 5' CGC GGTACCAGAGCATGCAGTGTCAG 3' (SEQ ID NO:22) containing the underlined, Asp718 restriction site followed by (i.e., 1400–1416) nucleotides complementary to the 3' noncoding sequence in FIG. 4A–4C (SEQ ID NO:5).

The amplified fragment is digested with the endonucleases BamHI and Asp718 and then purified again on a 1% agarose gel. The isolated fragment and the dephosphorylated vector are then ligated with T4 DNA ligase. *E. coli* HB101 or XL-1 BLUE® cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSV2-neo using LIPOFECTIN® (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well Petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100–200 μM. Expression of the desired gene product is analyzed, for instance, by SDS-PAGE and Western blot or by reverse phase HPLC analysis.

Example 4(a)

Tissue distribution of I-FLICE-1 mRNA Expression

Northern blot analysis was carried out to examine I-FLICE-1 gene expression in human tissues, using methods described by, among others, Sambrook et al., cited above. A cDNA probe containing the entire nucleotide sequence of the I-FLICE-1 protein (SEQ ID NO:1) was labeled with $^{32}$P using the rediprime™ DNA labeling system (Amersham Life Science), according to manufacturer's instructions.

After labeling, the probe was purified using a CHROMA SPIN-100™ column (Clontech Laboratories, Inc.), according to manufacturer's protocol number PT1200-1. The purified labeled probe was then used to examine various human tissues for I-FLICE-1 mRNA.

Multiple Tissue Northern (MTN) blots containing various human tissues (H) or human immune system tissues (IM) were obtained from Clontech and were examined with the labeled probe using ExpressHyb™ hybridization solution (Clontech) according to manufacturer's protocol number PT1190-1. Following hybridization and washing, the blots were mounted and exposed to film at −70° C. overnight, and films developed according to standard procedures.

Two transcripts were observed (7.5 kb and 6 kb) which presumably represent mRNA sequences encoding I-FLICE-1 and I-FLICE-2. I-FLICE expression was identified in most tissues and cell lines examined except for the brain and the lymphoblastic leukemia line MOLT4. In particular, I-FLICE expression was evident in peripheral blood leukocytes, spleen, placenta and heart.

Example 4(b)

Tissue Distribution of I-FLICE-2 mRNA Expression

Northern blot analysis is carried out to examine I-FLICE-2 gene expression in human tissues, using methods described by, among others, Sambrook et al., cited above. A cDNA probe containing the entire nucleotide sequence of the I-FLICE-2 protein (SEQ ID NO:6) is labeled with $^{32}P$ using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for I-FLICE-2 mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

Example 5

I-FLICE-1 Associates with FLICE and Mch4/FLICE-2

Previous studies have shown that the DED domain is a protein interaction motif that mediates the binding of the adaptor molecule FADD to the effector proteases FLICE and Mch4/FLICE2 (Muzio et al., Cell 85:817–27 (1996); Chinnaiyan et al., Cell 81:505–12 (1995)). Given the striking structural similarity, the following experiment was performed to determine whether I-FLICE-1 interacted with either FADD or other FLICE-like caspases.

Materials and Methods

Cell Lines and Expression Vectors—Human embryonic kidney 293, 293T and 293-EBNA cells were cultured to Dulbecco's modified Eagle's medium containing 10% fetal bovine serum, nonessential amino acids, L-glutamine, and penicillin/streptomycin. Expression constructs were made in pcDNA3 or pcDNA3.1/MycHisA (Invitrogen) using standard recombinant methodologies (Sambrook, J. et al., Molecular Cloning 2nd Edition, Cold Spring Harbor Laboratory Press).

Cloning of I-FLICE-1-cDNAs corresponding to the partial open reading frame of I-FLICE-1 were identified as sequences homologous to FLICE and Mch4/FLICE2 on searching the Human Genome Sciences data base using established EST methods (Adams, M. D. et al., Science 252:1651–1656 (1991) and Adams, M. D. et al., Nature 355:632–634 (1992)). Full length cDNAs were obtained by screening a random-primed human umbilical vein endothelial cell cDNA library constructed in the pcDNA1 vector (Invitrogen). The sequence of I-FLICE-1 was confirmed by sequencing plasmid DNA template on both strands by the dideoxy chain termination method employing modified T7 DNA polymerase (Sequenase, U.S. Biochemical Corp.).

Transfection, Coimmunoprecipitation and Western Analysis—Transient transfections of 293T cells were performed as described previously (O'Rourke et al., J. Biol. Chem. 267:24921–24924 (1992)). Cells were harvested 40 hour following transfection, immunoprecipitation with α-FLAG or αmyc antibodies and analyzed by immunoblotting.

Results and Discussion

Sequence analysis of a full length cDNA revealed a 1443-base pair open reading frame that encoded a novel protein with a predicated molecular mass of 55.3 kDa (FIGS. 1A-1B). Given that the protein had striking homology to FLICE and Mch4/FLICE2 but lacked an active site, making it a potential dominant negative inhibitor, it was designated I-FLICE (for inhibitor of FLICE).

The architecture of I-FLICE-1 was strikingly similar to that of FLICE and Mch4/FLICE2, including two N-terminal DED-like tandem repeats and a region that resembled the caspase catalytic domain. Importantly, I-FLICE-1 did not contain the catalytic cysteine that is normally embedded in the conserved pentapeptide QACRG (SEQ ID NO:33) or QACQG (SEQ ID NO:34) motif present in all known caspases. Rather, the pentapeptide sequence was QNYVV (SEQ ID NO:35). In addition, based on the x-ray crystal structure of caspase-1 (and caspase-3), amino acid residues $His^{237}$ ($His^{121}$), $Gly^{238}$ ($Gly^{122}$), and $Cys^{285}$ ($Cys^{163}$) are involved in catalysis, while residues $Arg^{179}$ ($Arg^{64}$), $Gln^{283}$ ($Gln^{161}$), $Arg^{341}$ ($Arg^{207}$), and $Ser^{347}$ ($Ser^{213}$) form a binding pocket for the carboxylate side chain of the P1 aspartic acid (Wilson, K. P. et al., Nature 370:270–274 (1994), Rotonda, J. et al., Nat. Struct. Biol. 3:619–625 (1996), and Fraser, A. et al., Cell 85:781–784 (1996)). These seven residues are conserved in all caspases, but only three of them (Gly, Gln, and Ser) are found in I-FLICE-1. Given this lack of conservation of key residues involved in catalysis and substrate binding it can be concluded that I-FLICE-1 is not a cysteine protease and is incapable of binding Asp at the P1 position. Interestingly, the DED domain of I-FLICE-1 was more related to the corresponding domains present in the viral DED-containing inhibitors K13, MC 159, and E8, sharing 34%, 31%, and 33% identity (56%, 51%, and 44% similarity), respectively (Hu, S. et al., J. Biol. Chem. 272:9621–9624 (1997) and Thorne, M. et al., Nature 386: 517–521 (1997)).

Co-immunoprecipitation analysis revealed the ability of I-FLICE-1 to bind FLICE and Mch4/FLICE2 but not FADD. In this respect, I-FLICE-1 resembles the viral DED-containing molecule E8 in that it binds FLICE but not FADD (Hu et al., J. Biol. Chem. 272:9621–9624 (1997); Bertin et al.,

*Proc. Natl. Acad. Sci.* 94:1172–1176 (1997)). Since there was no association between I-FLICE-1 and FADD, I-FLICE-1 was not recruited to the CD-95 or TNFR-1 signaling complex as evidenced by its inability to co-precipitate with these receptors.

Example 6

Cell Death Assay

Given the ability of the catalytically inactive I-FLICE-1 to complex with FLICE-like caspases, the inventors reasoned that I-FLICE-1 may be acting as a dominant negative inhibitor since the active form of all caspases is a tetramer derived from the processing of two zymogen forms to a four-chain assembly. It follows that a catalytically inert zymogen, such as I-FLICE-1, would be processed to inactive subunits that would result in the generation of a non-functional tetrameric protease. This mechanism predicts that I-FLICE-1 should inhibit TNFR-1 and CD-95-induced apoptosis where FLICE-like caspases play an initiating role. The following cell death assay was performed.

Materials and Methods

Cell Death Assay—Human embryonic kidney 293 (for TNFR-1 killing) or 293 EBNA cells (for CD-95 killing) were transiently transfected with 0.1 μg of the reporter plasmid pCMV B-galactosidase plus 0.5 μg of test plasmid in the presence or absence of 2.0 μg of inhibitory plasmids. 22–24 hours after transfection, cells were fixed in 0.5% glutaraldehyde and stained with X-gal. Percentage of apoptotic cells was determined by calculating the fraction of membrane blebbed blue cells as a function of total blue cells. All assays were evaluated in duplicate and the mean and the standard deviation calculated.

Results

Figure 6A:
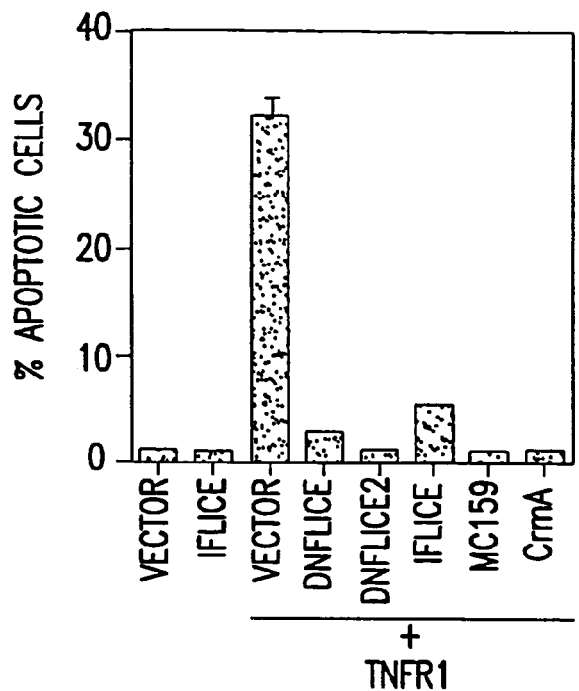
FIGS. 6A–6B show I-FLICE-1 inhibition of apoptosis. Overexpression of I-FLICE-1 attenuated TNFR-1 (panel A) and CD-95 (panel B) induced cell death. 293 (panel A) or 293-EBNA (panel B) cells were co-transfected with the indicated plasmids together with the reporter construct pCMV β-galactosidase. The data shown are the percentage of blebbing blue cells as a function of total number of blue cells counted.
Figure 6B:
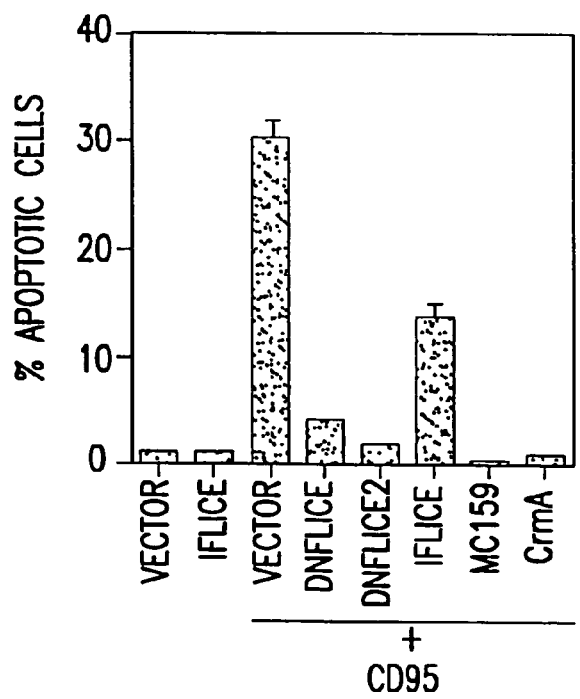

Consistent with the proposed mechanism, overexpression of I-FLICE-1 resulted in substantial inhibition of TNFR-1 induced cell death comparable to previously characterized inhibitors including CrmA, MC159, dominant negative FLICE (DNFLICE) and Mch4/FLICE2 (DNFLICE2) (see FIG. 6A). However, under the present experimental conditions, I-FLICE-1 appeared to be a less potent inhibitor of CD-95 induced cell death, possibly reflecting the more potent death signal that emanates from this receptor (see FIG. 6B).

It will be clear that the invention may be practiced otherwise than as particularly described in the foregoing description and examples. Numerous modifications and variations of the present invention are possible in light of the above teachings and, therefore, are within the scope of the appended claims.

The entire disclosures of Hu, S. et al., *J. Biol. Chem.* 272:17255–17257 (1997) and Irmler, M., et al., *Nature* 388:190–195 (1997) are hereby incorporated by reference.

What is claimed is:

1. An isolated I-FLICE-2 polypeptide comprising the amino acid sequence selected from the group consisting of:
   (a) amino acids 1 to 348 of SEQ ID NO:6;
   (b) amino acids 2 to 348 of SEQ ID NO:6;
   (c) the amino acid sequence of the complete I-FLICE-2 polypeptide encoded by the cDNA contained in ATCC Deposit No. 209038; and
   (d) the amino acid sequence of the complete I-FLICE-2 polypeptide encoded by the cDNA contained in ATCC Deposit No. 209038 excepting the N-terminal methionine.

2. The isolated I-FLICE-2 polypeptide of claim 1 which comprises the amino acid sequence of (a).

3. The isolated I-FLICE-2 polypeptide of claim 1 which comprises the amino acid sequence of (b).

4. The isolated I-FLICE-2 polypeptide of claim 1 which comprises the amino acid sequence of(c).

5. The isolated I-FLICE-2 polypeptide of claim 1 which comprises the amino acid sequence of(d).

6. A fusion protein comprising the isolated I-FLICE polypeptide of claim 1 fused to a heterologous polypeptide.

7. The fusion protein of claim 6, wherein said heterologous polypeptide is the Fc domain of immunoglobulin.

8. The isolated I-FLICE-2 polypeptide of claim 1, wherein the polypeptide is glycosylated.

9. A composition comprising the isolated I-FLICE-2 polypeptide of claim 1 and a carrier.

10. An isolated I-FLICE-2 polypeptide produced by a method comprising:
(a) culturing a host cell under conditions suitable to produce the isolated I-FLICE-2 polypeptide of claim 1; and
(b) recovering said I-FLICE-2 polypeptide from the host cell culture.

11. An isolated I-FLICE-2 polypeptide consisting of the amino acid sequence selected from the group consisting of:
(a) amino acids 1 to 75 of SEQ ID NO:6;
(b) amino acids 76 to 252 of SEQ ID NO:6; and
(c) amino acids 253 to 348 of SEQ ID NO:6.

12. An isolated I-FLICE-2 polypeptide comprising the amino acid sequence at least 95% identical to the amino acid sequence selected from the group consisting of:
(a) amino acids 1 to 348 of SEQ ID NO:6; and
(b) the amino acid sequence encoded by the cDNA contained in ATCC Deposit No. 209038;
wherein said I-FLICE-2 polypeptide inhibits TNFR-1 and CD-95 induced apoptosis.

13. The I-FLICE-2 polypeptide of claim 12 which comprises the amino acid sequence of (a).

14. The I-FLICE-2 polypeptide of claim 12 which comprises the amino acid sequence of (b).

15. A fusion protein comprising the isolated I-FLICE polypeptide of claim 12 fused to a heterologous polypeptide.

16. The fusion protein of claim 15, wherein said heterologous polypeptide is the Fc domain of immunoglobulin.

17. The isolated I-FLICE-2 polypeptide of claim 12, wherein the polypeptide is glycosylated.

18. A composition comprising the isolated I-FLICE-2 polypeptide of claim 12 and a carrier.

19. An isolated I-FLICE-2 polypeptide produced by a method comprising:
(a) culturing a host cell under conditions suitable to produce the isolated I-FLICE-2 polypeptide of claim 12; and
(b) recovering said I-FLICE-2 polypeptide from the host cell culture.

* * * * *

UNITED STATES PATENT AND TRADEMARK OFFICE
CERTIFICATE OF CORRECTION

PATENT NO. : 7,056,516 B2
APPLICATION NO. : 10/713208
DATED : June 6, 2006
INVENTOR(S) : Ni et al.

It is certified that error appears in the above-identified patent and that said Letters Patent is hereby corrected as shown below:

TITLE PG, ITEM (56) OTHER REF.

Column 2, line 2, delete "19967", and insert --1997--.

Column 2, line 13, delete "Jul.", and insert --April--.

Column 2, delete lines four through twelve.

Signed and Sealed this

Seventeenth Day of October, 2006

JON W. DUDAS
*Director of the United States Patent and Trademark Office*

SEQUENCE LISTING

```
<160> NUMBER OF SEQ ID NOS: 35

<210> SEQ ID NO 1
<211> LENGTH: 2034
<212> TYPE: DNA
<213> ORGANISM: Homo sapiens
<220> FEATURE:
<221> NAME/KEY: CDS
<222> LOCATION: (268)..(1707)

<400> SEQUENCE: 1
cgatcgccca gcaccaagtc cgcttccagg ctttcggttt ctttgcctcc atcttgggtg      60
cgccttcccg gcgtctaggg gagcgaaggc tgaggtggca gcggcaggag agtccggccg     120
cgacaggacg aactccccca ctggaaagga ttctgaaaga aatgaagtca gccctcagaa     180
atgaagttga ctgcctgctg gctttctgtt gactggcccg gagctgtact gcaagaccct     240
tgtgagcttc cctagtctaa gagtagg atg tct gct gaa gtc atc cat cag gtt    294
                                Met Ser Ala Glu Val Ile His Gln Val
                                  1               5 gaa gaa gca ctt gat aca gat gag aag gag atg ctg ctc ttt ttg tgc      342
Glu Glu Ala Leu Asp Thr Asp Glu Lys Glu Met Leu Leu Phe Leu Cys
 10              15                  20                  25 cgg gat gtt gct ata gat gtg gtt cca cct aat gtc agg gac ctt ctg      390
Arg Asp Val Ala Ile Asp Val Val Pro Pro Asn Val Arg Asp Leu Leu
                 30                  35                  40 gat att tta cgg gaa aga ggt aag ctg tct gtc ggg gac ttg gct gaa      438
Asp Ile Leu Arg Glu Arg Gly Lys Leu Ser Val Gly Asp Leu Ala Glu
             45                  50                  55 ctg ctc tac aga gtg agg cga ttt gac ctg ctc aaa cgt atc ttg aag      486
Leu Leu Tyr Arg Val Arg Arg Phe Asp Leu Leu Lys Arg Ile Leu Lys
         60                  65                  70 atg gac aga aaa gct gtg gag acc cac ctg ctc agg aac cct cac ctt      534
```

```
                Met Asp Arg Lys Ala Val Glu Thr His Leu Leu Arg Asn Pro His Leu
                 75                  80                  85 gtt tcg gac tat aga gtg ctg atg gca gag att ggt gag gat ttg gat        582
Val Ser Asp Tyr Arg Val Leu Met Ala Glu Ile Gly Glu Asp Leu Asp
 90                  95                 100                 105 aaa tct gat gtg tcc tca tta att ttc ctc atg aag gat tac atg ggc        630
Lys Ser Asp Val Ser Ser Leu Ile Phe Leu Met Lys Asp Tyr Met Gly
                    110                 115                 120 cga ggc aag ata agc aag gag aag agt ttc ttg gac ctt gtg gtt gag        678
Arg Gly Lys Ile Ser Lys Glu Lys Ser Phe Leu Asp Leu Val Val Glu
                125                 130                 135 ttg gag aaa cta aat ctg gtt gcc cca gat caa ctg gat tta tta gaa        726
Leu Glu Lys Leu Asn Leu Val Ala Pro Asp Gln Leu Asp Leu Leu Glu
        140                 145                 150 aaa tgc cta aag aac atc cac aga ata gac ctg aag aca aaa atc cag        774
Lys Cys Leu Lys Asn Ile His Arg Ile Asp Leu Lys Thr Lys Ile Gln
        155                 160                 165 aag tac aag cag tct gtt caa gga gca ggg aca agt tac agg aat gtt        822
Lys Tyr Lys Gln Ser Val Gln Gly Ala Gly Thr Ser Tyr Arg Asn Val
170                 175                 180                 185 ctc caa gca gca atc caa aag agt ctc aag gat cct tca aat aac ttc        870
Leu Gln Ala Ala Ile Gln Lys Ser Leu Lys Asp Pro Ser Asn Asn Phe
                190                 195                 200 agg ctc cat aat ggg aga agt aaa gaa caa aga ctt aag gaa cag ctt        918
Arg Leu His Asn Gly Arg Ser Lys Glu Gln Arg Leu Lys Glu Gln Leu
                205                 210                 215 ggc gct caa caa gaa cca gtg aag aaa tcc att cag gaa tca gaa gct        966
Gly Ala Gln Gln Glu Pro Val Lys Lys Ser Ile Gln Glu Ser Glu Ala
            220                 225                 230 ttt ttg cct cag agc ata cct gaa gag aga tac aag atg aag agc aag       1014
Phe Leu Pro Gln Ser Ile Pro Glu Glu Arg Tyr Lys Met Lys Ser Lys
            235                 240                 245 ccc cta gga atc tgc ctg ata atc gat tgc att ggc aat gag aca gag       1062
Pro Leu Gly Ile Cys Leu Ile Ile Asp Cys Ile Gly Asn Glu Thr Glu
250                 255                 260                 265 ctt ctt cga gac acc ttc act tcc ctg ggc tat gaa gtc cag aaa ttc       1110
Leu Leu Arg Asp Thr Phe Thr Ser Leu Gly Tyr Glu Val Gln Lys Phe
                270                 275                 280 ttg cat ctc agt atg cat ggt ata tcc cag att ctt ggc caa ttt gcc       1158
Leu His Leu Ser Met His Gly Ile Ser Gln Ile Leu Gly Gln Phe Ala
                285                 290                 295 tgt atg ccc gag cac cga gac tac gac agc ttt gtg tgt gtc ctg gtg       1206
Cys Met Pro Glu His Arg Asp Tyr Asp Ser Phe Val Cys Val Leu Val
            300                 305                 310 agc cga gga ggc tcc cag agt gtg tat ggt gtg gat cag act cac tca       1254
Ser Arg Gly Gly Ser Gln Ser Val Tyr Gly Val Asp Gln Thr His Ser
            315                 320                 325 ggg ctc ccc ctg cat cac atc agg agg atg ttc atg gga gat tca tgc       1302
Gly Leu Pro Leu His His Ile Arg Arg Met Phe Met Gly Asp Ser Cys
330                 335                 340                 345 cct tat cta gca ggg aag cca aag atg ttt ttt att cag aac tat gtg       1350
Pro Tyr Leu Ala Gly Lys Pro Lys Met Phe Phe Ile Gln Asn Tyr Val
                350                 355                 360 gtg tca gag ggc cag ctg gag gac agc agc ctc ttg gag gtg gat ggg       1398
Val Ser Glu Gly Gln Leu Glu Asp Ser Ser Leu Leu Glu Val Asp Gly
                365                 370                 375 cca gcg atg aag aat gtg gaa ttc aag gct cag aag cga ggg ctg tgc       1446
Pro Ala Met Lys Asn Val Glu Phe Lys Ala Gln Lys Arg Gly Leu Cys
            380                 385                 390
```

-continued

```
aca gtt cac cga gaa gct gac ttc ttc tgg agc ctg tgt act gcg gac    1494
Thr Val His Arg Glu Ala Asp Phe Phe Trp Ser Leu Cys Thr Ala Asp
    395                 400                 405 atg tcc ctg ctg gag cag tct cac agc tca ccg tcc ctg tac ctg cag    1542
Met Ser Leu Leu Glu Gln Ser His Ser Ser Pro Ser Leu Tyr Leu Gln
410                 415                 420                 425 tgc ctc tcc cag aaa ctg aga caa gaa aga aaa cgc cca ctc ctg gat    1590
Cys Leu Ser Gln Lys Leu Arg Gln Glu Arg Lys Arg Pro Leu Leu Asp
                430                 435                 440 ctt cac att gaa ctc aat ggc tac atg tat gat tgg aac agc aga gtt    1638
Leu His Ile Glu Leu Asn Gly Tyr Met Tyr Asp Trp Asn Ser Arg Val
            445                 450                 455 tct gcc aag gag aaa tat tat gtc tgg ctg cag cac act ctg aga aag    1686
Ser Ala Lys Glu Lys Tyr Tyr Val Trp Leu Gln His Thr Leu Arg Lys
        460                 465                 470 aaa ctt atc ctc tcc tac aca taagaaacca aaaggctggg cgtagtggct       1737
Lys Leu Ile Leu Ser Tyr Thr
    475                 480 cgcacctgta atcccagcac tttgggaggc caaggagggc ggatcacttc aggtcaggag    1797
ttcgagacca gcctggccaa catggtaaac gctgtcccta gtaagagtgc aaaaattagc    1857
tgggtgtggg tgtgggtacc tgtgttccca gttacttggg aggctgaggt gggaggatct    1917
tttgaaccca ggagttcagg gtcatagcat gctgtgattg tgcctacgaa tagccactgc    1977
ataccaacct gggcaatata gcaagatccc atcttttaa aaaaaaaaaa aaaaaaa       2034

<210> SEQ ID NO 2
<211> LENGTH: 480
<212> TYPE: PRT
<213> ORGANISM: Homo sapiens

<400> SEQUENCE: 2

Met Ser Ala Glu Val Ile His Gln Val Glu Glu Ala Leu Asp Thr Asp
1               5                   10                  15

Glu Lys Glu Met Leu Leu Phe Leu Cys Arg Asp Val Ala Ile Asp Val
            20                  25                  30

Val Pro Pro Asn Val Arg Asp Leu Leu Asp Ile Leu Arg Glu Arg Gly
        35                  40                  45

Lys Leu Ser Val Gly Asp Leu Ala Glu Leu Leu Tyr Arg Val Arg Arg
    50                  55                  60

Phe Asp Leu Leu Lys Arg Ile Leu Lys Met Asp Arg Lys Ala Val Glu
65                  70                  75                  80

Thr His Leu Leu Arg Asn Pro His Leu Val Ser Asp Tyr Arg Val Leu
                85                  90                  95

Met Ala Glu Ile Gly Glu Asp Leu Asp Lys Ser Asp Val Ser Ser Leu
            100                 105                 110

Ile Phe Leu Met Lys Asp Tyr Met Gly Arg Gly Lys Ile Ser Lys Glu
        115                 120                 125

Lys Ser Phe Leu Asp Leu Val Val Glu Leu Glu Lys Leu Asn Leu Val
    130                 135                 140

Ala Pro Asp Gln Leu Asp Leu Leu Glu Lys Cys Leu Lys Asn Ile His
145                 150                 155                 160

Arg Ile Asp Leu Lys Thr Lys Ile Gln Lys Tyr Lys Gln Ser Val Gln
                165                 170                 175

Gly Ala Gly Thr Ser Tyr Arg Asn Val Leu Gln Ala Ala Ile Gln Lys
            180                 185                 190

Ser Leu Lys Asp Pro Ser Asn Asn Phe Arg Leu His Asn Gly Arg Ser
```

-continued

```
            195                 200                 205
Lys Glu Gln Arg Leu Lys Glu Gln Leu Gly Ala Gln Gln Glu Pro Val
    210                 215                 220
Lys Lys Ser Ile Gln Glu Ser Glu Ala Phe Leu Pro Gln Ser Ile Pro
225                 230                 235                 240
Glu Glu Arg Tyr Lys Met Lys Ser Lys Pro Leu Gly Ile Cys Leu Ile
                245                 250                 255
Ile Asp Cys Ile Gly Asn Glu Thr Glu Leu Leu Arg Asp Thr Phe Thr
            260                 265                 270
Ser Leu Gly Tyr Glu Val Gln Lys Phe Leu His Leu Ser Met His Gly
        275                 280                 285
Ile Ser Gln Ile Leu Gly Gln Phe Ala Cys Met Pro Glu His Arg Asp
    290                 295                 300
Tyr Asp Ser Phe Val Cys Val Leu Val Ser Arg Gly Gly Ser Gln Ser
305                 310                 315                 320
Val Tyr Gly Val Asp Gln Thr His Ser Gly Leu Pro Leu His His Ile
                325                 330                 335
Arg Arg Met Phe Met Gly Asp Ser Cys Pro Tyr Leu Ala Gly Lys Pro
            340                 345                 350
Lys Met Phe Phe Ile Gln Asn Tyr Val Val Ser Glu Gly Gln Leu Glu
        355                 360                 365
Asp Ser Ser Leu Leu Glu Val Asp Gly Pro Ala Met Lys Asn Val Glu
    370                 375                 380
Phe Lys Ala Gln Lys Arg Gly Leu Cys Thr Val His Arg Glu Ala Asp
385                 390                 395                 400
Phe Phe Trp Ser Leu Cys Thr Ala Asp Met Ser Leu Leu Glu Gln Ser
                405                 410                 415
His Ser Ser Pro Ser Leu Tyr Leu Gln Cys Leu Ser Gln Lys Leu Arg
            420                 425                 430
Gln Glu Arg Lys Arg Pro Leu Leu Asp Leu His Ile Glu Leu Asn Gly
        435                 440                 445
Tyr Met Tyr Asp Trp Asn Ser Arg Val Ser Ala Lys Glu Lys Tyr Tyr
    450                 455                 460
Val Trp Leu Gln His Thr Leu Arg Lys Leu Ile Leu Ser Tyr Thr
465                 470                 475                 480

<210> SEQ ID NO 3
<211> LENGTH: 478
<212> TYPE: PRT
<213> ORGANISM: Homo sapiens

<400> SEQUENCE: 3

Met Asp Phe Ser Arg Asn Leu Tyr Asp Ile Gly Glu Gln Leu Asp Ser
1               5                   10                  15
Glu Asp Leu Ala Ser Leu Lys Phe Leu Ser Leu Asp Tyr Ile Pro Gln
            20                  25                  30
Arg Lys Gln Glu Pro Ile Lys Asp Ala Leu Met Leu Phe Gln Arg Leu
        35                  40                  45
Gln Glu Lys Arg Met Leu Glu Glu Ser Asn Leu Ser Phe Leu Lys Glu
    50                  55                  60
Leu Leu Phe Arg Ile Asn Arg Leu Asp Leu Leu Ile Thr Tyr Leu Asn
65                  70                  75                  80
Thr Arg Lys Glu Glu Met Glu Arg Glu Leu Gln Thr Pro Gly Arg Ala
                85                  90                  95
```

```
Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
            115                 120                 125

Ser Lys Cys Lys Leu Asp Asp Met Asn Leu Leu Asp Ile Phe Ile
            130                 135                 140

Glu Met Glu Lys Arg Val Ile Leu Gly Glu Gly Lys Leu Asp Ile Leu
145                     150                 155                 160

Lys Arg Val Cys Ala Gln Ile Asn Lys Ser Leu Leu Lys Ile Ile Asn
                    165                 170                 175

Asp Tyr Glu Glu Phe Ser Lys Glu Arg Ser Ser Ser Leu Glu Gly Ser
                180                 185                 190

Pro Asp Glu Phe Ser Asn Gly Glu Glu Leu Cys Gly Val Met Thr Ile
            195                 200                 205

Ser Asp Ser Pro Arg Glu Gln Asp Ser Glu Ser Gln Thr Leu Asp Lys
            210                 215                 220

Val Tyr Gln Met Lys Ser Lys Pro Arg Gly Tyr Cys Leu Ile Ile Asn
225                     230                 235                 240

Asn His Asn Phe Ala Lys Ala Arg Glu Lys Val Pro Lys Leu His Ser
                    245                 250                 255

Ile Arg Asp Arg Asn Gly Thr His Leu Asp Ala Gly Leu Thr Thr Thr
                260                 265                 270

Phe Glu Glu Leu His Phe Glu Ile Lys Pro His Asp Asp Cys Thr Val
            275                 280                 285

Glu Gln Ile Tyr Glu Ile Leu Lys Ile Tyr Gln Leu Met Asp His Ser
290                     295                 300

Asn Met Asp Cys Phe Ile Cys Cys Ile Leu Ser His Gly Asp Lys Gly
305                     310                 315                 320

Ile Ile Tyr Gly Thr Asp Gly Gln Glu Pro Ile Tyr Glu Leu Thr
                    325                 330                 335

Ser Gln Phe Thr Gly Leu Lys Cys Pro Ser Leu Ala Gly Lys Pro Lys
                340                 345                 350

Val Phe Phe Ile Gln Ala Cys Gln Gly Asp Asn Tyr Gln Lys Gly Ile
            355                 360                 365

Pro Val Glu Thr Asp Ser Glu Gln Pro Tyr Leu Glu Met Asp Leu
            370                 375                 380

Ser Ser Pro Gln Thr Arg Tyr Ile Pro Asp Glu Ala Asp Phe Leu Leu
385                     390                 395                 400

Gly Met Ala Thr Val Asn Asn Cys Val Ser Tyr Arg Asn Pro Ala Glu
                    405                 410                 415

Gly Thr Trp Tyr Ile Gln Ser Leu Cys Gln Ser Leu Arg Glu Arg Cys
                420                 425                 430

Pro Arg Gly Asp Asp Ile Leu Thr Ile Leu Thr Glu Val Asn Tyr Glu
            435                 440                 445

Val Ser Asn Lys Asp Asp Lys Lys Asn Met Gly Lys Gln Met Pro Gln
450                     455                 460

Pro Thr Phe Thr Leu Arg Lys Lys Leu Val Phe Pro Ser Asp
465                     470                 475

<210> SEQ ID NO 4
<211> LENGTH: 479
<212> TYPE: PRT
<213> ORGANISM: Homo sapiens

<400> SEQUENCE: 4
```

```
Met Lys Ser Gln Gly Gln His Trp Tyr Ser Ser Asp Lys Asn Cys
 1               5                  10                  15

Lys Val Ser Phe Arg Glu Lys Leu Leu Ile Ile Asp Ser Asn Leu Gly
            20                  25                  30

Val Gln Asp Val Glu Asn Leu Lys Phe Leu Cys Ile Gly Leu Val Pro
        35                  40                  45

Asn Lys Lys Leu Glu Lys Ser Ser Ala Ser Asp Val Phe Glu His
    50                  55                  60

Leu Leu Ala Glu Asp Leu Leu Ser Glu Glu Asp Pro Phe Phe Leu Ala
65                  70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
    130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
        195                 200                 205

Gln Gly Glu Glu Glu Leu Val Ser Gln Thr Asp Val Lys Thr Phe Leu
    210                 215                 220

Glu Ala Leu Pro Arg Ala Ala Val Tyr Arg Met Asn Arg Asn His Arg
225                 230                 235                 240

Gly Leu Cys Val Ile Val Asn Asn His Ser Phe Thr Ser Leu Lys Asp
                245                 250                 255

Arg Gln Gly Thr His Lys Asp Ala Glu Ile Leu Ser His Val Phe Gln
            260                 265                 270

Trp Leu Gly Phe Thr Val His Ile His Asn Asn Val Thr Lys Val Glu
        275                 280                 285

Met Glu Met Val Leu Gln Lys Gln Lys Cys Asn Pro Ala His Ala Asp
    290                 295                 300

Gly Asp Cys Phe Val Phe Cys Ile Leu Thr His Gly Arg Phe Gly Ala
305                 310                 315                 320

Val Tyr Ser Ser Asp Glu Ala Leu Ile Pro Ile Arg Glu Ile Met Ser
                325                 330                 335

His Phe Thr Ala Leu Gln Cys Pro Arg Leu Ala Glu Lys Pro Lys Leu
            340                 345                 350

Phe Phe Ile Gln Ala Cys Gln Gly Glu Glu Ile Gln Pro Ser Val Ser
        355                 360                 365

Ile Glu Ala Asp Ala Leu Asn Pro Glu Gln Ala Pro Thr Ser Leu Gln
    370                 375                 380

Asp Ser Ile Pro Ala Glu Ala Asp Phe Leu Leu Gly Leu Ala Thr Val
385                 390                 395                 400

Pro Gly Tyr Val Ser Phe Arg His Val Glu Glu Gly Ser Trp Tyr Ile
                405                 410                 415
```

```
Gln Ser Leu Cys Asn His Leu Lys Lys Leu Val Pro Arg His Glu Asp
            420                 425                 430

Ile Leu Ser Ile Leu Thr Ala Val Asn Asp Asp Val Ser Arg Arg Val
            435                 440                 445

Asp Lys Gln Gly Thr Lys Lys Gln Met Pro Gln Pro Ala Phe Thr Leu
    450                 455                 460

Arg Lys Lys Leu Val Phe Pro Val Pro Leu Asp Ala Leu Ser Ile
465                 470                 475

<210> SEQ ID NO 5
<211> LENGTH: 2597
<212> TYPE: DNA
<213> ORGANISM: Homo sapiens
<220> FEATURE:
<221> NAME/KEY: CDS
<222> LOCATION: (304)..(1347)

<400> SEQUENCE: 5
```

| | |
|---|---:|
| gcgagcttgc agcctcaccg acgagtctca actaaaaggg actcccggag ctaggggtgg | 60 |
| ggactcggcc tcacacagtg attgccggct attggacttt tgtccagtga cagctgagac | 120 |
| aacaaggacc acgggaggag gtgtaggaga gaagcgccgc gaacaggcat cgcccagcac | 180 |
| caagtccgct tccaggcttt cggtttcttt gcctccatct tgggtgcgcc ttcccggcgt | 240 |
| ctaggggagc gaaggctgag gtggcagcgg caggagagtc cggccgcgac aggacgagtg | 300 |

| | |
|---|---:|
| ctg atg gca gag att ggt gag gat ttg gat aaa tct gat gtg tcc tca | 348 |
|     Met Ala Glu Ile Gly Glu Asp Leu Asp Lys Ser Asp Val Ser Ser | |
|     1             5                10             15 | |
| tta att ttc ctc atg aag gat tac atg ggc cga ggc aag ata agc aag | 396 |
| Leu Ile Phe Leu Met Lys Asp Tyr Met Gly Arg Gly Lys Ile Ser Lys | |
|             20                25               30 | |
| gag aag agt ttc ttg gac ctt gtg gtt gag ttg gag aaa cta aat ctg | 444 |
| Glu Lys Ser Phe Leu Asp Leu Val Val Glu Leu Glu Lys Leu Asn Leu | |
|      35                40               45 | |
| gtt gcc cca gat caa ctg gat tta tta gaa aaa tgc cta aag aac atc | 492 |
| Val Ala Pro Asp Gln Leu Asp Leu Leu Glu Lys Cys Leu Lys Asn Ile | |
|         50               55              60 | |
| cac aga ata gac ctg aag aca aaa atc cag aag tac aag cag tct gtt | 540 |
| His Arg Ile Asp Leu Lys Thr Lys Ile Gln Lys Tyr Lys Gln Ser Val | |
| 65                70               75 | |
| caa gga gca ggg aca agt tac agg aat gtt ctc caa gca gca atc caa | 588 |
| Gln Gly Ala Gly Thr Ser Tyr Arg Asn Val Leu Gln Ala Ala Ile Gln | |
| 80                85               90              95 | |
| aag agt ctc aag gat cct tca aat aac ttc agg gaa gaa cca gtg aag | 636 |
| Lys Ser Leu Lys Asp Pro Ser Asn Asn Phe Arg Glu Glu Pro Val Lys | |
|               100              105            110 | |
| aaa tcc att cag gaa tca gaa gct ttt ttg cct cag agc ata cct gaa | 684 |
| Lys Ser Ile Gln Glu Ser Glu Ala Phe Leu Pro Gln Ser Ile Pro Glu | |
|          115             120            125 | |
| gag aga tac aag atg aag agc aag ccc cta gga atc tgc ctg ata atc | 732 |
| Glu Arg Tyr Lys Met Lys Ser Lys Pro Leu Gly Ile Cys Leu Ile Ile | |
|     130              135            140 | |
| gat tgc att ggc aat gag aca gag ctt ctt cga gac acc ttc act tcc | 780 |
| Asp Cys Ile Gly Asn Glu Thr Glu Leu Leu Arg Asp Thr Phe Thr Ser | |
|     145              150            155 | |
| ctg ggc tat gaa gtc cag aaa ttc ttg cat ctc agt atg cat ggt ata | 828 |
| Leu Gly Tyr Glu Val Gln Lys Phe Leu His Leu Ser Met His Gly Ile | |
| 160               165            170             175 | |
| tcc cag att ctt ggc caa ttt gcc tgt atg ccc gag cac cga gac tac | 876 |
| Ser Gln Ile Leu Gly Gln Phe Ala Cys Met Pro Glu His Arg Asp Tyr | |

-continued

```
                180                 185                 190
gac agc ttt gtg tgt gtc ctg gtg agc cga gga ggc tcc cag agt gtg      924
Asp Ser Phe Val Cys Val Leu Val Ser Arg Gly Gly Ser Gln Ser Val
            195                 200                 205 tat ggt gtg gat cag act cac tca ggg ctc ccc ctg cat cac atc agg      972
Tyr Gly Val Asp Gln Thr His Ser Gly Leu Pro Leu His His Ile Arg
        210                 215                 220 agg atg ttc atg gga gat tca tgc cct tat cta gca ggg aag cca aag     1020
Arg Met Phe Met Gly Asp Ser Cys Pro Tyr Leu Ala Gly Lys Pro Lys
    225                 230                 235 atg ttt ttt att cag aac tat gtg gtg tca gac ggc cag ctg gag gac     1068
Met Phe Phe Ile Gln Asn Tyr Val Val Ser Asp Gly Gln Leu Glu Asp
240                 245                 250                 255 agc agc ctc ttg gag gtg gat ggg cca gcg atg aag aat gtg gaa ttc     1116
Ser Ser Leu Leu Glu Val Asp Gly Pro Ala Met Lys Asn Val Glu Phe
                260                 265                 270 aag gct cag aag cga ggg ctg tgc aca gtt cac cga gaa gct gac ttc     1164
Lys Ala Gln Lys Arg Gly Leu Cys Thr Val His Arg Glu Ala Asp Phe
            275                 280                 285 ttc tgg agc ctg tgt act gcg gac atg tcc ctg ctg gag cag tct cac     1212
Phe Trp Ser Leu Cys Thr Ala Asp Met Ser Leu Leu Glu Gln Ser His
        290                 295                 300 agc tca ccg tcc ctg tac ctg cag tgc ctc tcc cag aaa ctg aga caa     1260
Ser Ser Pro Ser Leu Tyr Leu Gln Cys Leu Ser Gln Lys Leu Arg Gln
    305                 310                 315 gaa agg ggg aca att ccc gga agt gga att aca gag tca aag gac atg     1308
Glu Arg Gly Thr Ile Pro Gly Ser Gly Ile Thr Glu Ser Lys Asp Met
320                 325                 330                 335 cat ttt tca agc ctc gga tgc atc tta cta gat gtc cta taggatggtc     1357
His Phe Ser Ser Leu Gly Cys Ile Leu Leu Asp Val Leu
                340                 345 atatcagctt tataggagag tagctgtgtc cctgaattct ccctgacact gcatgctctt     1417
atatttcctc aagttttgac aatttgatag gtgaaaagtg gtatctgact gttcagatct     1477
ggaaggcttt gttatataaa cattttttta atgtttattg gcaagaatac ttttctaaga     1537
gaaacatcag tgagctggtt tccatttaag ctgaatgaag ccacaatgta cctcaagtat     1597
aagattaact ggcctttttc agttgcactc taattacaat ttagaatgat gtttctgagc     1657
cacctgtcaa atgcattctg ggctgtacct ctgcgtaccc aggaataaa tctcatggcc      1717 ttctttacct ggcctcctta gtggtggccc agcaggaagc gggggttaga gcaggagcca     1777
ctcagccttc aagatagat actccatggg ccggtggtat tactggcctt ttgagcccat      1837
ccccatttgc atagatgatc cacgtgggtt atcatctggc tggtatgttc ccagagtgaa     1897
actcagcagc cccttgaggg aggggatggt ggccatcagg ccagagtatt gcaagttagt     1957
ttggatcatt tgctaagcag cttgtggtgc cttcagaaag gaacagtttc aaagaacttt     2017
cacatctgtt ggctcatttc gccctaatga cagtcttctc tttgatattt gcatggcatt     2077
aaattttgcc tttcttgttt tctccagaaa acgcccactc ctggatcttc acattgaact     2137
caatggctac atgtatgatt ggaacagcag agtttctgcc aaggagaaat attatgtctg     2197
gctgcagcac actctgagaa agaaacttat ctctcctaca cataagaaac caaaaggctg     2257
ggcgtagtgg ctcgcacctg tgatcccagc actttgggag gccgaggagg gcggatcact     2317
tcaggtcggg agttcgagac cagcctggcc agcatgtgaa cgctgtccct agtagaagtg     2377
caaaaattgg ctggtgtggg tgtgggtacc ctgtattccc agttgcttgg ggggctgagg     2437
tgggaggatc ttttgacccc aggagttcag ggtcatagca tgctgtgatt gtgcctacga     2497
```
atagccactg cataccaacc tgggcaatat agcaagatcc catctcttta aaaaaaaaa        2557 aaaaaggaca ggaactatct taaaaaaaaa aaaaaaaaa                             2597

<210> SEQ ID NO 6
<211> LENGTH: 348
<212> TYPE: PRT
<213> ORGANISM: Homo sapiens

<400> SEQUENCE: 6

```
Met Ala Glu Ile Gly Glu Asp Leu Asp Lys Ser Asp Val Ser Ser Leu
1               5                   10                  15

Ile Phe Leu Met Lys Asp Tyr Met Gly Arg Gly Lys Ile Ser Lys Glu
            20                  25                  30

Lys Ser Phe Leu Asp Leu Val Glu Leu Glu Lys Leu Asn Leu Val
        35                  40                  45

Ala Pro Asp Gln Leu Asp Leu Leu Glu Lys Cys Leu Lys Asn Ile His
    50                  55                  60

Arg Ile Asp Leu Lys Thr Lys Ile Gln Lys Tyr Lys Gln Ser Val Gln
65                  70                  75                  80

Gly Ala Gly Thr Ser Tyr Arg Asn Val Leu Gln Ala Ile Gln Lys
                85                  90                  95

Ser Leu Lys Asp Pro Ser Asn Asn Phe Arg Glu Pro Val Lys Lys
            100                 105                 110

Ser Ile Gln Glu Ser Glu Ala Phe Leu Pro Gln Ser Ile Pro Glu Glu
        115                 120                 125

Arg Tyr Lys Met Lys Ser Lys Pro Leu Gly Ile Cys Leu Ile Ile Asp
    130                 135                 140

Cys Ile Gly Asn Glu Thr Glu Leu Leu Arg Asp Thr Phe Thr Ser Leu
145                 150                 155                 160

Gly Tyr Glu Val Gln Lys Phe Leu His Leu Ser Met His Gly Ile Ser
                165                 170                 175

Gln Ile Leu Gly Gln Phe Ala Cys Met Pro Glu His Arg Asp Tyr Asp
            180                 185                 190

Ser Phe Val Cys Val Leu Val Ser Arg Gly Gly Ser Gln Ser Val Tyr
        195                 200                 205

Gly Val Asp Gln Thr His Ser Gly Leu Pro Leu His His Ile Arg Arg
    210                 215                 220

Met Phe Met Gly Asp Ser Cys Pro Tyr Leu Ala Gly Lys Pro Lys Met
225                 230                 235                 240

Phe Phe Ile Gln Asn Tyr Val Val Ser Asp Gly Gln Leu Glu Asp Ser
                245                 250                 255

Ser Leu Leu Glu Val Asp Gly Pro Ala Met Lys Asn Val Glu Phe Lys
            260                 265                 270

Ala Gln Lys Arg Gly Leu Cys Thr Val His Arg Glu Ala Asp Phe Phe
        275                 280                 285

Trp Ser Leu Cys Thr Ala Asp Met Ser Leu Leu Glu Gln Ser His Ser
    290                 295                 300

Ser Pro Ser Leu Tyr Leu Gln Cys Leu Ser Gln Lys Leu Arg Gln Glu
305                 310                 315                 320

Arg Gly Thr Ile Pro Gly Ser Gly Ile Thr Glu Ser Lys Asp Met His
                325                 330                 335

Phe Ser Ser Leu Gly Cys Ile Leu Leu Asp Val Leu
            340                 345
```

```
<210> SEQ ID NO 7
<211> LENGTH: 26
<212> TYPE: DNA
<213> ORGANISM: Artificial sequence
<220> FEATURE:
<223> OTHER INFORMATION: Primer

<400> SEQUENCE: 7
cgcccatggc tgaagtcatc catcag                                          26

<210> SEQ ID NO 8
<211> LENGTH: 27
<212> TYPE: DNA
<213> ORGANISM: Artificial sequence
<220> FEATURE:
<223> OTHER INFORMATION: Primer

<400> SEQUENCE: 8
cgcaagcttg tgctgggatt acaggtg                                         27

<210> SEQ ID NO 9
<211> LENGTH: 26
<212> TYPE: DNA
<213> ORGANISM: Artificial sequence
<220> FEATURE:
<223> OTHER INFORMATION: Primer

<400> SEQUENCE: 9
cgcccatgga gattggtgag gatttg                                          26

<210> SEQ ID NO 10
<211> LENGTH: 26
<212> TYPE: DNA
<213> ORGANISM: Artificial sequence
<220> FEATURE:
<223> OTHER INFORMATION: Primer

<400> SEQUENCE: 10
cgcaagctta gagcatgcag tgtcag                                          26

<210> SEQ ID NO 11
<211> LENGTH: 33
<212> TYPE: DNA
<213> ORGANISM: Artificial sequence
<220> FEATURE:
<223> OTHER INFORMATION: Primer

<400> SEQUENCE: 11
cgcggatccg ccatcatgtc tgctgaagtc atc                                  33

<210> SEQ ID NO 12
<211> LENGTH: 27
<212> TYPE: DNA
<213> ORGANISM: Artificial sequence
<220> FEATURE:
<223> OTHER INFORMATION: Primer

<400> SEQUENCE: 12
cgcggtaccg tgctgggatt acaggtg                                         27

<210> SEQ ID NO 13
<211> LENGTH: 33
<212> TYPE: DNA
<213> ORGANISM: Artificial sequence
<220> FEATURE:
<223> OTHER INFORMATION: Primer
```

<400> SEQUENCE: 13
cgcggatccg ccatcatggc agagattggt gag                          33

<210> SEQ ID NO 14
<211> LENGTH: 26
<212> TYPE: DNA
<213> ORGANISM: Artificial sequence
<220> FEATURE:
<223> OTHER INFORMATION: Primer

<400> SEQUENCE: 14
cgcggtacca gagcatgcag tgtcag                                  26

<210> SEQ ID NO 15
<211> LENGTH: 33
<212> TYPE: DNA
<213> ORGANISM: Artificial sequence
<220> FEATURE:
<223> OTHER INFORMATION: Primer

<400> SEQUENCE: 15
cgccccgggg ccatcatgtc tgctgaagtc atc                          33

<210> SEQ ID NO 16
<211> LENGTH: 57
<212> TYPE: DNA
<213> ORGANISM: Artificial sequence
<220> FEATURE:
<223> OTHER INFORMATION: Primer

<400> SEQUENCE: 16
cgctctagat caagcgtagt ctgggacgtc gtatgggtag tgctgggatt acaggtg    57

<210> SEQ ID NO 17
<211> LENGTH: 33
<212> TYPE: DNA
<213> ORGANISM: Artificial sequence
<220> FEATURE:
<223> OTHER INFORMATION: Primer

<400> SEQUENCE: 17
cgcggatccg ccatcatgtc tgctgaagtc atc                          33

<210> SEQ ID NO 18
<211> LENGTH: 27
<212> TYPE: DNA
<213> ORGANISM: Artificial sequence
<220> FEATURE:
<223> OTHER INFORMATION: Primer

<400> SEQUENCE: 18
cgcggtaccg tgctgggatt acaggtg                                 27

<210> SEQ ID NO 19
<211> LENGTH: 33
<212> TYPE: DNA
<213> ORGANISM: Artificial sequence
<220> FEATURE:
<223> OTHER INFORMATION: Primer

<400> SEQUENCE: 19
cgcggatccg ccatcatggc agagattggt gag                          33

<210> SEQ ID NO 20

```
<211> LENGTH: 56
<212> TYPE: DNA
<213> ORGANISM: Artificial sequence
<220> FEATURE:
<223> OTHER INFORMATION: Primer

<400> SEQUENCE: 20
cgctctagat caagcgtagt ctgggacgtc gtatgggtaa gagcatgcag tgtcag        56

<210> SEQ ID NO 21
<211> LENGTH: 33
<212> TYPE: DNA
<213> ORGANISM: Artificial sequence
<220> FEATURE:
<223> OTHER INFORMATION: Primer

<400> SEQUENCE: 21
cgcggatccg ccatcatggc agagattggt gag        33

<210> SEQ ID NO 22
<211> LENGTH: 26
<212> TYPE: DNA
<213> ORGANISM: Artificial sequence
<220> FEATURE:
<223> OTHER INFORMATION: Primer

<400> SEQUENCE: 22
cgcggtacca gagcatgcag tgtcag        26

<210> SEQ ID NO 23
<211> LENGTH: 414
<212> TYPE: DNA
<213> ORGANISM: Homo sapiens
<220> FEATURE:
<221> NAME/KEY: misc_feature
<222> LOCATION: (16)..(16)
<223> OTHER INFORMATION: May be any nucleotide.
<220> FEATURE:
<221> NAME/KEY: misc_feature
<222> LOCATION: (309)..(309)
<223> OTHER INFORMATION: May be any nucleotide.
<220> FEATURE:
<221> NAME/KEY: misc_feature
<222> LOCATION: (317)..(317)
<223> OTHER INFORMATION: May be any nucleotide.
<220> FEATURE:
<221> NAME/KEY: misc_feature
<222> LOCATION: (342)..(342)
<223> OTHER INFORMATION: May be any nucleotide.
<220> FEATURE:
<221> NAME/KEY: misc_feature
<222> LOCATION: (358)..(358)
<223> OTHER INFORMATION: May be any nucleotide.
<220> FEATURE:
<221> NAME/KEY: misc_feature
<222> LOCATION: (367)..(367)
<223> OTHER INFORMATION: May be any nucleotide.
<220> FEATURE:
<221> NAME/KEY: misc_feature
<222> LOCATION: (380)..(380)
<223> OTHER INFORMATION: May be any nucleotide.
<220> FEATURE:
<221> NAME/KEY: misc_feature
<222> LOCATION: (386)..(386)
<223> OTHER INFORMATION: May be any nucleotide.
<220> FEATURE:
<221> NAME/KEY: misc_feature
<222> LOCATION: (409)..(409)
<223> OTHER INFORMATION: May be any nucleotide.

<400> SEQUENCE: 23
aattcggcac gagggnggac ttggctgaac tgctctacag agtgaggcga tttgacctgc        60
```

-continued

```
tcaaacgtat cttgaagatg gacagaaaag ctgtggagac ccacctgctc aggaaccctc        120
accttgtttc ggactataga gtgctgatgg cagagattgg tgaggatttg gataaatctg        180
atgtgtcctc attaattttc ctcatgaagg attacatggg ccgaggcaag ataagcaagg        240
agaagagttt cttgggacct tggtggttga gttgggagaa actaaatctg gtttgcccca        300
gatcaactng ggatttntta ggaaaaatgc ctaaagaaca tncacaggat agacctgnag        360
acaaaantcc agnagtacan gcagtntgtt cagggagcag ggacaattnc agga             414
```

<210> SEQ ID NO 24
<211> LENGTH: 393
<212> TYPE: DNA
<213> ORGANISM: Homo sapiens
<220> FEATURE:
<221> NAME/KEY: misc_feature
<222> LOCATION: (41)..(41)
<223> OTHER INFORMATION: May be any nucleotide.
<220> FEATURE:
<221> NAME/KEY: misc_feature
<222> LOCATION: (77)..(77)
<223> OTHER INFORMATION: May be any nucleotide.
<220> FEATURE:
<221> NAME/KEY: misc_feature
<222> LOCATION: (107)..(107)
<223> OTHER INFORMATION: May be any nucleotide.
<220> FEATURE:
<221> NAME/KEY: misc_feature
<222> LOCATION: (205)..(205)
<223> OTHER INFORMATION: May be any nucleotide.
<220> FEATURE:
<221> NAME/KEY: misc_feature
<222> LOCATION: (213)..(213)
<223> OTHER INFORMATION: May be any nucleotide.
<220> FEATURE:
<221> NAME/KEY: misc_feature
<222> LOCATION: (317)..(317)
<223> OTHER INFORMATION: May be any nucleotide.
<220> FEATURE:
<221> NAME/KEY: misc_feature
<222> LOCATION: (327)..(327)
<223> OTHER INFORMATION: May be any nucleotide.
<220> FEATURE:
<221> NAME/KEY: misc_feature
<222> LOCATION: (363)..(363)
<223> OTHER INFORMATION: May be any nucleotide.
<220> FEATURE:
<221> NAME/KEY: misc_feature
<222> LOCATION: (380)..(380)
<223> OTHER INFORMATION: May be any nucleotide.
<220> FEATURE:
<221> NAME/KEY: misc_feature
<222> LOCATION: (382)..(382)
<223> OTHER INFORMATION: May be any nucleotide.

<400> SEQUENCE: 24

```
tgccaaggag aaatattatg tctggctgca gcacactctg ngaaagaaac ttatcctctc         60
ctacacataa gaaaccnaaa ggctgggcgt agtggctcac gcctgtnaat cccagcactt        120
tgggaggcca aggagggcag atcacttcag gtcaggagtt cgagaccagc ctggccaaca        180
tggtaaacgc tgtccctagt aaaantacaa anttagctg ggtgtgggtg tgggtacctg         240
tgttcccagt tacttgggag gctgaggtgg gaggatcttt tggaacccag gagtttcagg        300
gtcatagcat gctgtgnttg tgccctnacg aattagccac tgcattacca acctggggca        360
atnttaggca agatcccatn tntttaaaa aaa                                      393
```

<210> SEQ ID NO 25
<211> LENGTH: 309
<212> TYPE: DNA

```
<213> ORGANISM: Homo sapiens
<220> FEATURE:
<221> NAME/KEY: misc_feature
<222> LOCATION: (229)..(229)
<223> OTHER INFORMATION: May be any nucleotide.
<220> FEATURE:
<221> NAME/KEY: misc_feature
<222> LOCATION: (286)..(286)
<223> OTHER INFORMATION: May be any nucleotide.

<400> SEQUENCE: 25
tggatcttca cattgaactc aatggctaca tgtatgattg aacagcaga gtttctgcca      60 aggagaaata ttatgtctgg ctgcagcaca ctctgagaaa gaaacttatc ctctcctaca    120
cataagaaac caaaaggctg ggcgtagtgg ctcacgcctg tgatcccagc actttgggag    180 gccgggagg gcagatcact tcaggtcagg agttcgagac cggcctggnc aacatggtag     240
acgctgtccc tagtaaaaat gcaaaagttg gctgggtgtg ggtgtnggta cctgtgttcc    300
cagttgctt                                                            309

<210> SEQ ID NO 26
<211> LENGTH: 500
<212> TYPE: DNA
<213> ORGANISM: Homo sapiens
<220> FEATURE:
<221> NAME/KEY: misc_feature
<222> LOCATION: (117)..(117)
<223> OTHER INFORMATION: May be any nucleotide.
<220> FEATURE:
<221> NAME/KEY: misc_feature
<222> LOCATION: (170)..(170)
<223> OTHER INFORMATION: May be any nucleotide.
<220> FEATURE:
<221> NAME/KEY: misc_feature
<222> LOCATION: (226)..(226)
<223> OTHER INFORMATION: May be any nucleotide.
<220> FEATURE:
<221> NAME/KEY: misc_feature
<222> LOCATION: (287)..(287)
<223> OTHER INFORMATION: May be any nucleotide.
<220> FEATURE:
<221> NAME/KEY: misc_feature
<222> LOCATION: (295)..(295)
<223> OTHER INFORMATION: May be any nucleotide.
<220> FEATURE:
<221> NAME/KEY: misc_feature
<222> LOCATION: (305)..(305)
<223> OTHER INFORMATION: May be any nucleotide.
<220> FEATURE:
<221> NAME/KEY: misc_feature
<222> LOCATION: (332)..(332)
<223> OTHER INFORMATION: May be any nucleotide.
<220> FEATURE:
<221> NAME/KEY: misc_feature
<222> LOCATION: (339)..(339)
<223> OTHER INFORMATION: May be any nucleotide.
<220> FEATURE:
<221> NAME/KEY: misc_feature
<222> LOCATION: (349)..(349)
<223> OTHER INFORMATION: May be any nucleotide.
<220> FEATURE:
<221> NAME/KEY: misc_feature
<222> LOCATION: (353)..(353)
<223> OTHER INFORMATION: May be any nucleotide.
<220> FEATURE:
<221> NAME/KEY: misc_feature
<222> LOCATION: (355)..(355)
<223> OTHER INFORMATION: May be any nucleotide.
<220> FEATURE:
<221> NAME/KEY: misc_feature
<222> LOCATION: (362)..(362)
<223> OTHER INFORMATION: May be any nucleotide.
<220> FEATURE:
<221> NAME/KEY: misc_feature
```

```
<222> LOCATION: (364)..(364)
<223> OTHER INFORMATION: May be any nucleotide.
<220> FEATURE:
<221> NAME/KEY: misc_feature
<222> LOCATION: (392)..(392)
<223> OTHER INFORMATION: May be any nucleotide.
<220> FEATURE:
<221> NAME/KEY: misc_feature
<222> LOCATION: (398)..(398)
<223> OTHER INFORMATION: May be any nucleotide.
<220> FEATURE:
<221> NAME/KEY: misc_feature
<222> LOCATION: (405)..(405)
<223> OTHER INFORMATION: May be any nucleotide.
<220> FEATURE:
<221> NAME/KEY: misc_feature
<222> LOCATION: (412)..(412)
<223> OTHER INFORMATION: May be any nucleotide.
<220> FEATURE:
<221> NAME/KEY: misc_feature
<222> LOCATION: (445)..(445)
<223> OTHER INFORMATION: May be any nucleotide.
<220> FEATURE:
<221> NAME/KEY: misc_feature
<222> LOCATION: (448)..(448)
<223> OTHER INFORMATION: May be any nucleotide.
<220> FEATURE:
<221> NAME/KEY: misc_feature
<222> LOCATION: (459)..(459)
<223> OTHER INFORMATION: May be any nucleotide.
<220> FEATURE:
<221> NAME/KEY: misc_feature
<222> LOCATION: (469)..(469)
<223> OTHER INFORMATION: May be any nucleotide.
<220> FEATURE:
<221> NAME/KEY: misc_feature
<222> LOCATION: (480)..(480)
<223> OTHER INFORMATION: May be any nucleotide.

<400> SEQUENCE: 26
aattcggcag agctcactca gggctccccc tgcatcacat caggaggatg ttcatgggag      60
attcatgccc ttatctagca gggaagccaa agatgttttt tattcagaac tatgtgntgt     120
cagagggcca gctggaggac agcagcctct tggaggtgga tgggccagcn atgaagaatg     180
tggaattcaa ggctcagaag cgagggctgt gcacagttca ccgagnaagc tgacttcttc     240
tggagcctgt gtaatgcgga catgtccctg cttggagcaa tcttcanagg ttcancgtcc     300
ctgtnacctg catgccttt cccagaaact gngacaagna agaaaacgnc cantnctggg     360
gntntttcac attggaactc aatggttaca anttatgntt ggggncaaca antttttgc     420 caagggggaa tttttgtttt tgggntgnag aaaaatttng ggaaagaant tttcccttn     480 cnnnaaatta ggnacccaaa                                                500

<210> SEQ ID NO 27
<211> LENGTH: 324
<212> TYPE: DNA
<213> ORGANISM: Homo sapiens

<400> SEQUENCE: 27
attctgaaaa agaatgtggg gtttccttgc agatgagttc atctgttgtt tcatttcctt      60
tacaataact cccccactgg aaaggattct gaaagaaatg aagtcagccc tcagaaatga     120
agttgactgc ctgctggctt tctgttgact ggcctggagc tgtactgcaa gacccttgtg     180
agcttcccta gtctaagagt aggatgtctg ctgaagtcat ccatcaggtt gaagaagcac     240
ttgatacaga tgagaaggag atgctgctct ttttgtgccg ggatgttgct atagatgtgg     300
ttccacctaa tgtcagggac cttc                                           324
```

<210> SEQ ID NO 28
<211> LENGTH: 389
<212> TYPE: DNA
<213> ORGANISM: Homo sapiens
<220> FEATURE:
<221> NAME/KEY: misc_feature
<222> LOCATION: (1)..(1)
<223> OTHER INFORMATION: May be any nucleotide.
<220> FEATURE:
<221> NAME/KEY: misc_feature
<222> LOCATION: (15)..(15)
<223> OTHER INFORMATION: May be any nucleotide.
<220> FEATURE:
<221> NAME/KEY: misc_feature
<222> LOCATION: (115)..(115)
<223> OTHER INFORMATION: May be any nucleotide.
<220> FEATURE:
<221> NAME/KEY: misc_feature
<222> LOCATION: (282)..(282)
<223> OTHER INFORMATION: May be any nucleotide.
<220> FEATURE:
<221> NAME/KEY: misc_feature
<222> LOCATION: (318)..(318)
<223> OTHER INFORMATION: May be any nucleotide.
<220> FEATURE:
<221> NAME/KEY: misc_feature
<222> LOCATION: (335)..(335)
<223> OTHER INFORMATION: May be any nucleotide.
<220> FEATURE:
<221> NAME/KEY: misc_feature
<222> LOCATION: (353)..(353)
<223> OTHER INFORMATION: May be any nucleotide.
<220> FEATURE:
<221> NAME/KEY: misc_feature
<222> LOCATION: (356)..(356)
<223> OTHER INFORMATION: May be any nucleotide.
<220> FEATURE:
<221> NAME/KEY: misc_feature
<222> LOCATION: (362)..(362)
<223> OTHER INFORMATION: May be any nucleotide.
<220> FEATURE:
<221> NAME/KEY: misc_feature
<222> LOCATION: (364)..(364)
<223> OTHER INFORMATION: May be any nucleotide.
<220> FEATURE:
<221> NAME/KEY: misc_feature
<222> LOCATION: (374)..(374)
<223> OTHER INFORMATION: May be any nucleotide.

<400> SEQUENCE: 28
naattcggca gaganaagag tctcaaggat ccttcaaata acttcaggct ccataatggg      60
agaagtaaag aacaaagact taaggaacag cttggcgctc aacaagaacc agtgnaagaa     120
atccattcag gaatcagaag cttttttgcc tcagagcata cctgaagaga gatacaagat     180
gaagagcaag cccctaggga atctgcctga taaatcgatt gcattggcaa tgaggacaga     240
gcttcttcgg ggacaccttc acttccctgg gcttatgaag tnccaggaaa ttcttgcatc     300
tcagtatgca tggtattntc ccagattttt tgggnccaat ttgcccgtta tgnccngggc     360 ancngggat ttangacaat tttgtggtg                                       389

<210> SEQ ID NO 29
<211> LENGTH: 308
<212> TYPE: DNA
<213> ORGANISM: Homo sapiens
<220> FEATURE:
<221> NAME/KEY: misc_feature
<222> LOCATION: (14)..(14)
<223> OTHER INFORMATION: May be any nucleotide.
<220> FEATURE:
<221> NAME/KEY: misc_feature
<222> LOCATION: (17)..(17)
<223> OTHER INFORMATION: May be any nucleotide.

<220> FEATURE:
<221> NAME/KEY: misc_feature
<222> LOCATION: (45)..(45)
<223> OTHER INFORMATION: May be any nucleotide.
<220> FEATURE:
<221> NAME/KEY: misc_feature
<222> LOCATION: (96)..(96)
<223> OTHER INFORMATION: May be any nucleotide.
<220> FEATURE:
<221> NAME/KEY: misc_feature
<222> LOCATION: (126)..(126)
<223> OTHER INFORMATION: May be any nucleotide.

<400> SEQUENCE: 29

```
attctgaaaa agantgnggg gtttccttgc agatgagttc atctnttgtt tcatttcctt     60
tacaataact cccccactgg aaaggattct gaaagnaatg aagtcagccc tcagaaatga    120
agttgnctgc ctgctggctt tctgttgact ggcctggagc tgtactgcaa gacccttgtg    180
agcttcccta gtctaagagt aggatgtctg ctgaagtcat ccatcaggtt gaagaagcac    240
ttgatacaga tgagaaggag atgctgctct ttttgtgccg ggatgtttgc tatagatgtg    300
gttccacc                                                              308
```

<210> SEQ ID NO 30
<211> LENGTH: 297
<212> TYPE: DNA
<213> ORGANISM: Homo sapiens
<220> FEATURE:
<221> NAME/KEY: misc_feature
<222> LOCATION: (28)..(28)
<223> OTHER INFORMATION: May be any nucleotide.

<400> SEQUENCE: 30

```
attctgaaaa agaatgtggg gtttcctngc agatgagttc atctgttgtt tcatttcctt     60
tacaataact cccccactgg aaaggattct gaaagaaatg aagtcagccc tcagaaatga    120
agttgactgc ctgctggctt tctgttgact ggcctggagc tgtactgcaa gacccttgtg    180
agcttcccta gtctaagagt aggatgtctg ctgaagtcat ccatcaggtt gaagaagcac    240
ttgatacaga tgagaaggag atgctgctct ttttgtgcc gggatgttgc tatagat       297
```

<210> SEQ ID NO 31
<211> LENGTH: 348
<212> TYPE: DNA
<213> ORGANISM: Homo sapiens

<400> SEQUENCE: 31

```
tataggatgg tcatatcagc tttataggag agtagctgtg tccctgaatt ctccctgaca     60
ctgcatgctc ttatatttcc tcaagttttg acaatttgat aggtgaaaag tggtatctga    120
ttgttcagat ctggaaggct tgttatata aacatttttt taatgtttat tggcaagaat     180
acttttctaa gagaaacatc agtgagctgg tttccattta agctgaatga agccacaatg    240
tacctcaagt ataaggttaa ctggcctttt ttcagttgca ctctaattac aatttagaat    300
gatgtttctg agccacctgt caaatgcatt ctggggctgt acctcttg                 348
```

<210> SEQ ID NO 32
<211> LENGTH: 333
<212> TYPE: DNA
<213> ORGANISM: Homo sapiens
<220> FEATURE:
<221> NAME/KEY: misc_feature
<222> LOCATION: (48)..(48)
<223> OTHER INFORMATION: May be any nucleotide.
<220> FEATURE:

```
<221> NAME/KEY: misc_feature
<222> LOCATION: (125)..(125)
<223> OTHER INFORMATION: May be any nucleotide.
<220> FEATURE:
<221> NAME/KEY: misc_feature
<222> LOCATION: (248)..(248)
<223> OTHER INFORMATION: May be any nucleotide.
<220> FEATURE:
<221> NAME/KEY: misc_feature
<222> LOCATION: (310)..(310)
<223> OTHER INFORMATION: May be any nucleotide.

<400> SEQUENCE: 32
tataggatgg tcatatcagc tttataggag agtagctgtg tccctgantt ctccctgaca      60
ctgcatgctc ttatatttcc tcaagttttg acaatttgat aggtgaaaag tggtatctga     120
ctgtncagat ctggaaggct ttgttatata aacattttt taatgtttat tggcaagaat      180
acttttctaa gagaaacatc agtgagctgg tttccattta agctgaatga agccacaatg     240
tacctcangt ataaggatta actggccttt ttccagttgc actctaatta caattttaga     300
atgatgttcn gaggccacct gtcaaatgca ttc                                  333

<210> SEQ ID NO 33
<211> LENGTH: 5
<212> TYPE: PRT
<213> ORGANISM: Homo sapiens

<400> SEQUENCE: 33

Gln Ala Cys Arg Gly
1               5

<210> SEQ ID NO 34
<211> LENGTH: 5
<212> TYPE: PRT
<213> ORGANISM: Homo sapiens

<400> SEQUENCE: 34

Gln Ala Cys Gln Gly
1               5

<210> SEQ ID NO 35
<211> LENGTH: 5
<212> TYPE: PRT
<213> ORGANISM: Homo sapiens

<400> SEQUENCE: 35

Gln Asn Tyr Val Val
1               5
```